US006231568B1

United States Patent
Loeb et al.

(10) Patent No.: US 6,231,568 B1
(45) Date of Patent: May 15, 2001

(54) CHANNEL-FORMING LASER ENERGY DEVICE

(75) Inventors: Marvin P. Loeb, Huntington Beach; L. Dean Crawford, Irvine; Samuel M. Shaolian, Laguna Niguel, all of CA (US)

(73) Assignee: Cardiodyne, Inc., Irvine, CA (US)

( * ) Notice: Subject to any disclaimer, the term of this patent is extended or adjusted under 35 U.S.C. 154(b) by 0 days.

(21) Appl. No.: 09/307,512

(22) Filed: May 7, 1999

Related U.S. Application Data

(63) Continuation-in-part of application No. 08/790,546, filed on Jan. 30, 1997, now Pat. No. 5,913,853.

(51) Int. Cl.$^7$ .................................................. A61B 17/36
(52) U.S. Cl. ................................... 606/15; 606/7; 607/89
(58) Field of Search ............................... 606/2, 7, 13–16; 607/88, 89

(56) References Cited

U.S. PATENT DOCUMENTS

| | | |
|---|---|---|
| 4,658,817 | 4/1987 | Hardy . |
| 4,773,413 | 9/1988 | Hussein et al. . |
| 4,778,975 | 10/1988 | Shturman et al. . |
| 5,093,877 | 3/1992 | Aita et al. ............................ 385/34 |
| 5,125,926 | 6/1992 | Rudko et al. ......................... 606/19 |
| 5,380,816 | 1/1995 | Aita et al. ............................. 606/7 |
| 5,387,211 | 2/1995 | Saadatmanesh et al. ............. 606/10 |
| 5,389,096 | 2/1995 | Aita et al. ............................ 606/15 |
| 5,607,421 | 3/1997 | Jeevanandam et al. .............. 606/15 |
| 5,672,170 * | 9/1997 | Cho et al. ............................. 606/15 |
| 5,703,985 | 12/1997 | Owyang ............................ 385/117 |
| 5,713,894 | 2/1998 | Murphy-Chutorian et al. ....... 606/15 |
| 5,738,680 | 4/1998 | Mueller et al. ....................... 606/15 |
| 5,913,853 * | 6/1999 | Loeb et al. ........................... 606/15 |

OTHER PUBLICATIONS

Yano et al., Prevention of Acute Regional Ischemia With Endocardial Laser Channels, The Society of Thoracic Surgeons, 1993.
Lee et al., Effects of Laser Irradiation Delivered by Flexible Fiberoptic System on the Left Ventricular Internal Myocardium, American Heart Journal, Sep. 1983.
Mirhoseini et al., Clinical and Histological Evaluation of Laser Myocardial Revascularization, Journal of Clinical Laser Medicine & Surgery, Jun. 1990.
Mirhoseini et al., Revascularization of the Heart by Laser, Journal of Microsurgery, Jun. 1981.
Mirhoseini et al., Myocardial Revascularization by Laser: A Clinical Report, Lasers in Surgery and Medicine, 1983.
Mirhoseini et al., Transventricular Revascularizaiton by Lasers, Lasers in Surgery and Medicine, 1982.
Mirhoseini et al., Transmyocardial Laser Revascularization; A Review, Journal of Clinical Laser Medicine & Surgery, vol. 11, No. 1, Nov. 1, 1993.

(List continued on next page.)

Primary Examiner—Eric F. Winakur
(74) Attorney, Agent, or Firm—Olson & Hierl, Ltd.

(57) ABSTRACT

A surgical device is provided for forming a channel through or partially through vascular tissue, including vascular tissue, utilizing both mechanical and laser energy, and, if desired, depositing a therapeutic agent therein. The device includes an optical fiber for transmission of laser energy, a housing, and a hollow guide attached to the housing through which the optical fiber extends. A needle is attached to the distal end of the optical fiber in fluid communication with a catheter surrounding the optical fiber. Additionally, an actuator is included operably connected to the optical fiber for selectively extending the needle and/or fiber from the hollow guide. Finally, a laser control device is contemplated operably connected to the optical fiber, transmitting laser energy from the distal end of the fiber after the needle has penetrated a layer of selected distance into the tissue.

60 Claims, 38 Drawing Sheets

OTHER PUBLICATIONS

Okada et al., Alternative Method of Myocardial Revascularization By Laser: Experimental and Clinical Study, Kobe J. Medical Science 32, Oct. 1986.

Mirhoseini et al., New Concepts in Revascularization of the Myocardium, The Society of Thoracic Surgeons, Apr. 1988.

David Stipp, Punching Holes in the Heart with Lasers Can Stave Off Attacks When Arteries Clog, The Wall Street Journal, May 31, 1995.

Mirhoseini et al. Clinical Report: Laser Myocardial Revascularization, Lasers in Surgery and Medicine, 1986.

Jeevanandam et al., Myocardial Revascularization By Laser–Induced Channels, Surgical Forum, vol. 41, 1991.

M. Mirhoseini, Laser Applications in Thoracic and Cardiovascular Surgery, Medical Instrumentation. vol. 17, No. 6, Nov.–Dec. 1983.

* cited by examiner

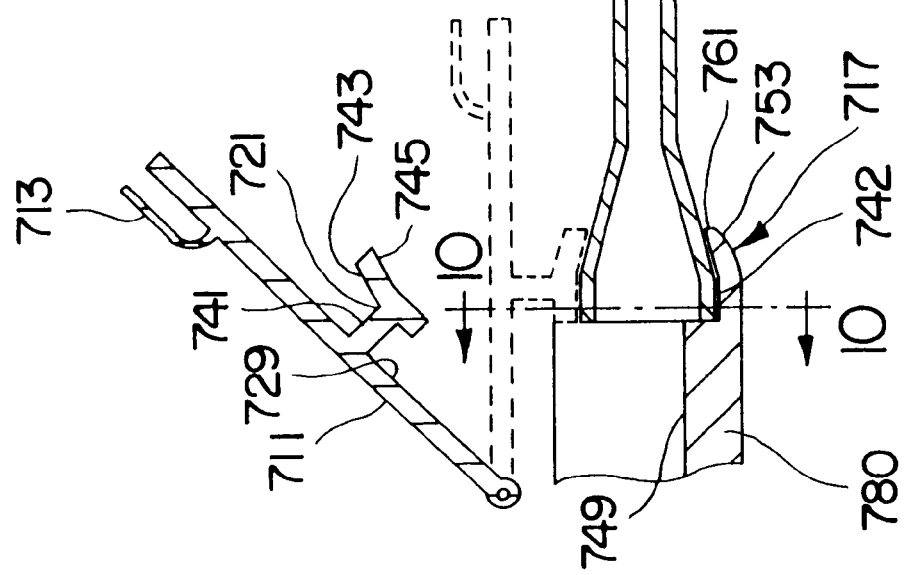

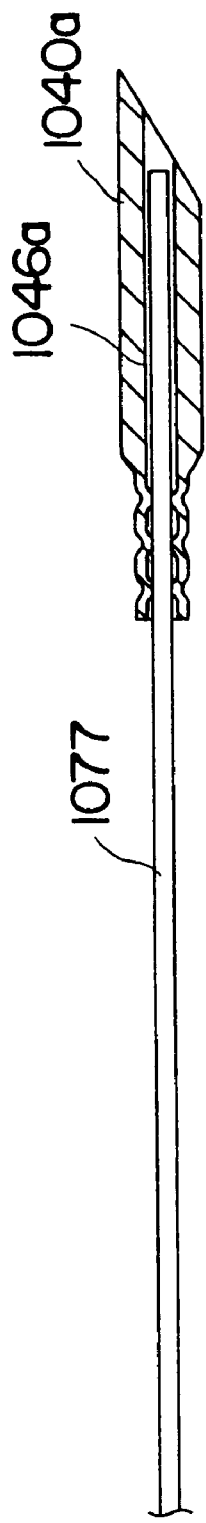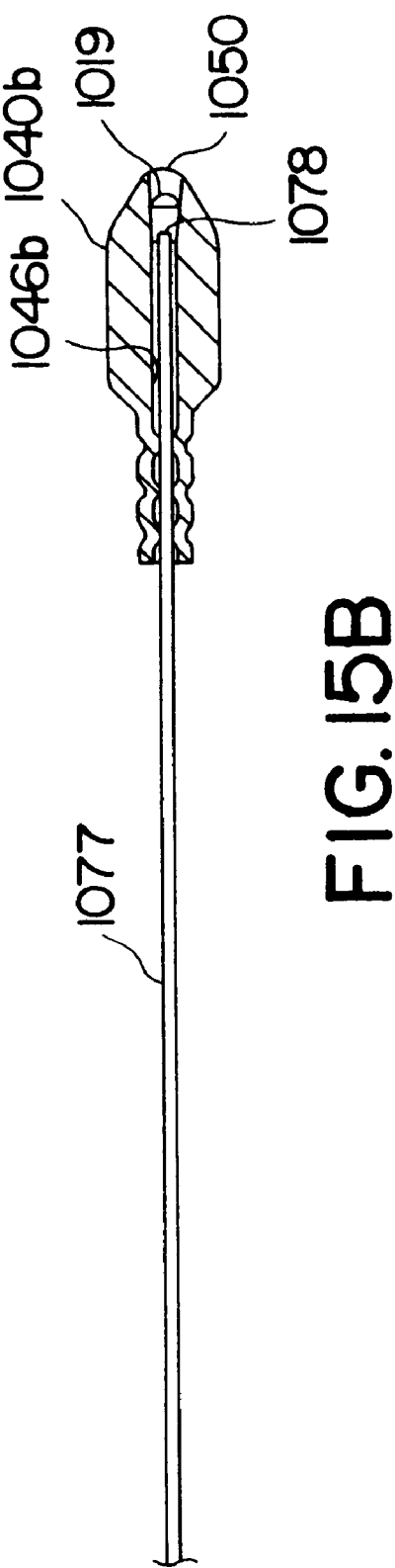

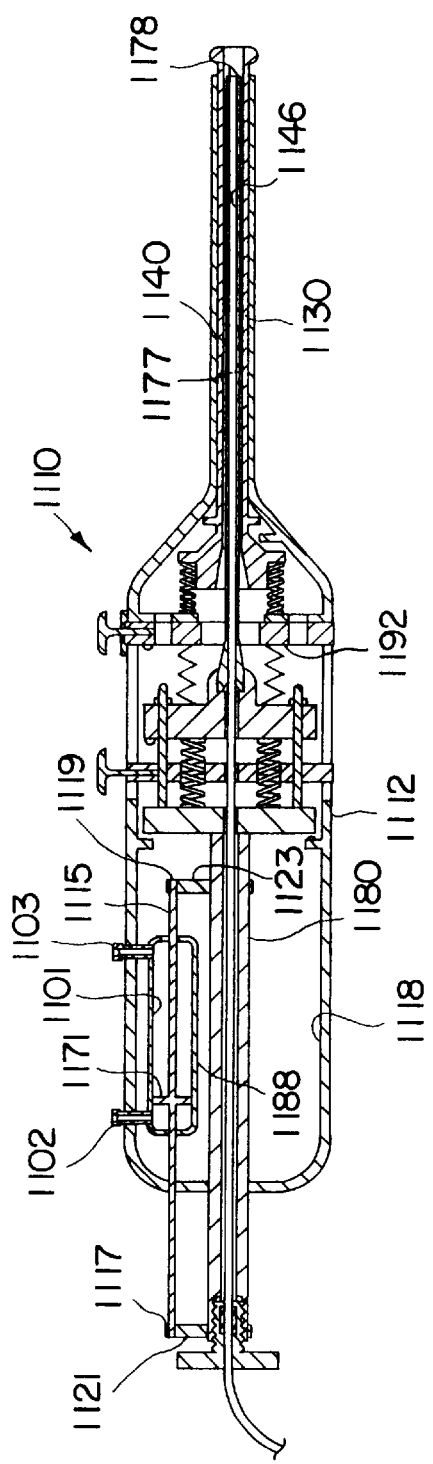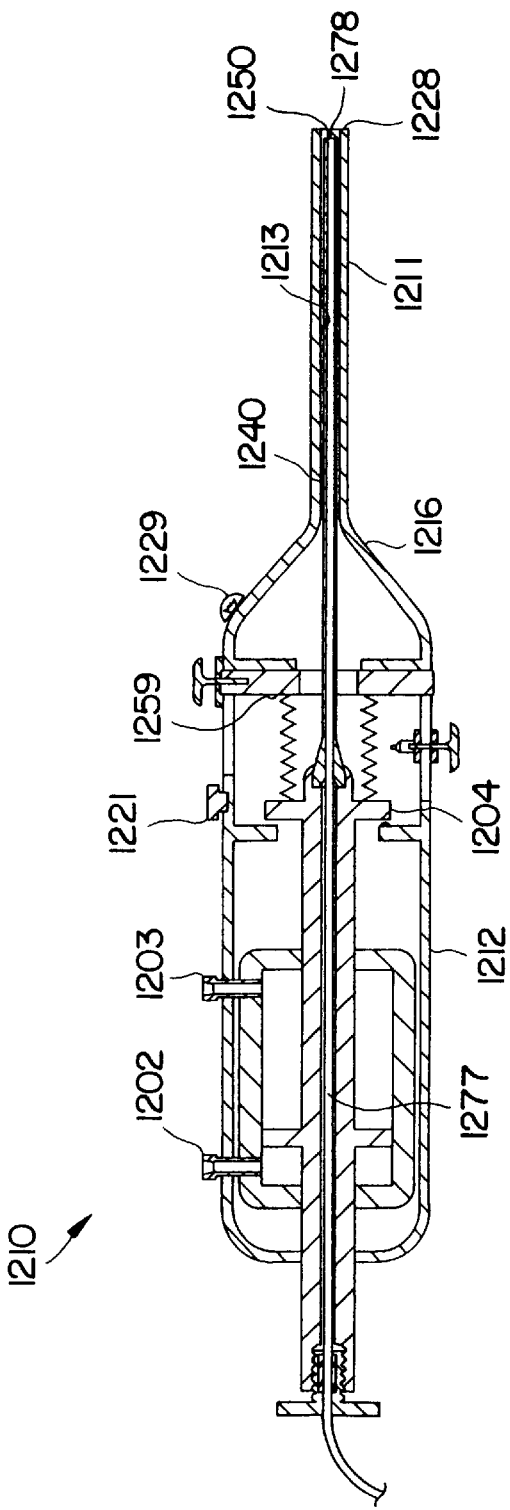

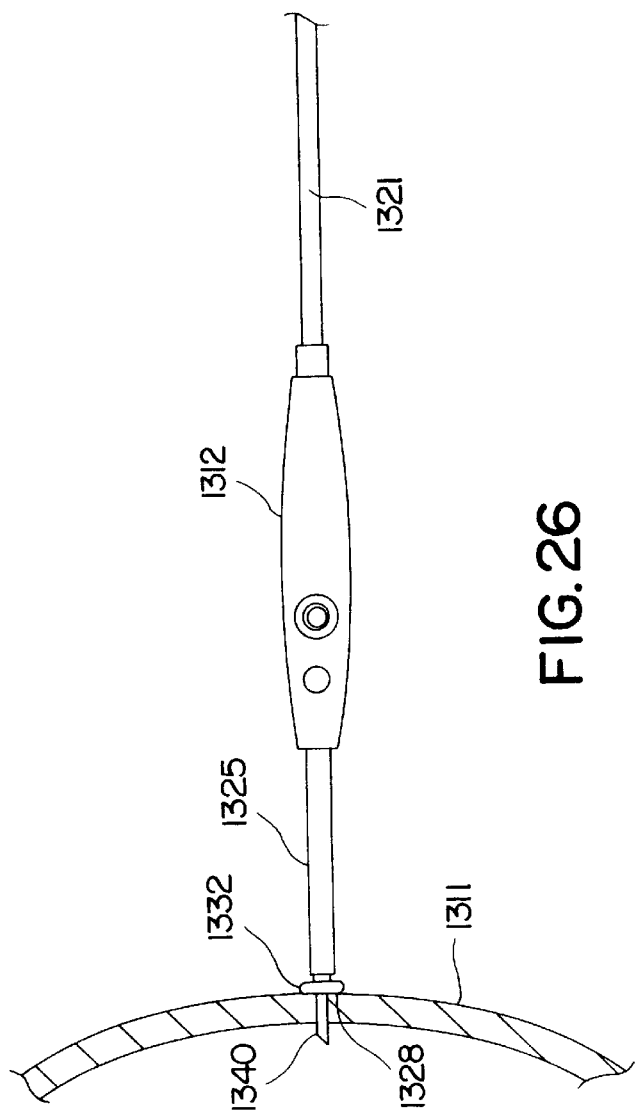
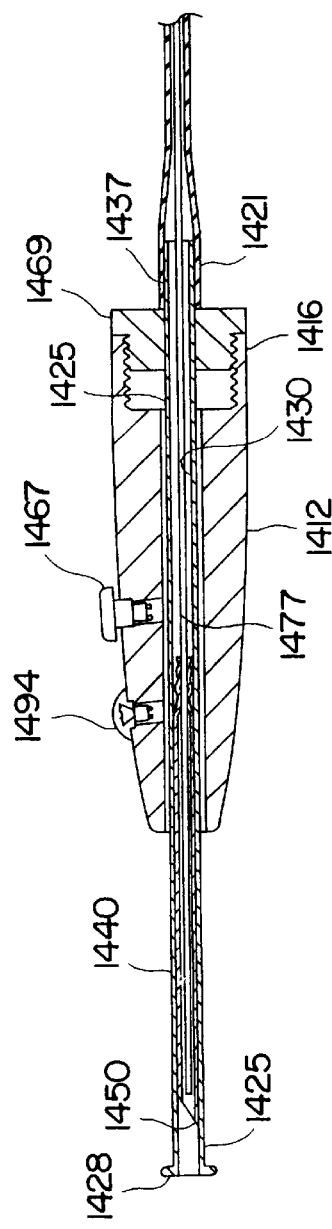
FIG. 26
FIG. 27

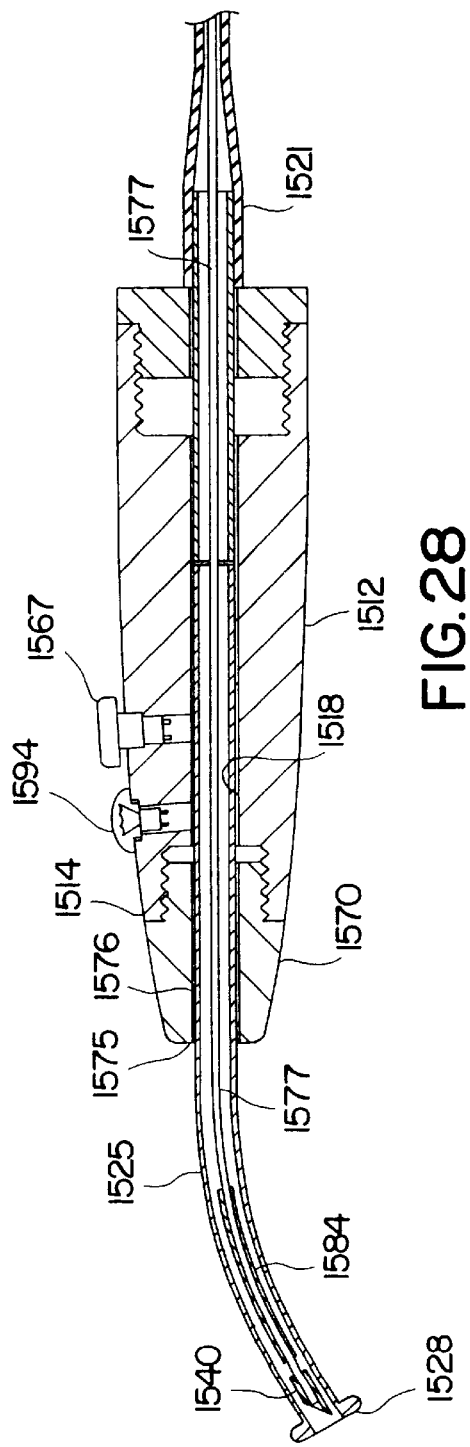
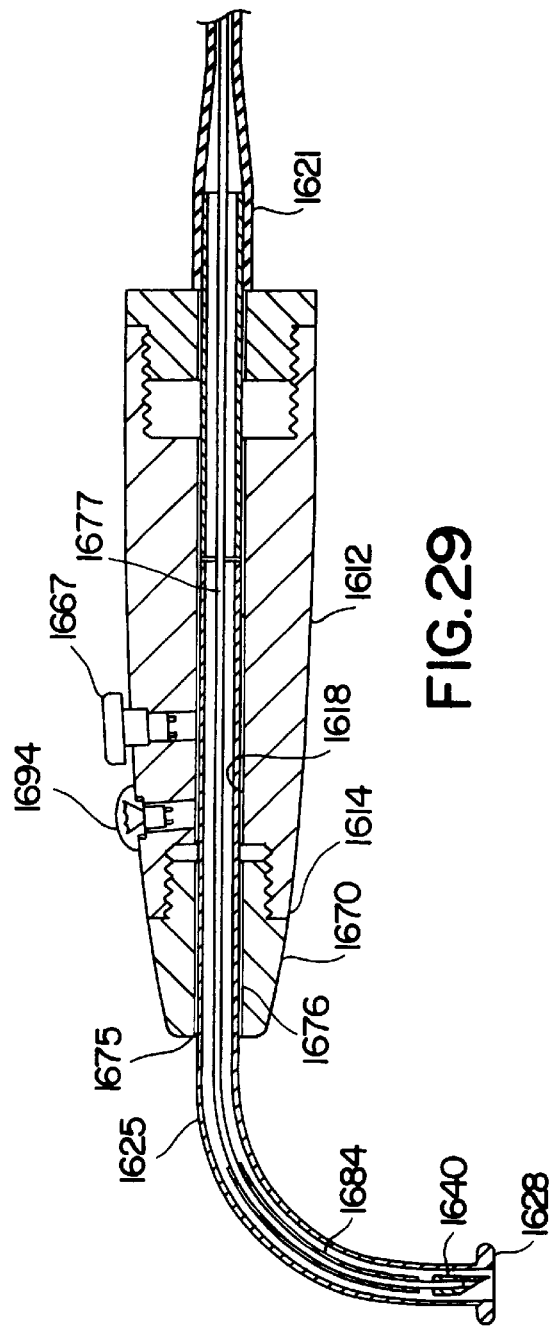
FIG.28
FIG.29

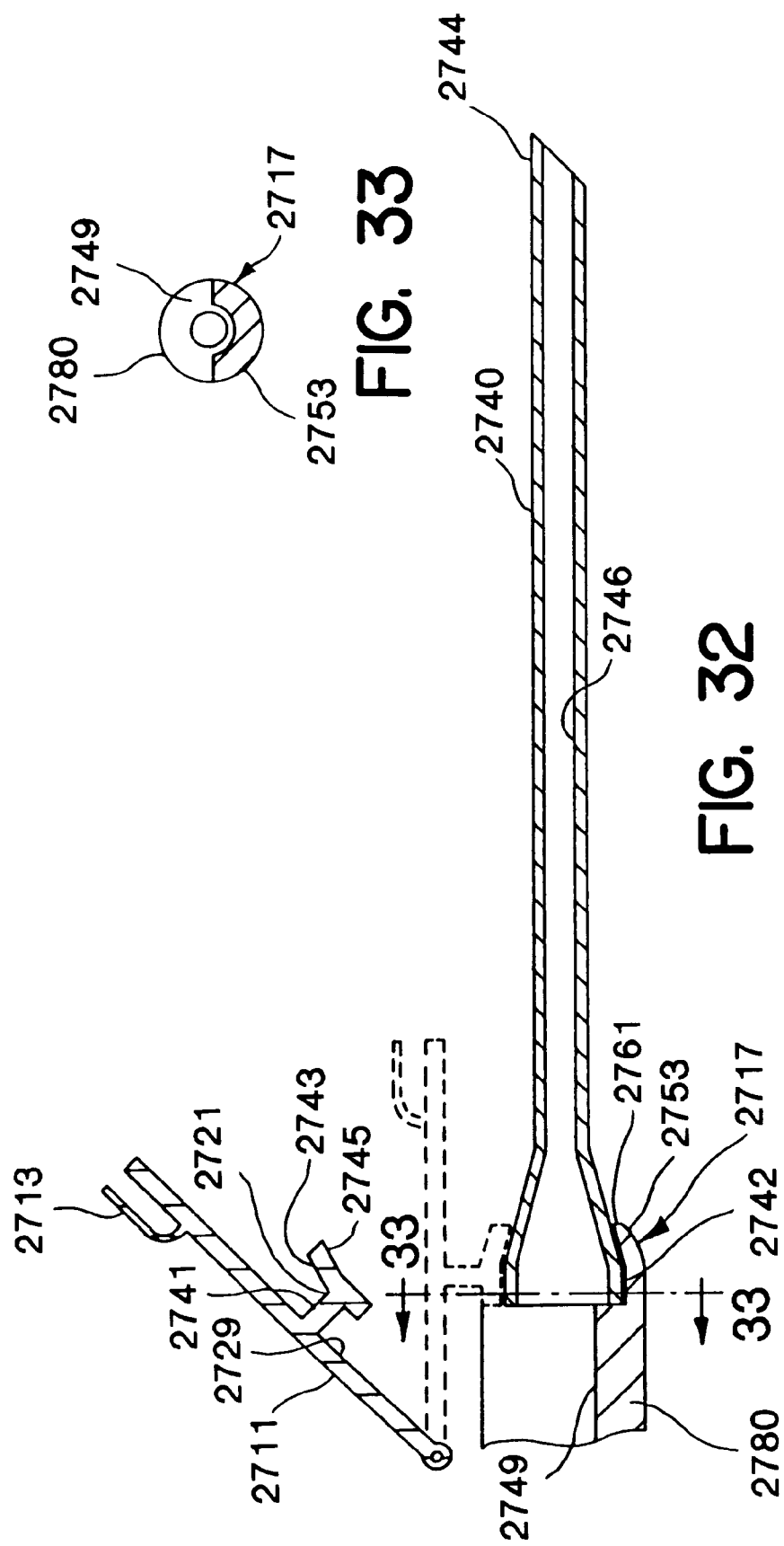

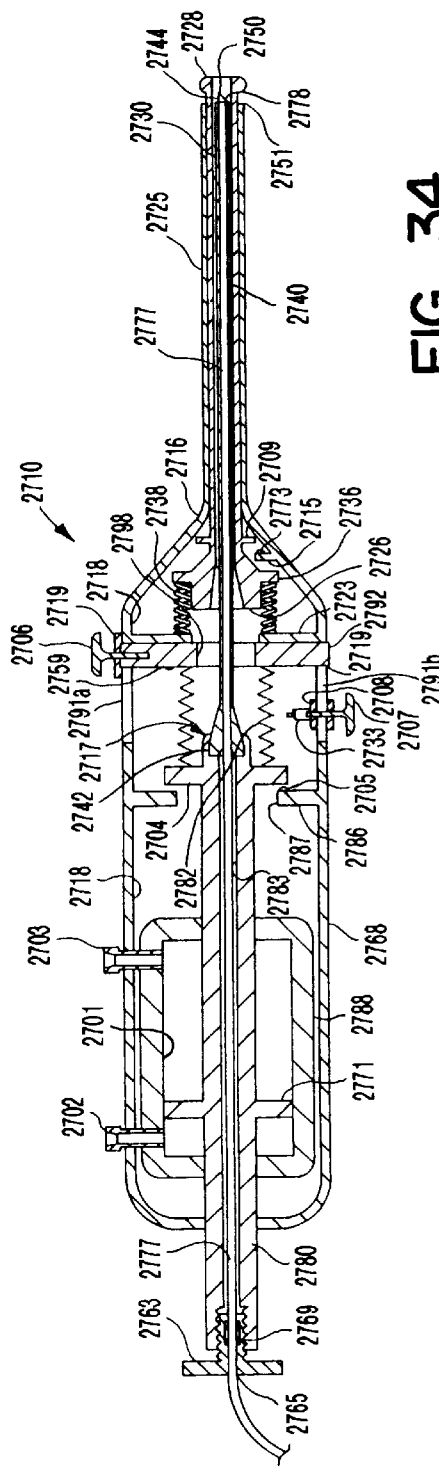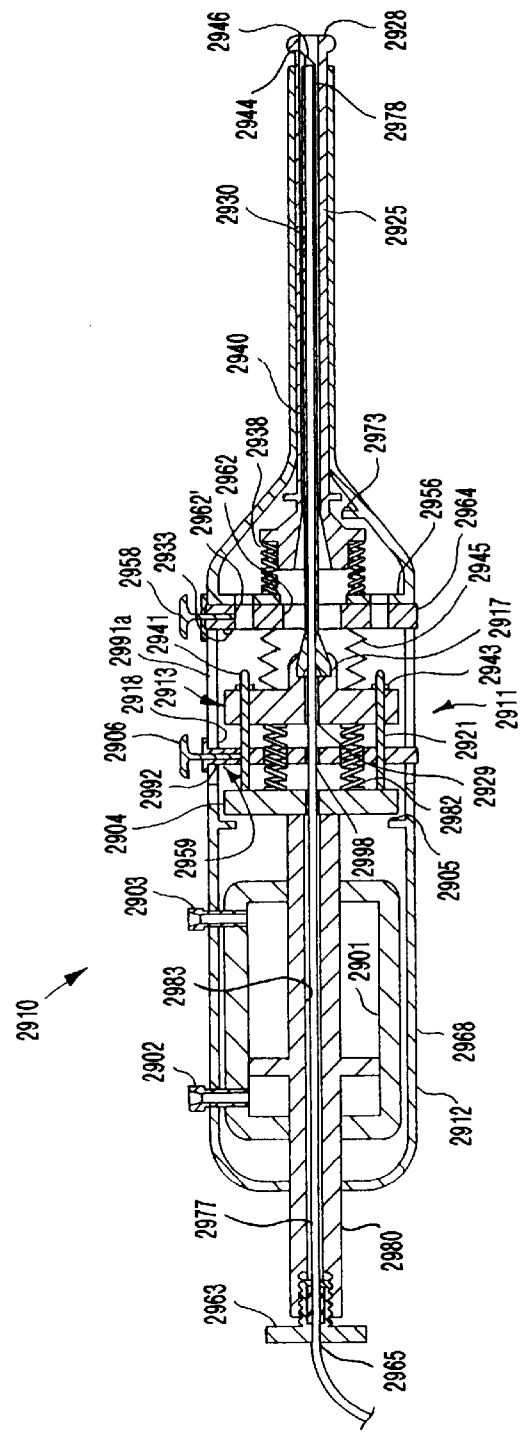

TMR COMMANDER™ DISPLAY

— 11374

| | | |
|---|---|---|
| TOTAL TIME IN & OUT | _____ msec. | ACTIVATE ON COMMAND ☐ |
| DISTANCE IN/OUT WITHOUT LASING | _____ mm. | ACTIVATE ON "R" WAVE ☐ |
| DISTANCE IN/OUT WITH LASING | _____ mm. | CUM. NO. CHANNELS _____ |
| T. DISTANCE IN & OUT | _____ mm. | RESET CHANNELS TO ZERO ☐ |

11331, 11364 (markers on triangular indicators)

© CARDIODYNE, INC.

FIG. 47

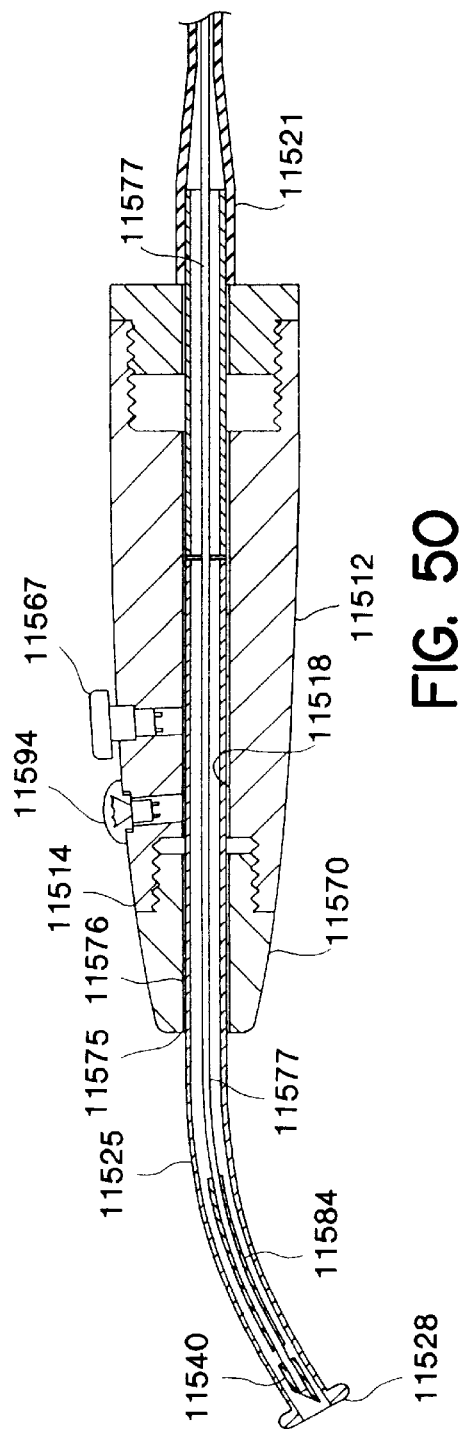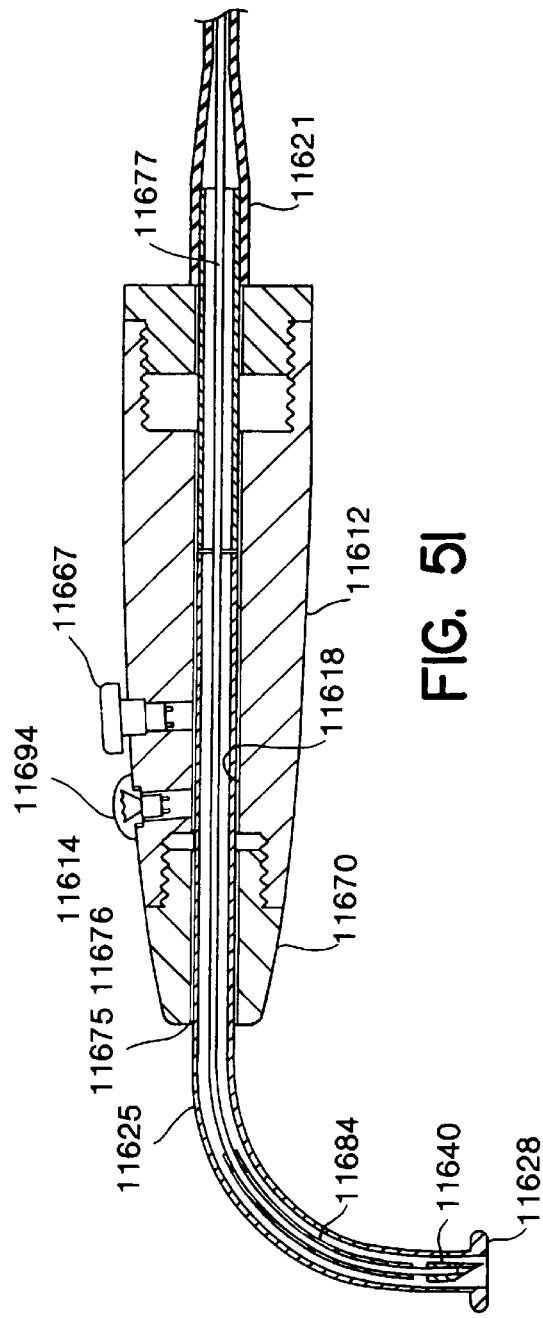
FIG. 50
FIG. 51

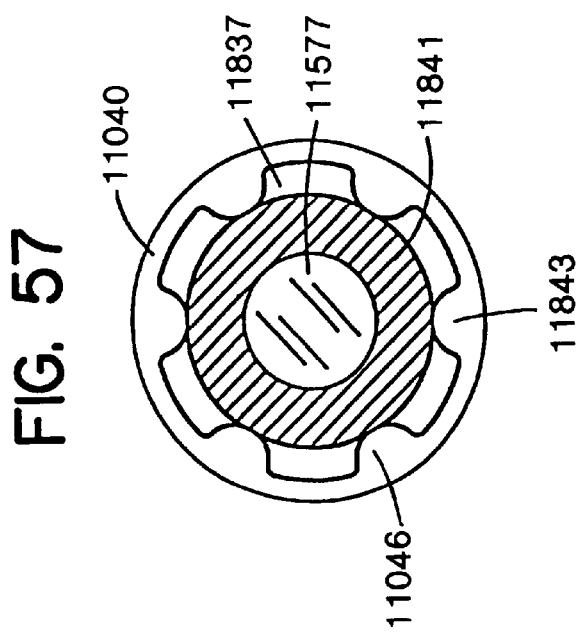
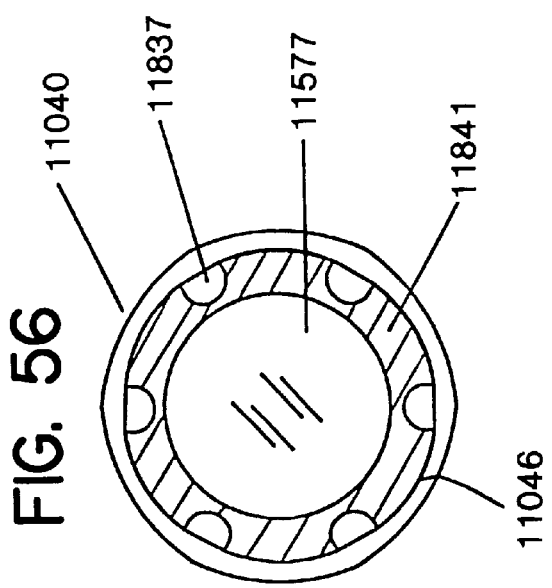
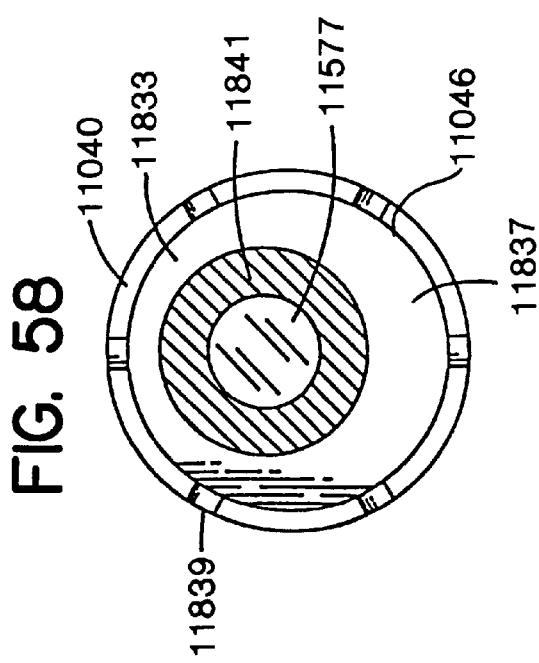

CHANNEL-FORMING LASER ENERGY DEVICE

CROSS-REFERENCE TO RELATED APPLICATION

This specification is a continuation-in-part of application, Ser. No. 08/790,546 filed on Jan. 30, 1997, now U.S. Pat. No. 5,913,853.

FIELD OF THE INVENTION

The present invention relates to surgical devices and procedures for the delivery of a combination of mechanical and laser energy to form a channel within vascular tissue, and in particular to a device and procedure which forms a channel partially by mechanical energy and partially by emitting laser energy directly onto the tissue to be treated.

BACKGROUND OF THE INVENTION

A human heart receives its blood supply from the coronary arteries which branch out and around the heart muscle. Conversely, in a reptile, little or no arterial supply of blood is provided to the heart muscle. Instead, the blood supply is mainly delivered through the inside wall of the heart chamber.

Modifying a human heart to imitate the blood delivery method of a reptile heart is currently being used as an alternative or adjunct to coronary artery bypass graft surgery and coronary balloon angioplasty. Normally, a person can only undergo coronary bypass surgery twice, since the risks will begin to outweigh the benefits after that point. Thus, in the past, a patient who has already had two coronary bypass surgeries was left with no recourse. Others have failed repeated coronary balloon angioplasties, and many persons are not suitable candidates for coronary bypass surgery or coronary balloon angioplasty. These persons likewise are left with no recourse.

Early attempts to imitate the reptilian condition in mammals, known as transmyocardial revascularization (TMR), consisted of producing tiny channels in mammalian and human hearts with needles or hot wires. This method met with limited success since, although the channels closed by clotting at the outside surface of the heart, due to exposure to air, and did allow for some internal blood delivery, the channels soon healed over entirely and failed to continue the blood supply. Early attempts were also made to graft a blood vessel from the aorta directly into the heart muscle to provide an internal source of blood. While some benefits were seen, the surgery was technically demanding and the procedure was eclipsed by the introduction of coronary artery bypass graft surgery.

To overcome these problems, Mahmood Mirhoseini and Mary M. Cayton suggest transmyocardial revascularization by using a high-powered $CO_2$ laser to make the channels. Mirhoseini M., Cayton M. M., *Revascularization of the Heart by Laser*, J Microsurg 2:253, June, 1981. The laser forms each channel by vaporizing a passageway completely through the wall of the heart. The relatively clean channel formed by the laser energy prevents the channel from healing over, and the channel either closes by clotting at the heart's outer surface, due to exposure to air, or manual pressure can be applied until bleeding from the channel ceases. However, if bleeding cannot be stopped, or if bleeding resumes at a later time, the patient may require surgery or may die.

Generally, it is desired that the channels be made primarily within the heart's inner surface (endocardium) since the endocardium has a greater need of an alternative supply of blood than the heart's outer surface (epicardium). It would be desirable not to create too large a channel through the epicardium because the channel must clot and/or heal at the heart's surface to prevent copious blood loss due to the forceful pumping action of the heart. It would be desirable to produce a channel which is widest at the point the channel exits the inner surface of the heart chamber, admitting a larger a volume of blood and being less susceptible to clotting or healing.

The current laser devices used to perform transmyocardial revascularization are inefficient at creating desirably shaped channels within the endocardium. For instance, a high power (i.e., 1,000 watt) carbon dioxide laser, whose beam is focused at the heart's surface, can make a channel completely through the heart wall in one shot in approximately 50 milliseconds, during diastole, when the heart is momentarily at rest. The channel, however, is usually wider in the epicardium than in the endocardium, making clotting or healing at the heart's outer surface less secure and making closure at the heart's inner surface more likely.

The prior art also uses several mirrors to reflect carbon dioxide laser energy toward the tissue to be vaporized. Maintaining the proper alignment of these mirrors at all times, however, is difficult and inconvenient for the operator.

Further, the use of less powerful lasers whose energy can be transmitted through optical fibers, such as argon-ion have also been proposed. Lee G. et al., Effects of Laser Irradiation Delivered by Flexible Fiberoptic System on the Left Ventricular internal Myocardium, Am Heart J., September, 1983. However, if the laser energy is applied to make the channel completely through the heart wall, the laser must be operated for a longer period of time than if it were used only to form a channel through the endocardium. If the procedure cannot be completed during diastole, within approximately 0.6 seconds at a heart rate of 60 beats per minute, between heartbeats when the heart's electrical activity is minimal, a life threatening arrhythmia may result, and damage to the heart muscle during its compression may occur.

The present invention provides an improved device and procedure which overcomes the above-discussed problems by combining mechanical energy with laser energy and, after a needle encasing the distal end of the optical fiber has initially penetrated a first portion of the tissue, enabling the laser energy to be emitted directly onto the tissue to be treated, where treating the tissue includes vaporization, and may include vascular tissue.

SUMMARY OF THE INVENTION

The present invention provides a device and procedure for utilizing mechanical energy to initially create a passageway or channel into the epicardium, which seals more quickly and dependably than a laser created channel, and avoids coagulating the passageway. The present invention further permits the delivery of laser energy, from either the outside of the heart or from the inside of the left ventricle of the heart, onto the myocardial and endocardial tissue to be vaporized so as to form a channel into the heart chamber.

The device embodying the present invention is especially suitable for use in medical applications for delivering laser energy to a selected tissue site at a controlled rate in a uniform manner, so the depth of coagulation surrounding the channel can be controlled as desired. In addition, the present device reduces the amount of laser energy required to form a channel, as initial penetration of the epicardium is achieved by mechanical means. Furthermore, the present device allows formation of uniformly or otherwise desirably shaped channels between heartbeats in a periodically moving structure such as a human heart.

The device embodying the present invention is particularly suited to creating a partial channel or pocket in the myocardium. It is contemplated that a therapeutic agent, such as an angiogenic growth factor or other therapeutic agent, or a gene coding for such a growth factor or other therapeutic agent, can be deposited into the channel, partial channel or pocket, while minimizing the risk of the therapeutic agent being expelled from its desired location in the myocardium into the pericardial sack or the blood in the heart chamber.

The preferred embodiment of the present invention includes a housing, a hollow guide attached to the housing either fixedly or removably, and an optical fiber-containing needle, surrounded by an inner catheter in fluid communication with a source of a therapeutic agent at its proximal end and in fluid communication with the needle at its distal end, which are received within a through bore of the hollow guide. An actuator means is provided to reciprocally extend the optical fiber/needle assembly from the hollow guide through the outer or inner layer of heart tissue without lasing, and then through the middle layer of tissue where a pocket is to be formed. The pocket is formed by energizing a suitable laser source and passing a laser beam from the source through the optical fiber into the tissue, as the needle advances a desired distance within the middle layer of the tissue, preferably within the myocardium, as governed by a needle control device. As the fiber/needle assembly is withdrawn, without lasing, from the middle portion of the tissue, the therapeutic agent or growth factor may be deposited in the pocket created by the energy emission.

The beams of certain pulsed lasers, such as $CO_2$ and Holmium:YAG lasers, are highly absorbed by water, and the beams of the excimer laser is highly absorbed by protein bands, and cause steam or heated gas bubbles to form and collapse after each pulse, resulting in an acoustic shock. Since endogenous (naturally occurring) growth factors are released by pressure medicated or hyproxic reaction, the acoustic shock caused by the pulsed lasers is thought to contribute to the angiogenesis in the area surrounding the channels.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same.

FIG. 9 is a partial enlarged cross-sectional side view of the device shown in FIG. 7 with the door open and, depicted in phantom, with the door closed;

FIG. 10 is a cross-sectional end view of the sleeve within the device taken along line 10—10 of FIG. 9 with the needle removed;

FIGS. 15A–15B each depict a cross-sectional side view of various disposable fiber and needle configurations for use with the device of FIG. 14;

FIG. 16 is a cross-sectional side view of another device in accordance with the present invention wherein the device is actuated by using compressed air;

FIG. 17 is a cross-sectional side view of yet another embodiment of the present invention;

FIG. 26 depicts the handpiece of FIG. 18 pressed against a heart wall with the needle puncturing through the heart;

FIG. 27 is a cross-sectional view of another handpiece in accordance with the present invention wherein the needle collar is secured to the handpiece housing;

FIG. 28 is a cross-sectional view of yet another handpiece having the needle collar detachably secured to the handpiece and curved at an angle of approximately thirty (30) degrees;

FIG. 29 is a further cross-sectional view of a handpiece with the needle collar detachably attached to the handpiece and curved at an angle of approximately ninety (90) degrees;

FIG. 32 is a partial enlarged cross-sectional side view of the device shown in FIG. 30 with the door open and, depicted in phantom, with the door closed;

FIG. 33 is a cross-sectional end view of the sleeve within the device taken along line 33—33 of FIG. 32 with the needle removed;

FIG. 34 is a cross-sectional top view of the device depicted in FIGS. 30–33;

FIG. 35 is a cross-sectional top view of another device in accordance with the present invention;

FIG. 47 is a touch-screen display provided by the external actuator of FIG. 44;

FIG. 50 is a cross-sectional view of yet another handpiece having the needle collar detachably secured to the handpiece and curved at an angle of approximately thirty (30) degrees;

FIG. 51 is a further cross-sectional view of a handpiece with the needle collar detachably attached to the handpiece and curved at an angle of approximately ninety (90) degrees;

FIG. 56 is a cross sectional view of an alternative embodiment of the device of FIG. 55 for use with the present invention wherein several fluid channels are in fluid communication with the lumen of the inner catheter or tubing, this embodiment having the optical fiber fixed within the bore of the needle and surrounded by either a buffer or jacket;

FIG. 57 is a cross-sectional view of another embodiment of the device of FIG. 55 for use with the present invention depicting an optical fiber covered by a jacket, and fluid communication channels being interspersed between flanges on the inner surface of the bore of the needle to fix the optical fiber in place; and FIG. 58 is a cross-sectional view of another embodiment of the device similar to that depicted in FIG. 57, depicting a channel within the bore of the needle and side ports to allow the drug or agent to be dispensed, the distal end of the optical fiber being surrounded by a jacket that allows the optical fiber to be fixed within the bore of the needle.

DISCLOSURE OF THE PREFERRED EMBODIMENTS

The present invention provides a surgical device for forming a channel by first utilizing mechanical energy to partially create a channel into selected tissue to be treated, which includes but is not limited to vascularization, and utilizing laser energy, emitted directly onto the tissue to be vaporized, to create the remainder of the channel. The device includes a needle having a bore with an opening in communication with the bore. The needle is mechanically or manually advanced into the middle layer to make the first portion of the channel in the tissue. Mounted within the bore is an optical fiber for emitting the laser energy to form the remainder of the channel in the tissue to be treated.

While this invention is susceptible of embodiments in many different forms, this specification and the accompanying drawings disclose only some specific forms as examples of the invention. The invention is not intended to be limited to the embodiments so described, however. The scope of the invention is pointed out in the appended claims.

Figure 1:
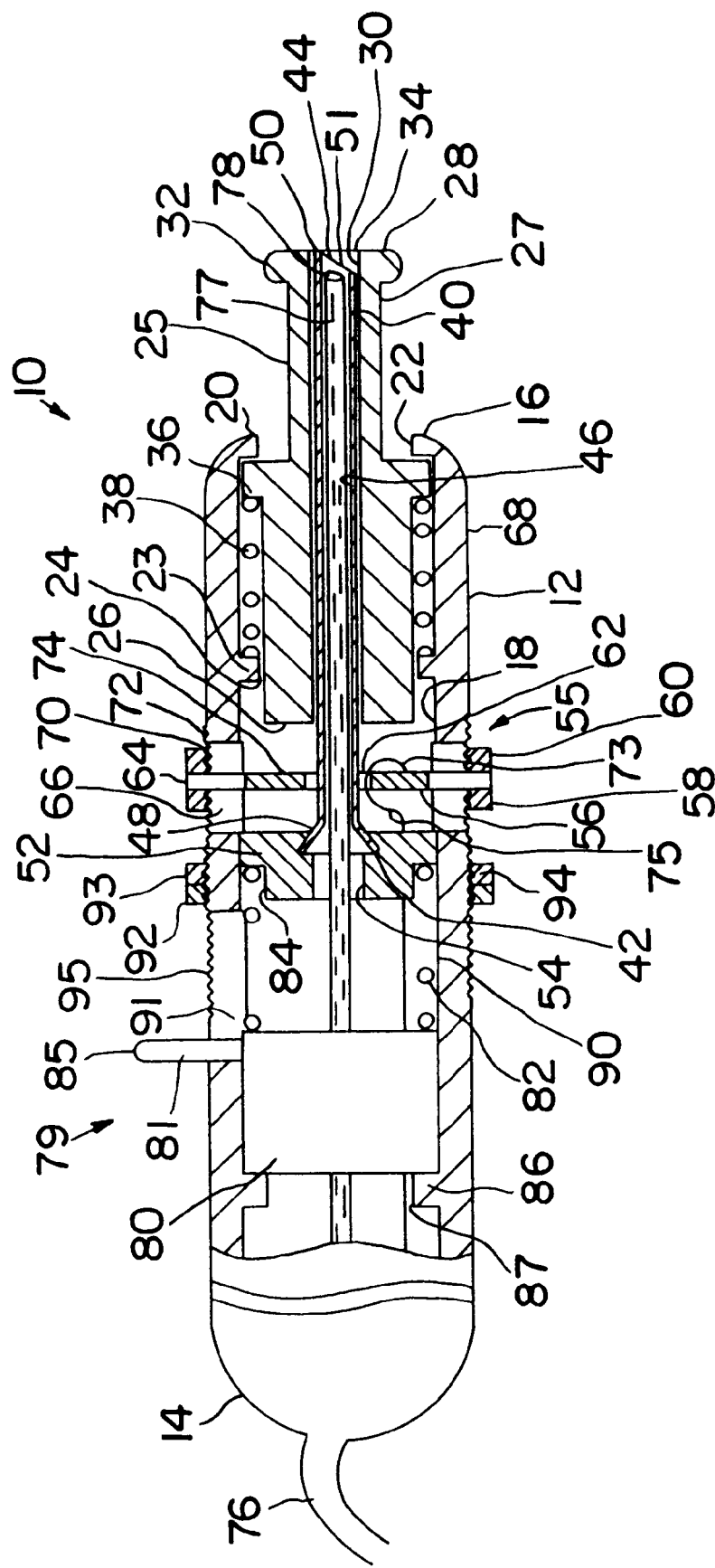
FIG. 1 is a partial cross-sectional view of a device in accordance with the present invention.

Referring to FIG. 1, a partial cross-sectional view of a device 10 in accordance with the present invention is shown. The device 10 includes a cylindrical housing 12 having a first end 14 and a tapered second end 16 with an elongated cavity 18 extending therebetween. Protruding from the tapered second end 16 and within the housing cavity 18 is a shoulder 20. The shoulder 20 is ring shaped with a circular aperture 22 in communication with the housing cavity 18.

Also extending from the housing 12 and within the housing cavity 18 is an annular abutment 23. The abutment 23 is located near the housing second end 16 and has a circular aperture 24 located at its center.

Mounted within the housing cavity 18 is a hollow needle collar or guide 25 having a neck 27. The needle collar 25 is generally cylindrical in shape with an inner end 26, an outer end 28, and a bore 30 extending therebetween. The neck portion 27 of the needle collar 25 begins generally between the inner end 26 and the outer end 28 of the needle collar and extends to the outer end 28. The neck portion 27 has a smaller outer diameter than the rest of the needle collar 25.

Furthermore, the inner end 26 of the needle collar 25 extends past the aperture 24 in the housing abutment 23. Likewise, the outer end 28 of the needle collar 25 protrudes from the aperture 22 in the housing 12 and has a rounded flange 32 extending around its periphery. The rounded flange 32 results in the outer end 28 of the needle collar 25 having a flat disk shaped surface with the bore aperture 34 being located in the center.

Also extending around the needle collar 25 is a retaining ring 36. The retaining ring 36 is located between the inner end 26 and the outer end 28 of the needle collar 25 and is positioned within the housing cavity 18 between abutment 23 and shoulder 20.

Similarly, located between housing abutment 23 and the needle collar ring 36 on guide 25 is a first coiled spring 38. The coiled spring 38 wraps around the needle collar guide 25 and biases the retaining ring 36 against the housing shoulder 20 and upon compression as collar guide 25 is actuated exposes the needle 40 together with a preferably 500–1000 micron core optical fiber 77 positioned therewithin.

Slidably mounted within the needle collar bore 30 is a needle 40. The needle 40 is generally tubular in construction with a proximal end 42, a distal end 44, and a bore 46 defined therebetween. The proximal end 42 of the needle 40 may be welded or otherwise attached to wall 52 or may be flared outwardly to form a funnel 48 about which the wall may be molded. Conversely, the distal end 44 of the needle 40 is angled to form a sharp point 50 and has a bevel opening 51 in communication with the bore 46.

As shown in FIG. 1, the distal end 44 of the needle 40 remains within the collar or guide 25, but is juxtaposed to the outer end 28 of the collar. Conversely, the proximal end 42 of the needle 40 extends from the inner end 26 of the needle collar or guide 25 and into the housing cavity 18.

The wall 52 within the housing cavity 18 has a shape similar to that of a donut with a hole 54 extending through its center. The wall 52 can be made of metal or a material such as epoxy and is secured to both the housing 12 and the needle 40. Thus, the needle 40 is held by the wall 52 in a fixed position relative to the housing 12. Furthermore, as shown in FIG. 1, the open distal end of needle 40 creates an access passage for the optical fiber 77 into the needle bore 46.

Located between the wall 52 and the inner end 26 of the collar 25 is a needle adjustment means 55 for selecting a desired needle penetration depth beyond guide 25 and within tissue. In FIG. 1, the needle adjustment means 55 is shown to consist of a first movable partition 56 and two locking rings 58,60. The movable partition 56 is generally shaped like a flat washer with a hole 62 in its center and the needle 40 passing therethrough.

Radially extending from the periphery of the movable partition 56 are a plurality of support beams 64. Associated with each support beam 64 is an elongated channel 66 which extends through the housing 12 and between the wall 52 and the inner end 26 of the collar 25. Correspondingly, each channel 66 allows its associated support beam 64 to advance from the housing cavity 18 and protrude from the outside 68 of the housing 12.

The distal end of each support beam 64 protruding from the housing 12 is abutted on both sides by locking rings 58 and 60. Each locking ring 58,60 has a threaded surface which mates with complementary threads 72 located on the outside 68 of the housing 12 and about the channels 66. Thus, rotating the locking rings 58,60 causes them to move along the outside 68 of the housing 12.

Correspondingly, the first partition 56 can be moved within the housing cavity 18 by moving the rings 58,60 on the outside 68 of the housing 12. Once the partition 56 is moved to the desired location within the cavity 18, the partition is locked into place by rotating the locking rings 58,60 in opposite directions relative to each other such that they press against the support beams 64.

Mounted onto the movable partition 56 is an electrical switch 73. The switch 73 is mounted on the surface 74 of the movable partition 56 which faces the inner end 26 of the needle collar 25. The switch 73 provides a means for indicating when the desired needle penetration depth has been acquired. Correspondingly, the switch 73 is activated only when the inner end 26 of the needle collar 25 abuts against the switch.

Attached to the switch 73 is an electrical lead 75. The lead 75 provides for the transmission of signals to indicate whether the switch 73 has been activated. The electrical lead extends from the switch 73, through the hole 62 in the movable partition, and into the wall 52. The electrical lead then continues through the wall 52 and into the lead 76 extending from the housing 12. Electrical lead 75 extends to either the laser or the foot pedal switch of the laser.

Turning back to the needle 40, received within its bore 46 is an optical fiber 77. The fiber 77 is mounted within the device 10 such that the fiber can be extended from the distal end 44 of the needle 40, if desired. The optical fiber may have a thin polyamide buffer coating which allows both the fiber 77 and the needle 40 to have a small diameter.

As shown in FIG. 1, the distal end 78 of the fiber 77 is positioned such that it is located adjacent to the needle point 50 but does not protrude from the needle bore 46. Conversely, at the distal end 44 of the needle 40, the fiber 77 continues through the hole 54 in the wall 52 and into the housing cavity 18.

The portion of the fiber 77 projecting within the housing cavity 18 is connected to fiber driver means 79. In FIG. 1, the driver means 79 is shown to consist of a sleeve 80 with a lever 81. The sleeve 80 is generally cylindrical in shape and is slidably mounted within the housing cavity 18. The sleeve 80 clamps around the optical fiber 77 such that the optical path within the fiber is not obstructed. However, movement of the sleeve 80 within the housing cavity 18 results in the same movement in the fiber 77.

Located between the sleeve 80 and the wall 52 is a second coiled spring 82. The coiled spring 82 projects into a circular groove 84 around the peripheral of the wall 52 and biases the sleeve 80 against a sleeve stop abutment 86.

The stop abutment 86 protrudes from the housing 12 and within the housing cavity 18. The abutment 86 is generally annular with a circular aperture 87 located at its center.

The lever 81 extending from the sleeve 80 consists of an elongated beam member with a distal end 85. The distal end 85 of the lever 81 advances through an elongated channel 91 and protrudes from the outside 68 of the housing 12. The channel 91 in the housing 12 extends from the wall 52 and towards the first end 14 of the housing 12. The movement of the lever 81 within the channel 91 is bounded by the housing 12 on one end and a pair of locking rings 92 and 93 on the other.

Each locking ring 92,93 has a threaded surface 94 which mates with complementary threads 95 located on the outside 68 of the housing 12 and about the channel 91. Thus, rotating the locking rings 92,93 causes them to move along the outside 68 of the housing 12.

Correspondingly, the travel of the lever 81 within the channel 91 can be restricted by moving the rings 92,93 towards the first end 14 of the housing 12. Once the rings 92,93 are moved to the desired location, the rings can be locked into place by rotating the rings in opposite directions relative to each other such that they press against one another.

As indicated previously, prior to using the device 10 of FIG. 1, the needle adjustment means 55 and the actuator means 79 must be properly set such that the needle 40 and the fiber 77 will be exposed and penetrate into adjacent tissue to their desired respective depths. The needle adjustment means 55 is set by moving the partition 56 to the desired location within the housing cavity 18. The partition 56 is moved within the housing cavity 18 by releasing the locking rings 58 and 60 from against the support beams 64. Once the partition 56 is moved to the desired location within the housing cavity 18, the partition is locked into place by rotating the locking rings 58,60 in opposite directions relative to each other such that they press against the partition support beams 64.

The fiber driver means 79 is set in a similar manner to that of the needle adjustment means 55. Correspondingly, locking ring 92 is moved along the outside 68 of the housing 12 by rotating the ring. Once the ring 92 is set to the desired position, the ring is held in position by firmly rotating ring 93 against locking ring 92 and then rotating the rings in opposite directions relative to each other such that they press against one another.

Figure 2:
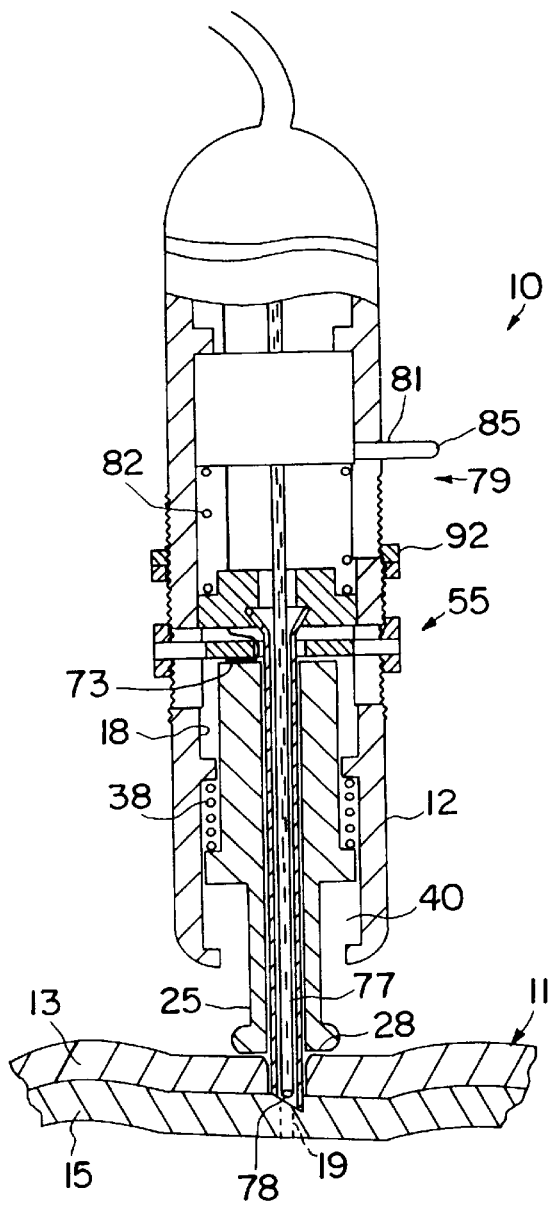
FIG. 2 is a partial cross-sectional view of the device of FIG. 1 pressed against the outer surface (epicardium) of a heart with the needle extending from the needle collar and into the epicardium.
Figure 3:
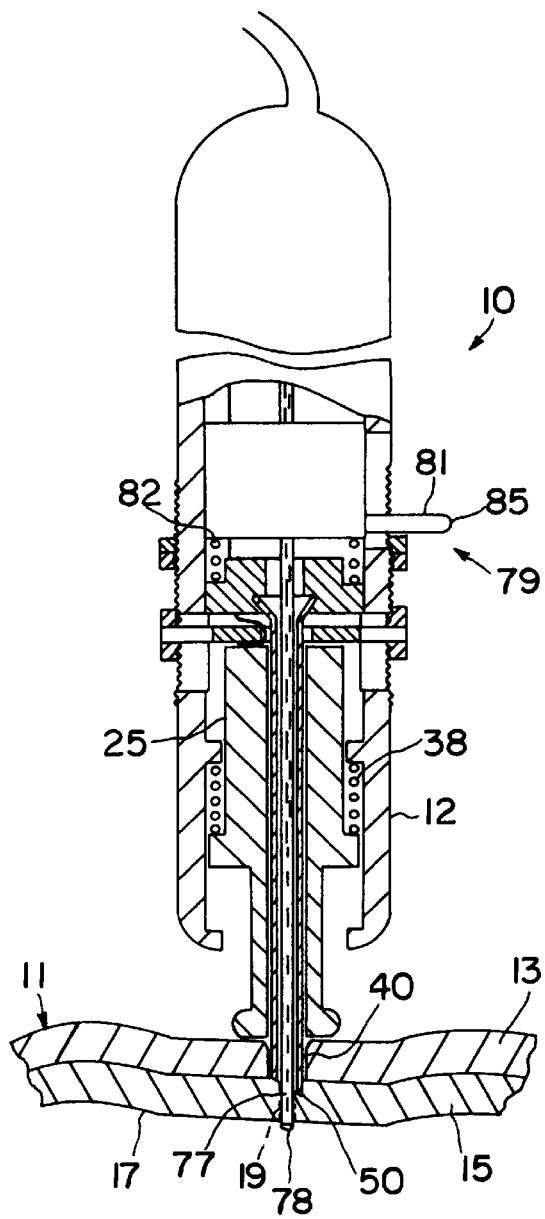
FIG. 3 is a partial cross-sectional view of the device the needle advances a desired distance within the ice of FIG. 2 with the fiber extending from the needle and into the inner layer (endocardium) of the heart.

Once the needle adjustment means 55 and the fiber driver means 79 are set to the desired depths, the device 10 can be used to perform surgical procedures such as transmyocardial revascularization. In such a procedure, the outer end 28 of the needle collar 25 is placed against the outer layer [i.e., epicardium] of a patient's heart. This is illustrated in FIGS. 2 and 3 where surgical device 10 is shown pressed against the epicardium 13 of a heart 11.

Once the surgical device 10 is positioned against the heart 11, advancing the housing 12 towards the heart causes the outer end 28 of the needle collar 25 to be urged against the epicardium 13 such that the needle collar retracts into the housing cavity 18 as the spring 38 compresses. As the needle collar 25 retracts into the housing cavity 18, the needle 40 extends from the needle collar and penetrates the epicardium 13. The needle 40 proceeds within the epicardium 13 until the inner end 26 of the needle collar 25 abuts against the switch 73. Abutment of the needle collar 25 against the switch 73 operates as a means for stopping both the retraction of the needle collar 25 within the housing cavity 18 and the penetration of the needle 40 into the epicardium 13. Furthermore, the switch 73 transmits a signal to the laser to indicate that the needle 40 has penetrated to the desired depth which was previously determined by setting the needle adjustment means 55 which enables the laser.

Once the needle 40 has penetrated to the desired depth within the epicardium 13, the fiber driver means 79 can be used to move the fiber 77 from the needle bore 46 further through the endocardium 15 of the heart 11. At the instant the fiber 77 proceeds to advance through the endocardium 15, the transmittal of laser energy within the fiber 77 commences and, if desired, continues until the fiber 77 is withdrawn completely from the endocardium 15. The laser energy may originate from a conventional laser which radiates laser energy into the fiber 77.

While energy from a Holmium:YAG laser or comparable laser at a wavelength of 1400 to 2200 micrometers is preferred, energy from an excimer laser (300 to 400 micrometers), argon laser (488–520 micrometers), KTP laser (532 micrometers, erbium laser (2940 micrometers), or any other source of laser energy able to be transmitted through optical fibers, pulsed, gated, or continuous wave may be utilized. The laser energy passes within the fiber 77 and is emitted from the distal end 78 of the fiber. A remote foot switch (not shown) connected to lead 75 may be provided to activate the laser if desired.

The fiber driver means 79 moves the fiber 77 from the needle and into the endocardium 15 by advancing the lever 81 towards the locking ring 92. Movement of the lever 81 causes the sleeve 80, along with the fiber 77, to proceed towards the heart 11. Furthermore, the spring 82 is compressed as the fiber 77 penetrates through the endocardium 15.

As the fiber 77 proceeds within the endocardium 15, the laser energy being emitted from the distal end 78 of the fiber vaporizes any tissue in the path of the fiber. The fiber 77 continues to penetrate through the endocardium 15 until the lever 81 abuts against ring 92. Abutment of the lever 81 against ring 92 serves as a means for indicating that the fiber 77 has penetrated to the desired depth which was previously determined by setting the actuator means 79, and thus fiber 77 is withdrawn from endocardium 15, while laser energy continues to be emitted therefrom, if desired. When fiber 77 is fully withdrawn to its initial position, the emission of laser energy ceases and the housing 12 is moved rearwardly, removing needle 40 from the epicardial tissue 13, and the needle collar is moved forward by spring 38 to its original position.

FIG. 3 provides a partial cross-sectional view of the device 10 of FIG. 2 with the fiber 77 penetrating to the desired depth such that the fiber 77 extends through the heart endocardium 15 and the inner wall 17 of the heart 11. The penetration of the fiber 77, along with the laser energy being emitted from the distal end 78 of the fiber, vaporizes tissue to form a channel 19. Confirmation that the fiber 77 has extended through the inner wall 17 of the heart 11 may be achieved by using a conventional ultrasound device to observe bubbles in the heart chamber caused by the emission of the laser energy or an acoustic sensor placed on the patient's carotid or other artery for detecting the sound of the bubbles.

Once the fiber 77 has extended through the heart inner wall 17, the transmission of laser energy within the fiber may be terminated. However, in an alternative embodiment, the transmission of laser energy may be continued until the fiber 77 has been fully retracted from the endocardium 15.

Removal of the fiber 77 is accomplished by discontinuing the application of force against the lever 81 such that the spring 82 may incite the actuator means 79 to withdraw the fiber 77 from the endocardium 131. The discontinuation of force allows the spring 82 to expand and cause the sleeve 80, along with the fiber 77, to move away from the heart 11. Retraction of the fiber 77 from within the endocardium 17 may also be assisted by applying a force away from locking ring 92 and against the lever 81.

The retraction of the fiber 77 from the newly formed channel 19 in the endocardium 15 allows blood to enter the channel from the inside of the heart 11. Once the distal end 78 of the fiber 77 is moved within the needle 40, the needle may be removed from the epicardium by moving housing 12 rearwardly. However, if laser energy was being transmitted during the withdraw of the fiber 77 from the endocardium 15, then the energy transmission may be terminated before needle 40 begins to withdraw from the epicardium 13. The determination of whether to continue the transmission of laser energy as the fiber 77 is removed from the epicardium 15 depends on if it is desirable to produce a coagulation zone about the channel through the patent's epicardium.

The needle 40 may be removed from the epicardium 13 by moving the housing 12 away from the heart 11 which causes the needle collar 25 to extend from the housing cavity 18 as the spring 38 decompresses and the switch 73 becomes deactivated. The deactivation signal transmitted by the switch 73 can be used as a means for switching the laser energy off. The device 10 can then be moved to another position on the heart's surface and the procedure repeated.

When used on a beating heart, it is desired that the above procedure take only 0.1 to 0.7 seconds, preferably 0.3 to 0.6 seconds, from the time the needle 40 begins to extend from the needle collar 25, the channel 19 is formed, and the needle is fully retracted back into the needle collar. The above procedure may be conducted over a longer period of time in an arrested heart, for example, during coronary bypass graft surgery, or in a beating heart during several beats, if desired. In any case, advancing the device 10 mechanically at a selected rate at a desired energy level enables the channels to be made with a uniform diameter and depth of coagulation zone surrounding the channel.

Figure 4:
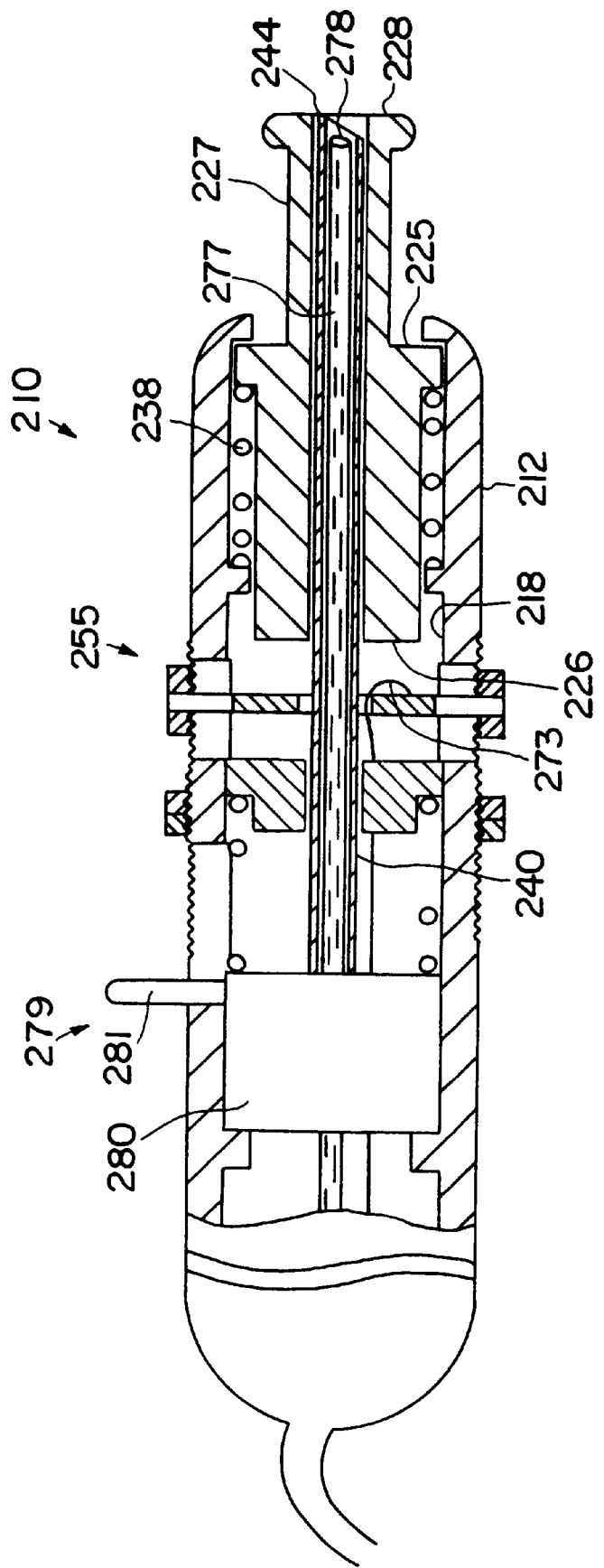
FIG. 4 is a partial cross-sectional view of another embodiment of a device in accordance with the present invention.

In another preferred embodiment the needle and the optical fiber advance together through both the epicardium and the endocardium. Turning to FIG. 4, a partial cross-sectional view of a device 210 for performing such a procedure is provided. The device 210 is similar to the device 10 depicted in FIGS. 1–3. Correspondingly, the last two digits in the 200 series of numerals depicted in FIG. 4 are connected to elements which have the same function and/or structure as those described with regard to FIGS. 1–3. In FIG. 4, however, the needle 240 is attached to the sleeve 280 which results in the optical fiber 277 being held in a fixed position relative to the needle 277.

The device 210 operates similarly to the device 10 depicted in FIGS. 1–3. Thus, prior to using the device 210, the needle adjustment means 255 and the fiber driver means 279 must be properly set, or interlocked, such that the needle 240 and fiber 277 together will penetrate to the desired depth. Once the needle adjustment means 255 and the fiber driver means 279 are set to the desired depths, the device 210 can be used in a procedure similar to that discussed above.

Correspondingly, in a transmyocardial revascularization procedure, the outer end 228 of the needle collar 225 is placed against the epicardium of a heart. The device housing 212 is then advanced towards the heart such that the needle 240 proceeds within the epicardium until the inner end 226 of the needle collar 225 abuts against the switch 273. Abutment of the needle collar 225 against the switch 273 operates as a means for stopping the penetration of the needle 240 into the epicardium and cause the switch 273 to transmit a signal indicating that the needle 240 has penetrated to the desired depth.

Once the needle 240 has penetrated to the desired depth within the epicardium, the actuator means 279 is used to move the needle 240 and the fiber 277 an additional distance through the endocardium of the heart. However, before the needle 240 and fiber 277 proceed into the endocardium, the transmittal of laser energy within the fiber 277 may be commenced such that the energy is emitted from the distal end 278 of the fiber.

The actuator means 279 moves the needle 240 and the fiber 277 an addition distance such that the laser energy being emitted from the distal end 278 of the fiber vaporizes any endocardium tissue in the path of the needle and the fiber. Once the needle 240 and the fiber 277 have traveled through the endocardium and into the heart's chamber, the transmission of laser energy within the fiber may be terminated. However, in an alternative embodiment, the transmission of laser energy may be continued until the fiber 277 and the needle 240 have been retracted from the endocardium.

The fiber 277 and the needle 240 are removed from the endocardium by discontinuing the application of force against the lever 281. The retraction of the fiber 277 and the needle 240 from the newly formed channel in the endocardium allows blood to enter the channel from the inside of the heart. Furthermore, if laser energy was being transmitted during the withdrawal of the fiber 277 and the needle 240 from the endocardium, then the energy transmission may be terminated before the fiber and needle are withdrawn into the epicardium. However, the transmission of laser energy as the fiber 277 is removed from the epicardium may be continued, if desired, to produce a thin coagulation zone about the channel through the epicardium.

Consequently, the needle 240 and fiber 277 may be removed from the epicardium by moving the housing 212 away from the heart, which causes the inner end 226 of the needle collar 225 to extend from the housing cavity 218 as the spring 238 decompresses and the switch becomes deactivated. The signal that the switch has become deactivated can be used for an indication to turn the laser off.

The above transmyocardial revascularization procedures can be used on an arrested heart during coronary bypass surgery or other open chest procedure, or on a beating heart. If used on a beating heart it is desired that the diameter of the housing, or at least the neck and the outer end of the needle collar, have a diameter as small as possible so that the device can be inserted through a trocar puncture (i.e., first port) between the ribs. Preferably the diameter is in the range of about three to ten millimeters. More preferred, however, is a diameter of about four to about six millimeters.

In addition, as indicated above, the flange of the needle collar is rounded and the second end of the housing is tapered so that the device, or at least the needle collar, can be easily inserted through a puncture between the ribs of a patient, if so desired.

A thoracoscope may also be inserted through a second port to allow visualization of the positioning of the device against the heart. Furthermore, a third port may be used for inserting a blunt instrument to press against the heart if bleeding occurs at the puncture site.

In a further embodiment it is preferred that the outer end 228 is positioned against a chest wall instead of against the heart itself. This procedure is similar to that discussed above. However, in such a case it is preferred that the needle 240 be either 14-gauge needle with a 1000 micron fiber therewithin or a 16-gauge needle with a 600 micron fiber therewithin.

In performing the procedure, the outer end 228 of the needle collar 225 is placed against the chest wall. The device housing 212 is pressed against the chest such that the needle 240 is inserted between the ribs with the distal tip 244 of the needle not quite contacting the heart when the heart is fully expanded in diastole. The positioning of the needle tip 244 relative to the heart can be observed by a thoracoscope inserted through a second port.

The needle is then advanced into the epicardium until the inner end 226 of the needle collar abuts against the switch 273. Once the needle 240 has penetrated to the desired depth within the epicardium, the actuator means 279 is used to move the needle 240 and the fiber 277 an addition distance within the endocardium of the heart. Furthermore, the transmittal of laser energy from the distal end 278 of the fiber 277 occurs as penetration of the endocardium is begun.

Once the needle 240 and the fiber 277 have penetrated through the endocardium and into the heart chamber, the transmission of laser energy within the fiber may be terminated. However, in an alternative embodiment, the transmission of laser energy may be continued until the fiber 277 and the needle 240 have been retracted from the endocardium.

The fiber 277 and the needle 240 are removed from the endocardium by discontinuing the application of force against the lever 281. Furthermore, if laser energy was being transmitted during the withdraw of the fiber 277 and the needle 240 from the endocardium, then the energy transmission may be terminated before the fiber and needle enter the epicardium, unless it is desired that laser energy be continued through the epicardium. Finally, the needle 240 and fiber 277 are removed from the epicardium by moving the housing 212 away from the heart.

It is desired that the above procedure in the case of a beating heart take only 0.1 to 0.7 seconds, preferably 0.3 to 0.6 seconds, from the time the needle 240 first punctures the heart to the time the needle leaves the heart.

In another embodiment it may be desired to have a means for indicating when the needle has advanced a preselected distance into the chest wall.

Figure 5:
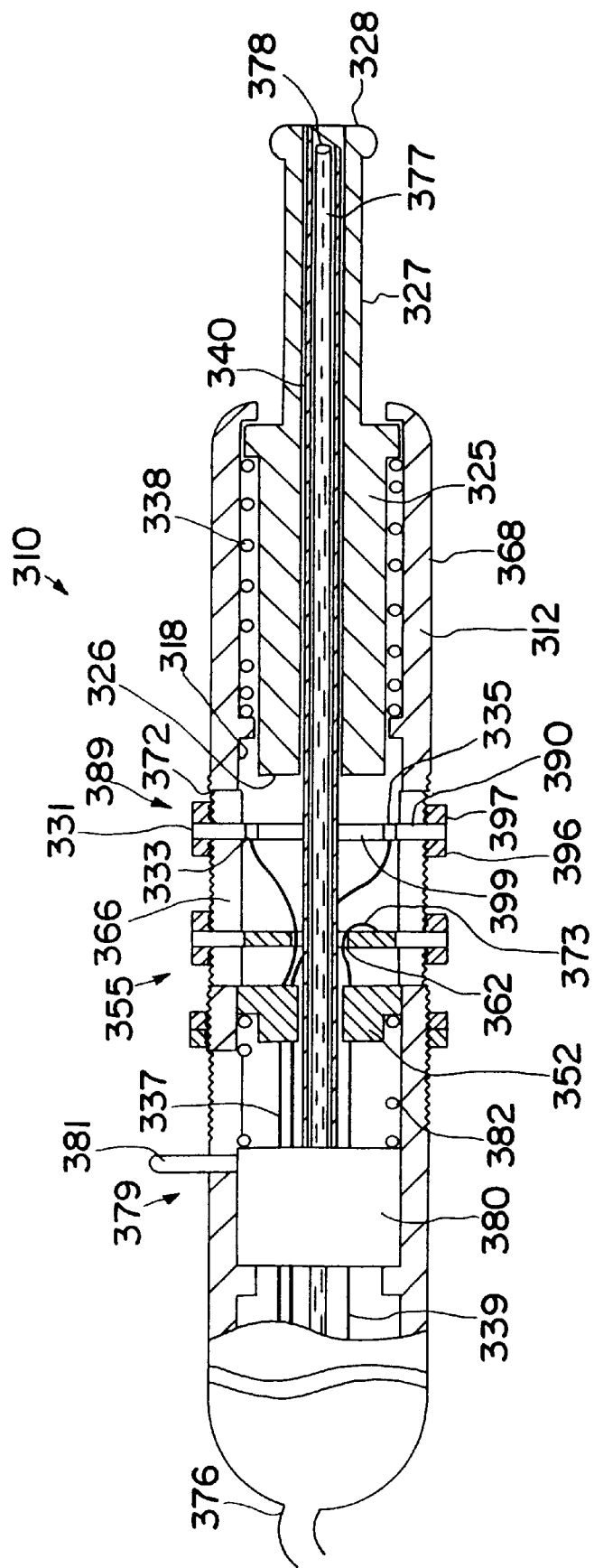
FIG. 5 is a partial cross-sectional view of yet another embodiment of a device in accordance with the present invention.

Turning to FIG. 5, a partial cross-sectional view of a device 310 for performing such a procedure is provided. The device 310 is similar to the device 210 depicted in FIG. 4. However, located between the needle adjustment means 355 and the inner end 326 of the collar 325 is an indicator means 389 for indicating the needle depth when the needle 340 has advanced a preselected distance from the outer end 328 of the collar 325 and thus into heart issue or the chest. In FIG. 5, the indicator means 389 is shown to have a second movable partition 390 and two locking rings 396,397. The movable partition 390 is generally shaped like a flat washer with an aperture 399 in its center and the needle 340 passing therethrough. The aperture 399 is large enough to allow the needle collar 325 to pass therethrough.

Radially extending from the periphery of the movable partition 390 are a plurality of support beams 331. Each support beam 331 is associated with the elongated channel 366 which extends through the housing 312 and between the wall 352 and the inner end 326 of the collar 325. Correspondingly, each channel 366 allows its associated support beam 331 to advance from the housing cavity 318 and protrude from the outside 368 of the housing 312.

The distal end of each support beam 331 protruding from the housing 312 is abutted on both sides by locking rings 396 and 397. Each locking ring 396,397 has a threaded surface which mates with the complementary threads 372 located on the outside 368 of the housing 312 and about the channels 366. Thus, rotating the locking rings 396,397 causes them to move along the outside 368 of the housing 312.

Correspondingly, the partition 390 can be moved within the housing cavity 318 by moving the rings 396,397 on the outside 368 of the housing 312. Once the partition 390 is moved to the desired location within the cavity 318, the partition is locked into place by rotating the locking rings 396,397 in opposite directions relative to each other such that they press against the support beams 331.

Mounted onto the movable partition 390 are two brush contacts 333,335. The contacts 333,335 are mounted on the movable partition 390 such that they protrude within the partition aperture 399. Therefore, the brush contacts 333,335 wipe against the needle collar 325 as the collar proceeds through the aperture 399.

In this embodiment, it is preferred that the needle collar 325 be constructed of a conductive material such that the needle collar provides a conductive path between the two brush contacts 333,335 as the collar proceeds through the aperture 399. Therefore, the brushes provide a means for indicating when the needle has reached a preselected depth because a conductive path is provided between the brushes 333,335 by the collar 325.

Attached to the contacts 333 and 335, respectively, are electrical wires 337 and 339. The wires 337,339 provide for the transmission of signals to determine whether the collar 325 is within the aperture 399 of the indicator means 389. The electrical wires extend from the brushes 333,335, through the hole 362 in the other moveable partition, and into the wall 352. The electrical wires then continue through the wall 352, the sleeve 380, and into the lead 376 extending from the housing 312.

The device 310 operates similarly to the device 210 depicted in FIG. 4. Thus, prior to using the device 310, the needle adjustment means 355 and the actuator means 379 must be properly set such that the needle 340 and the fiber 377 will penetrate to the desired depth. Furthermore, the indicator means 389 must be set by moving the partition 390 to the desired location within the housing cavity 318. The partition 390 is moved within the housing cavity 318 by releasing the locking rings 396 and 397 from against the support beams 331. Once the partition 390 is moved to the desired location within the housing cavity 318, the partition is locked into place by rotating the locking rings 396,397 in opposite directions relative to each other such that they press against the partition support beams 331.

Once the indicator means 389, the needle adjustment means 355, and the actuator means 379 are properly configured, the device 310 can be used in a procedure similar to that discussed above. Correspondingly, in a transmyocardial revascularization procedure, the outer end 328 of the needle collar 325 is placed against the chest wall. The device housing 312 is pressed against the chest such that the needle 340 is inserted between the ribs.

As the needle is inserted into the chest, the inner end 326 of the needle collar 325 advances into the partition aperture 399. Consequently, the brush contacts 333,335 wipe against the needle collar 325 as the collar proceeds through the aperture 399. Therefore, a electrical connection is formed between the brush contacts 333,335, by the needle collar 325, to indicate that the needle has protruded to the selected distance within the chest which was previously determined by the setting of the indictor means 389.

The needle is then advanced into the epicardium until the inner end 326 of the needle collar abuts against the switch 373. Once the needle 340 has penetrated to the desired depth within the epicardium, the actuator means 379 is used to move the needle 340 and the fiber 377 an addition distance into the endocardium of the heart. Furthermore, the transmittal of laser energy from the distal end 378 of the fiber 377 occurs as the endocardium is penetrated.

Once the needle 340 and the fiber 377 have penetrated through the endocardium and into the heart's chamber, the transmission of laser energy within the fiber may be terminated. However, in an alternative embodiment, the transmission of laser energy may be continued until the fiber 377 and the needle 340 have been retracted from the endocardium.

The fiber 377 and the needle 340 are removed from the endocardium by discontinuing the application of force against the lever 381. Furthermore, if laser energy was being transmitted during the withdraw of the fiber 377 and the needle 340 from the endocardium, then the energy transmission may be terminated before then fiber and needle are withdrawn from the epicardium. However, the transmission of laser energy may be continued through the epicardium if desired. Finally, the needle 340 and fiber 377 are removed from the epicardium by moving the housing 312 away from the heart.

Figure 6A:
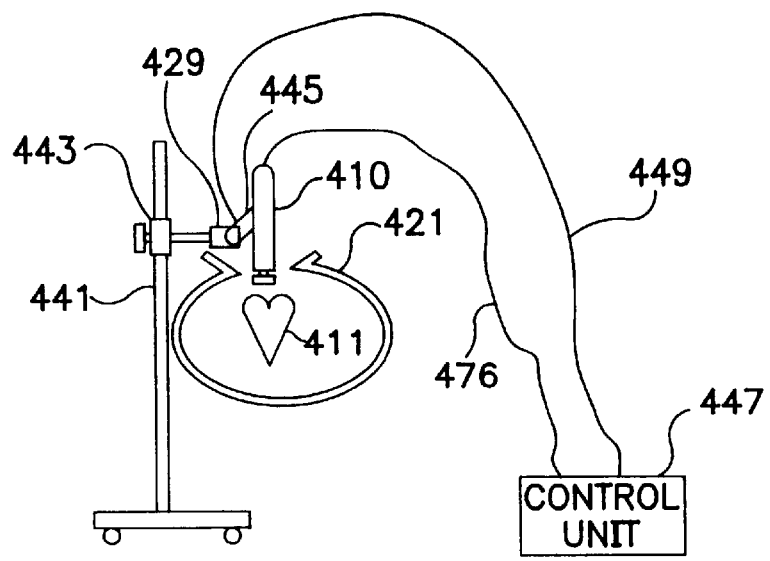
FIG. 6A is a schematic view of a mechanism for use with any of the device embodiments depicted in FIGS. 1–5 in an open chest procedure.
Figure 6B:
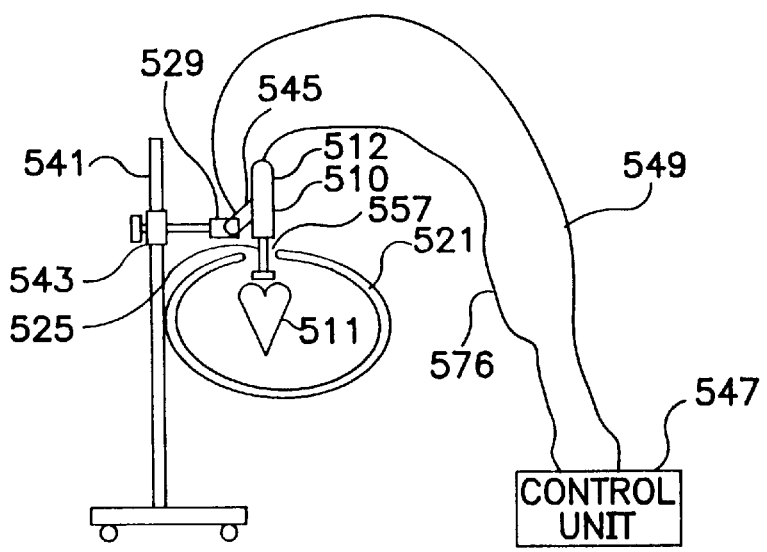
FIG. 6B is a schematic view of a mechanism for use with any of the device embodiments depicted in FIGS. 1–5 in a closed chest procedure.
Figure 6C:
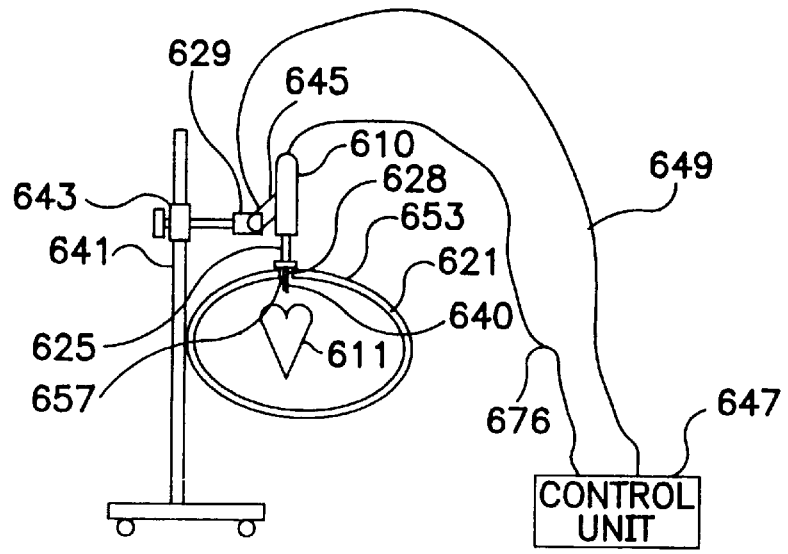
FIG. 6C is a schematic view of a mechanism for used with any of the device embodiments depicted in FIGS. 1–5 in a closed chest procedure.
Figure 7:
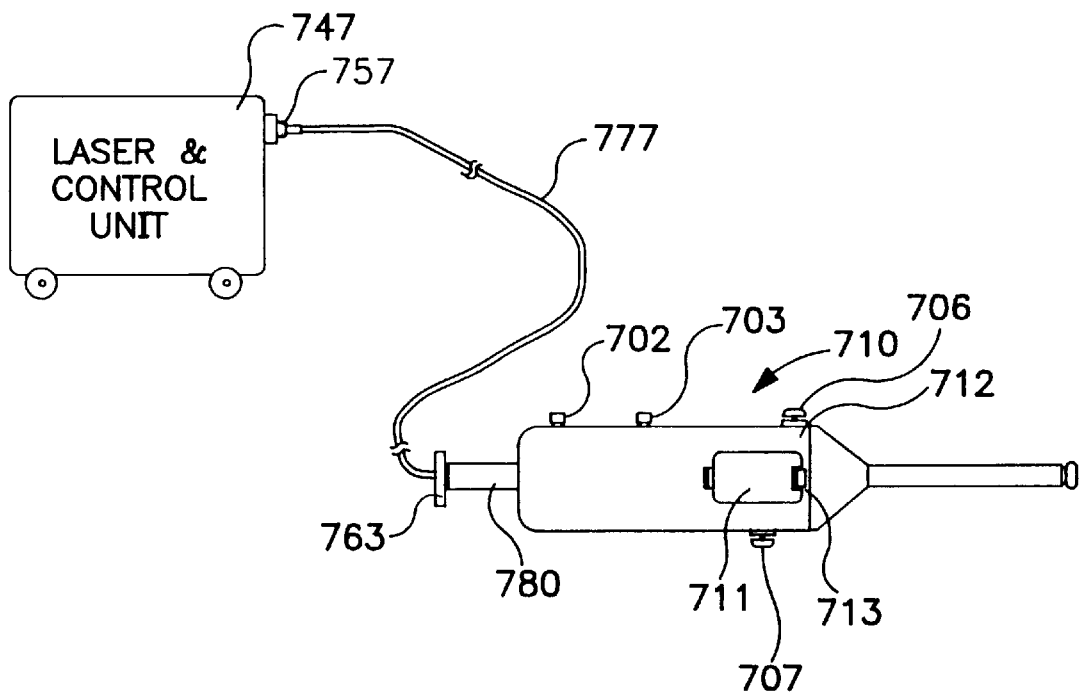
FIG. 7 is a perspective top view of another device, connected to a laser energy source, that embodies the present invention and includes a door for accessing a disposable needle.
Figure 8:
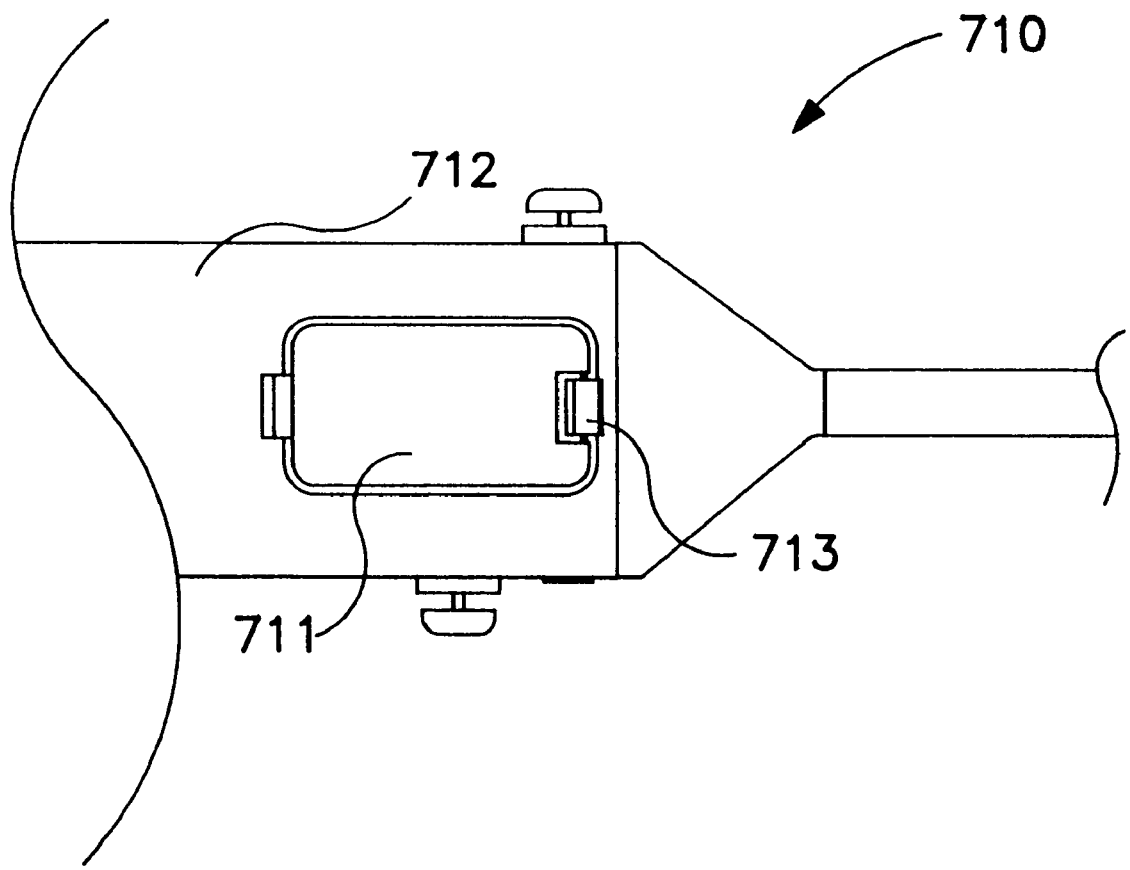
FIG. 8 is an enlarged partial top view of the device of FIG. 7 illustrating the door to access the disposable needle.

It should be noted that in all of the embodiments depicted above, the devices can be manually applied or a mechanism can be attached for operating the devices. FIGS. 6A, 6B, and 6C provide schematic views of various mechanisms for operating a device.

In FIG. 6A, the device 410 may be in accordance with any of the embodiments depicted above. The mechanism 429 is mounted on a movable platform 441 such as an I.V. pole or any other conventional structure. The mechanism 429 is adjustable connected to the pole 441, by a clamp 443, such that the mechanism is positioned at a desired height over the patient's heart 411 with the chest opened.

The mechanism 429 has an arm 445 connected directly to the device 410. The arm 445 may have air pistons, stepper motors or other devices for advancing the housing and/or fiber.

The lead 476 extending from the device 410, which contains the optical fiber and the device signal leads, is connected to the control unit 447. The control unit 447 receives position signals from the device 410 and, when commanded, transmits laser energy into the optical fiber.

It is preferred that the control unit 447 be capable of supplying laser energy at various selectable energy rates. Correspondingly, the uniform rate of penetration by the needle and/or fiber within the heart tissue correlates to the preselected laser energy rate such that, the higher the selected energy rate, the faster the penetration rate.

Accordingly, the control unit also has a wire harness 476 connected to the mechanism 429 for supplying power and controlling the advancement of the device housing and/or fiber.

Turning to FIG. 6B, another embodiment is depicted which is identical to that of FIG. 6A except that the mechanism 529 is positioned over a puncture 557 which provides access to the patient's heart 511. The puncture 557 is between the ribs of the patient and provides for the needle collar 525 to extend within the patient's chest 521 and abut against the outer surface of the heart 511. Preferably, the needle collar 525 is of sufficient length such that housing 512 remains outside of the patient's chest 521 as the needle and/or fiber are advanced into the heart 511 to form a channel.

FIG. 6C provides yet another embodiment that is similar to FIG. 6B except that the outer end 628 of the needle collar 625 abuts against the outside wall 653 of the patient's chest 621 with the needle 640 penetrating within the chest puncture 657.

In yet another embodiment, the mechanism within FIGS. 6A, 6B, or 6C can be attached to the device such that a single thrust of the arm towards the heart operates the device. For example, turning to FIGS. 5 and 6C, the arm 645 can be connected only to the lever 381 of the actuator means 379. Correspondingly, the movement of the arm 645 towards the heart 611 results in the outer end 628 of the needle collar 625 be pressed against the chest of a patient.

As the arm 645 continues to move towards the heart, the needle 340 advances within the chest puncture 657 and then into the heart since, in this embodiment, the needle collar spring 338 requires less force to compress than the actuator spring 338. Thus, the inner end 326 of the needle collar 325 moves until it abuts against the switch 373 and thus indicates that the needle 340 has penetrated to a desired depth in the heart.

Once the needle 340 has penetrated to the desired depth, the actuator means 379 moves both the needle 340 and the fiber 377 an additional distance within the heart as the spring 382 begins to compress and laser energy is emitted from the distal end 378 of the fiber.

The needle 340 and the fiber 377 are removed from the heart by moving the arm 645 away from the heart which first causes the needle and the fiber to retract from the endocardium and then from the epicardium because of the difference in the compression forces between springs 338 and 382.

It should be noted with regard to all of the embodiments depicted above that the laser can be activated by a foot-pedal, finger-button, or the "r" wave of the patient's ECG which supplies activation signals to the control unit. Likewise, the movement of the mechanism arm can be activated by a foot-pedal, finger-button, or the "r" wave of the patient's ECG.

In another embodiment, it may be advantageous to actuate the device by using compressed air. FIGS. 7–11 depict such an apparatus which also includes a disposable needle. Correspondingly, where appropriate, the last two digits in the 700 series of numerals depicted in FIGS. 7–11 are connected to elements which have the same function and/or structure as those described with regard to FIGS. 1, 4, 5, and 6.

The device 710 includes a generally rectangular door 711 that is hinged onto the device housing 712. The door 711 includes a conventional clip or latch 713, opposite the hinge, for securing the door 711 over an aperture which is in communication with the housing cavity 718.

As shown in FIG. 9, the door 711 also includes a resilient guide 721 which extends from the interior surface 729 of the door. The guide 721 includes a stem 741 which extends generally perpendicular from the door 711 with a foot 743 that outwardly projects from the distal end of the stem. Preferably, the foot 743 has an extended portion 745 that slopes away from the door interior 729 and is contoured to press against the needle as explained, in detail, below.

Figure 11:
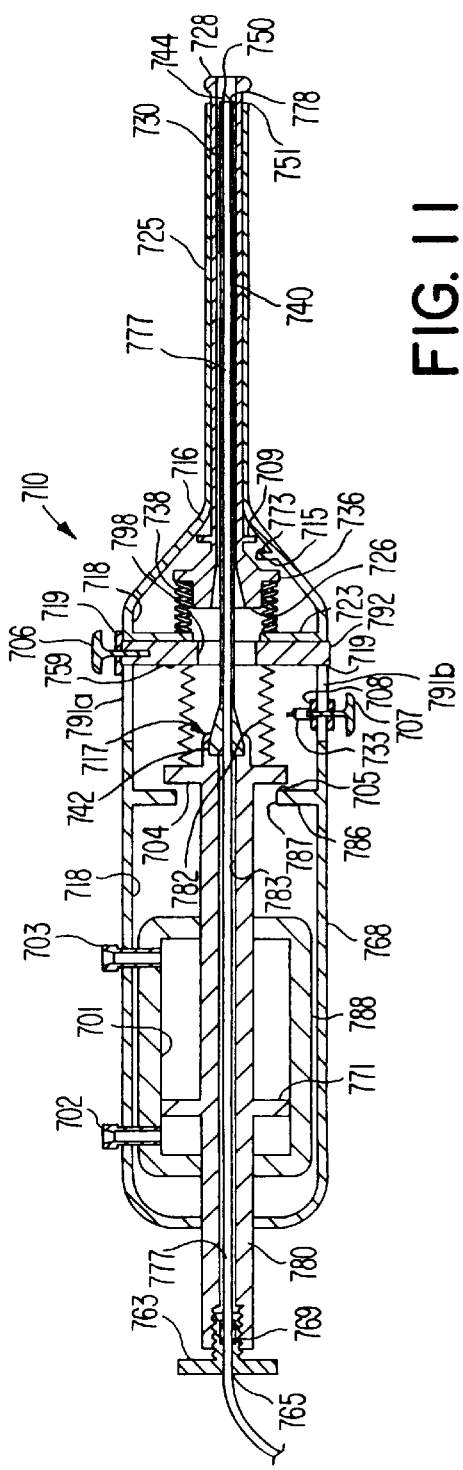
FIG. 11 is a cross-sectional top view of the device depicted in FIGS. 1–10.

FIGS. 9, 10, and 11 depict one end of the sleeve 780 within the device 710 having a socket or grip 717 for detachably connecting the sleeve 780 to the needle 740. The grip 717 includes a planar annular face 749 with an arcuate, generally semicircular, lip 753 perpendicularly projecting from the outer margin of the face. Preferably, the lip 753 is concave when view from the door 741 and has an inwardly sloped distal portion 761.

By placing the first end 742 of the needle 740 against sleeve face 749, the lip 753 adjoins against the outwardly flared proximal end 742 of the needle 740. Thus, the lip 753 receives and partially engages the needle 740.

When fiber 777 is not extending within the needle bore 746, the needle 740 is removed from the device 710 by opening the door 711 and extracting the needle. As the first end 742 of the needle 740 is pulled from the housing cavity 728, the second end 744 of the needle first vacates the needle collar bore 730 in addition to the device cavity 718.

Conversely, the needle 740 is inserted within the device 710 by opening the door 711 and inserting the second end 744 of the needle within the device cavity 728. Preferably, the needle collar bore opening within the device cavity 728 is funnel shaped for ease in inserting the needle 740 into the collar 725. The second end 744 of the needle 740 is advanced within the needle collar bore 730 until the first end 726 of the needle is allowed to adjoin against the face 749 of the sleeve 780.

Preferably, the inner diameter of the needle bore 746 has approximately a 1.5 to 2.0 millimeter diameter which allows for a 500 to 1000 micron core fiber to be positioned within the bore.

As shown in FIG. 11, sleeve 780 is longitudinally axially aligned and spaced from the needle collar 725. Accordingly, while inserting and removing the needle 740 from the device 710, the needle must be angled into the device cavity 718 between the sleeve 780 and needle collar 725. As such, it is preferred that the needle 740 allow for resilient flexing while it is both inserted and removed from the needle collar first end 726 within device 710.

As stated above, the semicircular lip 753 of grip 717 adjoins against the outwardly flared proximal end 742 of the needle 740 when the needle is installed within the device 710. The lip 753 and the guide foot 743 forms a socket 717 for coupling the needle 740 to the sleeve 780 by closing the door 741 such that the foot 743 of guide 721 adjoins against the flared portion 742 of the needle.

With the needle 740 secured by the grip 717 to sleeve 780, the sleeve face 749 pushes the needle second end 744 from the needle collar bore 730 when the sleeve is advanced towards the needle collar 725. Further, because the guide 721 is positionally fixed relative to the device housing 712 but the needle 740 is not, it is preferred that the extended portion 745 of foot 743 resiliently flex in order to allow the needle first end 742 to advance towards the needle collar 725 while the guide remains at its fixed position. Further, the length of the foot 745 should be greater than the distance traveled by the needle first end 726 so that a socket 717 is always provided for continuously securing the needle to the sleeve 780 as the needle 740 is advanced and retracted.

The fiber 777 is coupled by a conventional optical fiber connector 757 to a laser source 747 and attaches, via a threaded fiber lock 763, to the distal end of sleeve 780. The fiber 777 longitudinally extends through bore 783 in sleeve 780 and into needle bore 746. Preferably, the second end 778 of the fiber 777 is positioned within the needle bore 746 such that the fiber is located adjacent to the needle point 750, but does not protrude from the needle bore.

The threaded fiber lock 763 provides for selectably adjusting the distance between the fiber distal end 778 and the second end 744 of needle 740. The fiber lock 763 threadably engages the distal end of sleeve 780 and has an open bore 765 in communication with the sleeve bore 783.

The fiber lock 763 also includes a tubular compression fitting 769 positioned within the fiber lock bore 765. The fiber 777 extends through the fiber lock bore 765 and compression fitting 769. The fiber lock 763 secures the position of the fiber 777 within the needle bore 746 by screwing the fiber lock into the sleeve bore 783 such that the compression fitting 769 tightens around, and thus secures, the fiber. Accordingly, the distance between the fiber distal end 778 and the second end 744 of needle 740 is fixably selectable by loosening the compression fitting 769, moving the fiber 777 to the desired position, and tightening the compression fitting.

As shown in FIG. 11, radially outwardly extending from the sleeve 780 is a flange or piston 771. Preferably, the piston 771 and the sleeve 780 are of unitary construction.

The piston 771 is slidably positionable within an actuator device such as cylinder 788 which has a generally cylindrical chamber 701. The cylinder 788 is secured by conventional means to the housing 712 within cavity 718. The sleeve 780 slidably extends through the cylinder 788 with the piston 771 located in the chamber 701.

Attached to the cylinder 788 and extending from the outside of the housing 712 are tubular ports 702 and 703 which are in fluid communication with the cylinder chamber 701. The ports 702,703 are generally coupled at each longitudinal end of the cylinder chamber 701. The ports 702, 703 provide for a fluid medium, preferably air, to ingress and egress from the chamber 701.

Between the piston 771 and the sleeve grip face 717 is a shoulder flange 704 for limiting the travel of the sleeve 780 within the housing cavity 718. Preferably, the shoulder flange 704 and the sleeve 780 are of unitary construction with the shoulder flange radially outwardly extending from the sleeve 780.

The travel of the shoulder flange 704 within the housing cavity 718, and thus sleeve 780, is bounded by wall 786 and movable partition 792. Wall 786 generally radially inwardly extends from the housing 712 into cavity 718. The wall 786 only partially extends into the housing cavity 718 to form an aperture 787 having an inner diameter which is less than the outer diameter of the shoulder flange 704. Thus, the shoulder flange 704 cannot pass through the aperture 787 in wall 786.

Attached to the wall 786 proximate to aperture 787 and facing the shoulder flange 704 is switch 705 for indicating when the sleeve 780, and thus the needle 740, is retracted. Preferably, switch 705 is activated when it is abutted by shoulder flange 704.

Moveable partition 792 also radially inwardly extends within the housing cavity 718. An aperture 798 is located generally in the center of the partition 792 with the sleeve 780 passing therethrough. Further, radially extending from the periphery of the movable partition 792 are a plurality of support beams 719. Associated with each support beam 719 is an elongated channel 791a,b which extends through the housing 712 and between the wall 786 and annular abutment 723. Correspondingly, each channel 791a,b allows its associated support beam 719 to advance from the housing cavity 718 to a position generally flush with the outside 768 of the housing 712.

Attached to partition 792 is a locking member comprising a set screw 706 for adjustably fixing the moveable partition to the housing 712. Preferably, the set screw 706 is threadably secured to the movable partition 792 and extends from the partition, to the outside 768 of the housing 712, via elongated channel 791a. As such, the position of the partition 792 is adjusted by releasing set screw 706, moving the partition to the desired location within the housing cavity 718, and tightening the set screw.

Also attached to partition 792 proximate to aperture 798 and facing the shoulder flange 704 is switch 759 for indicating when the sleeve 780, and thus the needle 740, is fully extended from the device 710. Preferably, switch 759 is activated when it is abutted by shoulder flange 704.

Extending along elongated channel 791b is a set screw 707 and clamp assembly 708 for adjustable moving a sensor 733 within the housing cavity 718. The clamp assembly 708 abuts against both the inside 718 and the outside 768 of the housing 712 with the set screw 707 extending through the channel 791b and threadably secured to the clamp assembly.

Sensor 733 is attached to the clamp 708 within the housing cavity 718. The sensor 733 detects when the sleeve 780, and thus the needle 740, has traveled a predetermined fixed distance. As such, the sensor 733 projects a distance within the housing cavity 718 that is generally equal to the distance between the housing 712 and the periphery of shoulder flange 704.

The set screw 707 allows for both adjustably securing the clamp 708 to, and releasing it from, the housing 712. Correspondingly, positioning of the clamp 708 results in like placement of the sensor 733 within the housing cavity 718. The sensor 733 is activated, preferably, when it comes in contact with, or is brushed by, the shoulder flange 704.

Radially outwardly extending from the needle collar 725 and within the housing cavity 718 is a stop flange 709. Further, a post 715 extends within the housing cavity 718 to limit the travel of the needle collar 725 to between the post 715 and the tapered second end 716 of the housing 712.

Mounted on the distal end of post 715 and facing towards the stop flange 709 is switch 773 for detecting when the needle collar 725 has been pushed a fixed distance within the housing cavity 718.

As indicated above, before the device 710 is used for forming a channel within tissue, the distal end 778 of fiber 777 is inserted through the bore 765 of compression fitting 769. The fiber 777 proceeds through the fiber lock 763 and the sleeve bore 783 such that the fiber is finally positioned within the needle bore 746.

Preferably, the distal end 778 of the fiber 777 is positioned proximate to the needle opening 751. Fiber lock 763 is tightened to maintain the position of the distal end 778 of the fiber 777 relative to the needle opening 751.

In a procedure where the heart has been arrested, device 710 is preferably used with an excimer laser for controllably emitting substantially non-thermal laser energy from the distal end 778 of fiber 777. In a procedure where the heart is beating, a laser generating a greater amount of energy is desired.

Before use, the laser 747 is set to deliver a desired amount of energy. The laser 747 is enabled to generate laser energy by depressing a footswitch or the like. However, it is desired that no laser energy be transmitted into the fiber 777, and thus emitted from the fiber distal end 778, until sensor 733 is activated as explained, in detail, further herein.

Preferably, in a procedure where the heart has been arrested, device 710 is positioned by hand such that the second end 728 of the needle collar 725 evenly contacts the outer surface of the heart. The housing 712 of the device 710 is then manually pressed towards the heart such that the needle collar 725 retracts within the housing cavity 718 as springs 738 compress.

The advancement of the needle collar 725 into the housing cavity 718 is terminated by stop flange 709 abutting against, and thus activating, switch 773. Compressed air, provided by a conventional air pump (not shown), is injected into forward air inlet port 702 by the activation of switch 773. The compressed air enters the cylinder chamber 701 and forces against piston 771 such that the piston, and thus sleeve 780, are advanced towards partition 792 and springs 782 are compressed between flange 704 and partition 792. Preferably, the compressed air forces the sleeve 780 to advance at a preselected velocity of about one (1) to three (3) millimeters per second.

As the sleeve 780 advances, attached needle 740 and fiber 777 are advanced a desired distance, preferably approximately one third (⅓) of the way through the heart wall, when sensor 733 is activated by contacting with shoulder flange 704. The position of the sensor 733 is preset by using ultrasound imaging or the like to estimate the thickness of the heart wall.

Sensor 733 is activated when it comes in contact with the shoulder flange 704. In response to activation of sensor 733, the laser unit 747 transmits laser energy through fiber 777 which is emitted from the fiber distal end 778. The fiber 777 and the needle 740 continue to advance together, preferably, through the heart wall. As such, it is desired that the needle 740 and fiber 777 are capable of fully traversing through a heart wall having a thickness from about 1.5 to 3.5 centimeters and into the heart chamber by about 0.2 to 0.5 centimeters.

The needle 740 and fiber 777 pass through the heart wall at the chosen rate of speed until shoulder flange 704 contacts, and thus actives, reserving microswitch 759. The switch 759 is operably connected to the control unit 747 which detects when the switch has been activated. In response to the switch activation, the control unit 747 terminates the injection of air into forward air inlet port 702 and injects air into reverse air inlet port 703.

The compressed air enters the cylinder chamber 701 and forces against piston 771 such that the piston, and thus sleeve 780, are advanced away from partition 792 and springs 782 are allowed to decompress. As such, needle 740 and fiber 777 are withdrawn from the heart wall.

During the withdraw, shoulder flange 704 brushes against switch 733 which commands the control unit 747 to stop the transmission of laser energy through the fiber 777 and emanating from the fiber distal end 778.

The travel of the needle 740 and fiber 777 back into needle collar 725 is stopped when shoulder flange 704 adjoins against microswitch 705. Further, the control unit 747, which is operably connected to microswitch 705, stops the injection of air into reverse air inlet port 703 when the flange 704 adjoins against switch 705.

Device 710 is then lifted off the heart wall which results in the needle collar 725 resuming its original position wherein springs 738 resiliently press stop flange 709 against the tapered second end 716 of device housing 712. The device 710 is then repositioned to another location on the heart's surface and the channel making process is began again.

As will be appreciated by those skilled in the art, device 710 may be mechanically advanced by means other than an air piston, such as a stepper motor or other mechanical means known in the art. However, it is preferred that the rate of advancement be selectable by either mechanical means or by entering a selected rate into a computer/controller as described, in detail, below.

As known by those skilled in the art, conventional holmium lasers have a "ramp-up" time of up to 1 second or longer from the time the laser medium is stimulated to produce laser energy until the time when laser energy is actually provided. Thus, it is desired that if device 710 is used with a conventional holmium laser during surgery, then the delivery of laser energy into fiber 777 should be gated in the manner illustrated by FIG. 12 to allow the transfer of laser energy into the fiber as soon as commanded.

Figure 12:
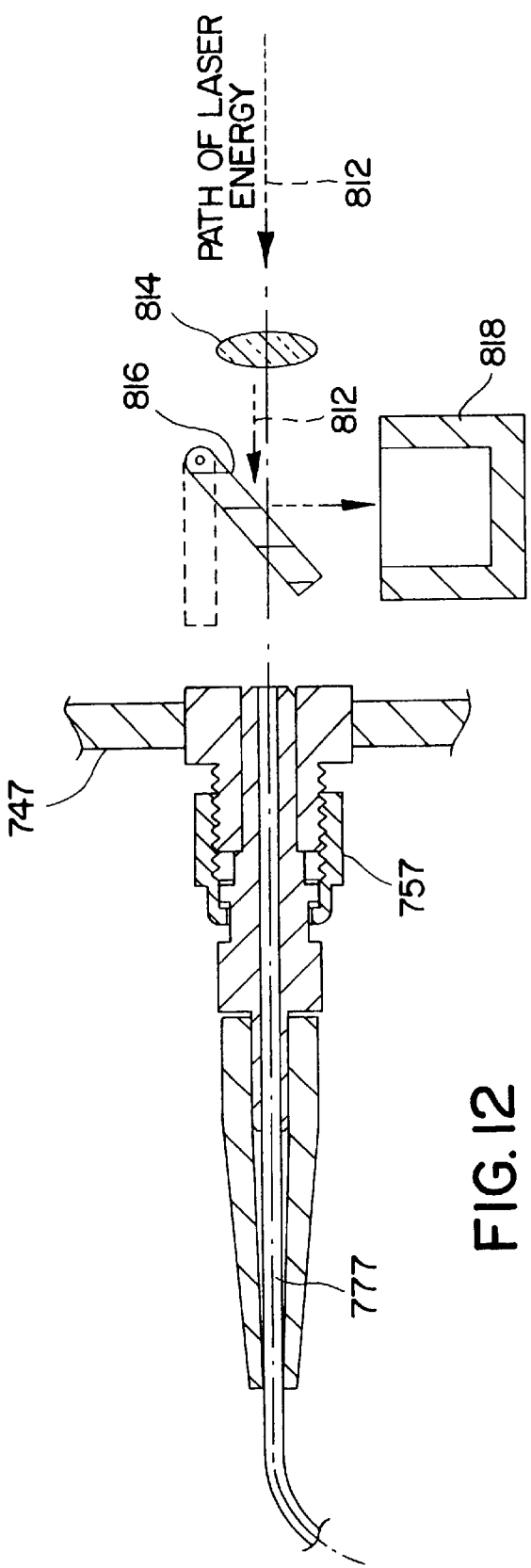
FIG. 12 is a partial schematic view of a method for gating laser energy by using a shutter having a first position, shown in phantom, and a second position, so that laser energy is continuously available for transmission without delay.

In FIG. 12, a beam 812 of laser energy is provided from a laser source 747. Such a beam of holmium laser energy can be provided by any conventional means known in the art such as that disclosed by U.S. Pat. No. 5,387,211, issued to Saadatmanesh et al., and incorporated herein by reference.

The laser energy beam 812 is received by a conventional focusing element such as a lens 814. The laser energy 812 passes through the lens and is focused onto the proximal end of the optical fiber 777.

Positioned between the fiber 777 and the lens 814 is a shutter or mirror 816 for intermittently redirecting the laser energy 812 passing through the lens 814. The mirror 816 is actuated by conventional means (not shown) to one of two positions.

In the first position, the mirror 816 is positioned out of the path of the laser energy so that the energy in received into fiber 777. Conversely, in the second position, the mirror 816 is positioned in the path of the laser energy to prevent the laser energy from being received by the fiber 777. In the second position, the laser energy is reflected by the mirror 816 into a conventional beam dump 818.

Preferably, the laser source is activated to emit laser energy by depressing a foot switch or other switching device. Activation of the laser source results in the laser energy beam 812 being provided after a sufficient "ramp-time" has elapsed and prior to the commencement of the channel making process. During this time, mirror 816 is in its second position, diverting the laser beam into the beam dump 818.

When the emission of laser energy into fiber 777 is desired, the mirror 816 moves into its first position and allows for the virtually undelayed delivery of laser energy into the fiber by moving the mirror 816 out of path of the laser energy. Thus, there is no need to wait for a prolonged "ramp-up" time because the laser energy is continuously available for transmission into the fiber 777.

Using the embodiment of FIG. 11 for illustrative purposes, when shoulder flange 704 activates microswitch 733, the mirror 816 is moved out of the beam path 812 of FIG. 12 and laser energy is transmitted through fiber 777. Conversely, when shoulder flange 704 contacts microswitch 759, the mirror 816 is moved into the beam path 812 which ceases the emission of laser energy into fiber 777.

In another embodiment, it is preferred that the shutter 816 consists of a beam dump such that, instead of reflecting laser energy, the shutter is capable of absorbing the laser energy when moved into the path of the laser energy.

The present invention can be used with the heart arrested or beating. If the heart is arrested, however, to assure uniformity of the channel and the surrounding coagulation zone, the elapsed time and the amount of laser energy emitted for each channel should be the same.

If the heart is beating, then it is desired that the device 710 be positioned so that the second end 728 of needle collar 725 is close to touching the surface of the heart when the heart is fully expanded. The device is then pressed against the heart such that springs 738 are compressed and stop flange 709 abuts against, and thus activates, switch 773. In response to switch 773 being activated, the control unit 747 is enabled to control the entry and withdraw of the needle 740 and fiber 777 within the heart.

It is desired that the control unit 747 monitor the heart by a conventional ECG sensing means to control the operation of the device 710 by using a signal recognition and timing procedure similar to that disclosed by U.S. Pat. No. 4,788,975, issued to Shturman et al., and incorporated herein by reference.

Preferably, the heart is in diastole when the device 710 forms a channel within the heart by injecting and withdrawing the needle 740. It is desired that the control unit 747 determine when to form the channel in the heart by interposing an appropriate delay time from the "r" wave of the patient's ECG, taking care to avoid activation of the device in the event of a premature ventricular contraction or any other unusual variation in heart rhythm.

Forming the channel when the heart is in diastole is preferred because, at that moment, the electrical activity of the heart is least affected by the trauma of the entry of the needle 740 and the emission of laser energy. Also, the heart chamber is full of blood and the heart wall is at its thinnest.

The present invention may be positioned within the chest by placing the device 710 through a puncture between the ribs of the patient. To ensure that the device 710 is properly positioned in relation to the heart, the surgeon can observe the second end 728 of the needle collar 725 by placing an endoscope through a second puncture within the chest wall and either between the ribs or from beneath the rib cage.

Figure 13:
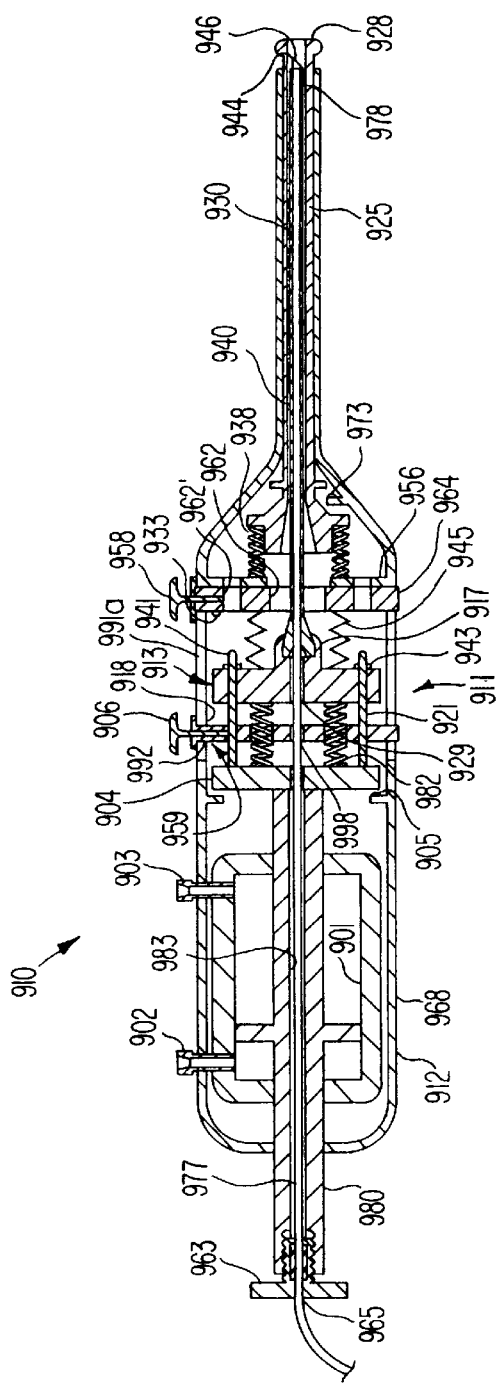
FIG. 13 is a cross-sectional top view of another device in accordance with the present invention.

FIG. 13 depicts an embodiment of the present invention which provides for advancing the needle and fiber together, and then advancing the distal end of the fiber from the needle. Correspondingly, where appropriate, the last two digits in the 900 series of numerals depicted in FIG. 13 are connected to elements which have the same function and/or structure as those described with regard to FIGS. 1, 4, 5, and 11.

In FIG. 13, the sleeve 980 has a compression coupling 911 extending from the shoulder flange 904. The compression coupling 911 includes a needle attachment 913 and springs 982.

The needle attachment 913 provides grip 917 mounted to a generally disk shaped retaining member 921. Preferably, the needle attachment 913 is of unitary construction with an open bore 929 that passes through the retaining member 921 and grip 917. The open bore 929 also is in longitudinal axial alignment with the needle collar bore 930 and the sleeve bore 983.

The grip 917 of the needle attachment 913 provides for removably connecting the needle 940 to the coupling. Further, the retaining member 921 allows for separately controlling the advancement of the needle 940 from that of the fiber 977.

The retaining member 921 is slidably mounted to guide posts 941 extending perpendicularly from the sleeve flange 904. The guide posts 941 slidably pass through the retaining member 921 with fasteners 943 attached to their distal ends to keep the retaining member from sliding off the posts.

Adjustably positionable between the retaining member 921 and the sleeve flange 904 is movable partition 992 for preselecting the desired depth that the needle 940 and the fiber 977 are to penetrate within tissue before the fiber distal end 978 advances from the needle bore 946. Aperture 998 is located generally in the center of the partition 992 with the fiber 977 passing therethrough.

Attached to partition 992 is set screw 906 for adjustably fixing the moveable partition to the housing 912. The set screw 706 extends from the partition 992, to the outside 968 of the housing 912, via elongated channel 991a. The position of the partition 992, and thus the distance the fiber 977 and needle 940 travel together, is preselected by securing the partition to the desired location within the housing cavity 718.

Mounted to the sleeve flange 904 and the retaining member 921 are springs 982 which unobtrusively pass through apertures in moveable partition 992. The springs 982 resiliently push retaining member 921 away from the sleeve flange 904 and against fasteners 943.

Also attached to partition 992 and facing shoulder flange 904 is switch 959 for indicating when the fiber distal end 978 is fully extended from the needle bore 946 by a preselected distance. The switch 959 is activated when it is abutted by shoulder flange 904 which also stops the extension of the fiber distal end 978 from the needle bore 946. As such, adjusting the position of the moveable partition 992 within housing cavity 918 establishes the distance that the fiber distal end 978 will extend from the bore 947.

Located between retaining member 921 and annular abutment 23 is a moveable partition 956 for selecting a desired needle penetration depth beyond the second end 928 of needle collar 925. The movable partition 956 is generally shaped like a flat washer with a hole 962 in its center and the needle 940 passing therethrough.

Radially extending from the periphery of the movable partition 956 are a plurality of support beams 964 which extend within channels 991. Each support beam is generally flush with the outside 968 of the housing 912.

Attached to moveable partition 956 is a locking member comprising set screw 958 for adjustably fixing the position of the partition. The set screw 958 is threadably secured to the movable partition 956 and extends onto the outside 968 of the housing 712. The position of the partition 956 is adjusted by releasing set screw 958, moving the partition to the desired location within the housing cavity 718, and tightening the set screw.

Mounted to the moveable partition 956 and the retaining member 921 are springs 945 which resiliently push the retaining member away from the partition. Preferably, however, springs 982 apply more force to press the retaining member 921 towards partition 956 than springs 945 apply to press the retaining member away from partition 956.

Extending through moveable partition 956 and annular abutment 923 are a plurality of bores 962' wherein each bore is in longitudinal axial alignment with one of the guide posts 941. The bores 962' allow the guide posts 941 to unobstructively pass through partition 956 and abutment 923 when the sleeve flange 904 is advanced towards the partition.

Mounted onto partition 956 and facing the retaining member 921 is switch 933 for detecting when the retaining member, and thus the needle 740, has traveled a predetermined fixed distance with the needle second end 944 protruding from the needle collar bore 930. Preferably, switch 933 is activated when it is abutted by retaining member 921.

As stated above, the device 910 of FIG. 13, is constructed so that needle 940 and fiber 977 may advanced together to a preselected distance within the epicardium of a heart. Thereafter, fiber 977, alone, may be advanced through the endocardium.

As the fiber 977 is withdrawn from the endocardium, laser energy is being emitted from the fiber distal end 978 until the fiber distal end is extracted back into the need bore 946. After which, the emission of laser energy ceases and needle 940 and fiber 977 are retracted together from the epicardium.

The sleeve 980, and thus the needle 940, is advanced by infusing air into forward air inlet 902. The air pushes the piston 971 and attached sleeve 980 such that springs 945 compress while springs 982 remain substantially decompressed.

As the sleeve 980 advances, the retaining member 921 abuts against switch 933 which stops the travel of the needle 940 from the needle collar bore 930. Further the laser unit is enabled to begin transmitting laser energy which is emitted from the distal end 978 of fiber 977.

As sleeve 980 continues to advance towards partition 956, fiber 977, which is affixed to the sleeve 980 by fiber lock 963, extends from the needle second end 944 as springs 982 begin to compress. The distance that the fiber 977 extends from the needle 940 is restricted by the sleeve flange 904 abutting against reversing microswitch 959.

Activation of switch 959 commands the control unit to discontinue injecting air into port 902 and begin pumping air into port 903. As such, the fiber distal end 978 is retracted back into the needle bore 946 and the needle 940 is retracted back into the needle collar bore 930.

In the device 910 of FIG. 13, the distance that needle 940 and fiber 977 advance substantially together is predetermined by adjustably positioning partition 956 within the housing 912 and tightening set screw 958. Further, the distance fiber 977 advances from the needle 940 is predetermined by positioning partition 992 within the housing 912 and tightening set screw 906.

Figure 14:
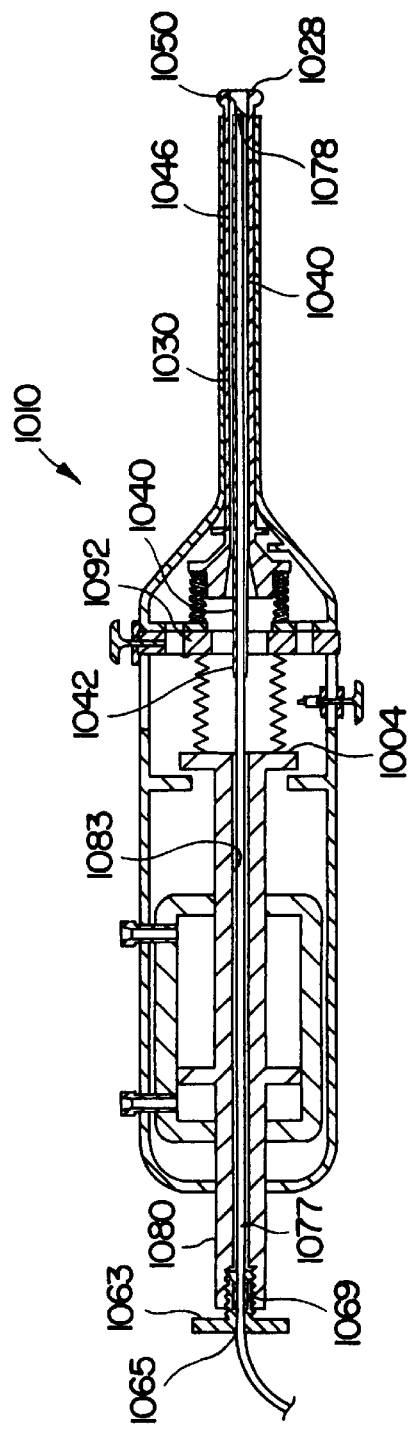
FIG. 14 is a cross-sectional side view of a further embodiment of the present invention with the needle crimped onto the fiber.

FIG. 14 illustrates another embodiment of the present invention which is similar to FIG. 11. However, instead of having a grip for detachably connecting the sleeve to the needle, the needle is crimped onto the fiber wherein any buffer coating may have earlier been removed therefrom. Correspondingly, where appropriate, the last two digits in the 1000 series of numerals depicted in FIG. 14 are connected to elements which have the same function and/or structure as those described with regard to FIGS. 1, 4, 5, 6, and In FIG. 14, device 1010 includes disposable needle 1040 and fiber 1077. The first end 1042 of the needle 1040 is crimped onto the fiber 1077 from which the fiber's buffer coating may have earlier been removed. Preferably, the distal end 1078 of the fiber is positioned within the needle bore 1046 and is proximate to needle point 1050.

The fiber 1077 is attached to the distal end of sleeve 1080 by fiber lock 1063. The fiber 1077 longitudinally extends through sleeve bore 1083. The fiber 1077 and attached needle 1040 also extend within the needle collar bore 1030 with, preferably, the needle point 1050 being positioned within the needle collar bore and proximate to the needle collar second end 1028.

The threaded fiber lock 1063 provides for selectably adjusting the distance between the needle point 1050 and the needle collar second end 1028. The fiber lock 1063 secures the position of the fiber 1077 and needle 1040, relative to sleeve 1080, by screwing the fiber lock into the bore 1083 of the sleeve 1080 such that compression fitting 1069 tightens around, and thus secures, the fiber.

The needle 1040 and fiber 1077 are installed within the device 1010 by loosing the compression fitting and inserting the needle pointed end 1050 into the fiber lock bore 1065. The needle 1040 is then advanced through the sleeve bore 1083 and into the needle collar bore 1030 by pushing fiber 1077 into the sleeve bore. Finally, the fiber lock 1063 is tightened onto the fiber 1077

With the needle 1040 installed in the device 1010 as shown in FIG. 14, the needle first end 1042 extends out of the sleeve bore 1083. The needle 1040 is approximately 3 to 7 centimeters in length with a preferred length of 4 to 6 centimeters.

Axial movement of sleeve 1080 results in like moment of the fiber 1077 and needle 1040 since the fiber is attached to the sleeve and the needle is attached to the fiber. As such, the operation of device 1010 is similar to that described above for device 710 shown in FIG. 11.

FIGS. 15A and 15B illustrate other disposable fiber and needle configurations for use with the device of FIG. 14. FIG. 15A depicts a needle 1040a having a bore 1046a with an inner diameter of approximately 1.5 to 2.0 millimeters. The needle 1040a is crimped onto a 500 to 1000 micron core fiber. In the event the buffer coating of the fiber is removed before crimping the needle to the fiber, the needle bore would be correspondingly smaller.

FIG. 15B shows a device consisting of a SPECTRA-PROBE needle which is a hollow lasing needle attached to the fiber as in U.S. Pat. No. 4,773,413, to Hussein et al., and incorporated herein by reference. (Trimedyne, Inc., Irving, Calif.). The SPECTRAPROBE™ needle 1040b has a bore 1046b with an inner diameter suitable for crimping the needle onto a 200–365 micron core diameter fiber or a bundle of 50–100 core fibers. The SPECTRAPROBE™ needle 1040b has an outer diameter of about 1.0 to 2.5 millimeters, preferably about 1.5 millimeters. Lens 1019 is fixed within bore 1046b and proximate to the distal end 1050 of SPECTRAPROBE™ needle 1040b. The lens 1019 diverges the laser energy emitted from the fiber distal end 1078 beam so that a channel larger than the diameter of the optical fiber 1077 is created.

FIG. 16 depicts another embodiment of the present invention wherein the device is actuated by using compressed air. The device 1110 is similar to that shown in FIG. 13 except that the sleeve 1180 does not pass through cylinder chamber 1101 and the piston 1171 does not extend from the sleeve. Correspondingly, where appropriate, the last two digits in the 1100 series of numerals depicted in FIG. 16 are connected to elements which have the same function and/or structure as those described with regard to FIGS. 1, 4, 5, 6, and 13.

As illustrated by FIG. 16, cylinder 1188 is secured by conventional means to the housing 1112 within cavity 1118. Shaft 1115 slidably extends through the cylinder 1188 with piston 1171 radially outwardly extending from the shaft within the cylinder chamber 1101.

Preferably, shaft 1115 extends in spaced parallel relationship to sleeve 1180. The ends 1117,1119 of the shaft 1115 extend from the cylinder chamber and are attached, via arms 1121,1123, to the sleeve.

Ports 1102,1103 extend from the device housing 1112 and provide for a fluid medium, preferably air, to ingress and egress from the chamber 1101. The injection of air within port 1102 pushes piston 1171, and thus interconnected sleeve 1180, towards partition 1192. This results in the needle 1140 and fiber 1177 advancing together into the epicardium of the heart and then the fiber, alone, advancing through the endocardium.

Conversely, the injection of air into port 1103 pushes piston 1171, and thus sleeve 1180, away from partition 1192. As such, the fiber distal end 1178 is retracted back into the needle bore 1146 and the needle 1140 is retracted back into the needle collar bore 1130.

FIG. 17 provides a cross-sectional side view of yet another embodiment of the present invention having an activating button and arming light emitting diode (LED).

The device 1210 of FIG. 17 is similar to that depicted in FIG. 11 except that needle collar 725 has been eliminated. Correspondingly, where appropriate, the last two digits in the 1200 series of numerals depicted in FIG. 17 are connected to elements which have the same function and/or structure as those described with regard to FIGS. 1, 4, 5, 6, and 11.

In FIG. 17, shaft 1211 extends from the second end 1216 of the housing 1212. The needle 1240 extends within an open bore 1213 passing through the shaft 1211. Preferably, the needle 1240 is positioned within bore 1213 with the needle point 1250 located proximate to the distal end 1228 of the shaft 1211.

Mounted to the housing are activating button 1221 and indicator LED 1229. The activating button 1221 is connected to the control unit by conventional means to command the control unit to advance and retract the needle 1240 by injecting air into ports 1202 and 1203, respectively. Moreover, the indicator LED is operably connected to the control unit to indicate when the laser unit is ready to transmit laser energy via fiber 1277.

In operation, the shaft distal end 1228 is held against the heart's surface. If indictor LED 1229 is illuminated to indicate that laser energy is available for making a channel in tissue, activating button 1221 is depressed.

The control unit injections air into port 1202 to advance the needle point 1250 from the bore 1213 of shaft 1211. The needle 1240 is fully extended when sleeve flange 1204 abuts against switch 1259 which indicates that the control unit is to retract the needle. Correspondingly, the control unit stops injecting air into port 1202 and begins injecting air into port 1203 which results in the needle being retracted back into bore 1213.

Preferably, during the advancement and retraction of the needle 1240 from bore 1213, laser energy is transmitted into fiber 1277 and emitted from the fiber distal end 1278 in the same manner as that described for the embodiment shown in FIG. 11.

Figure 18:
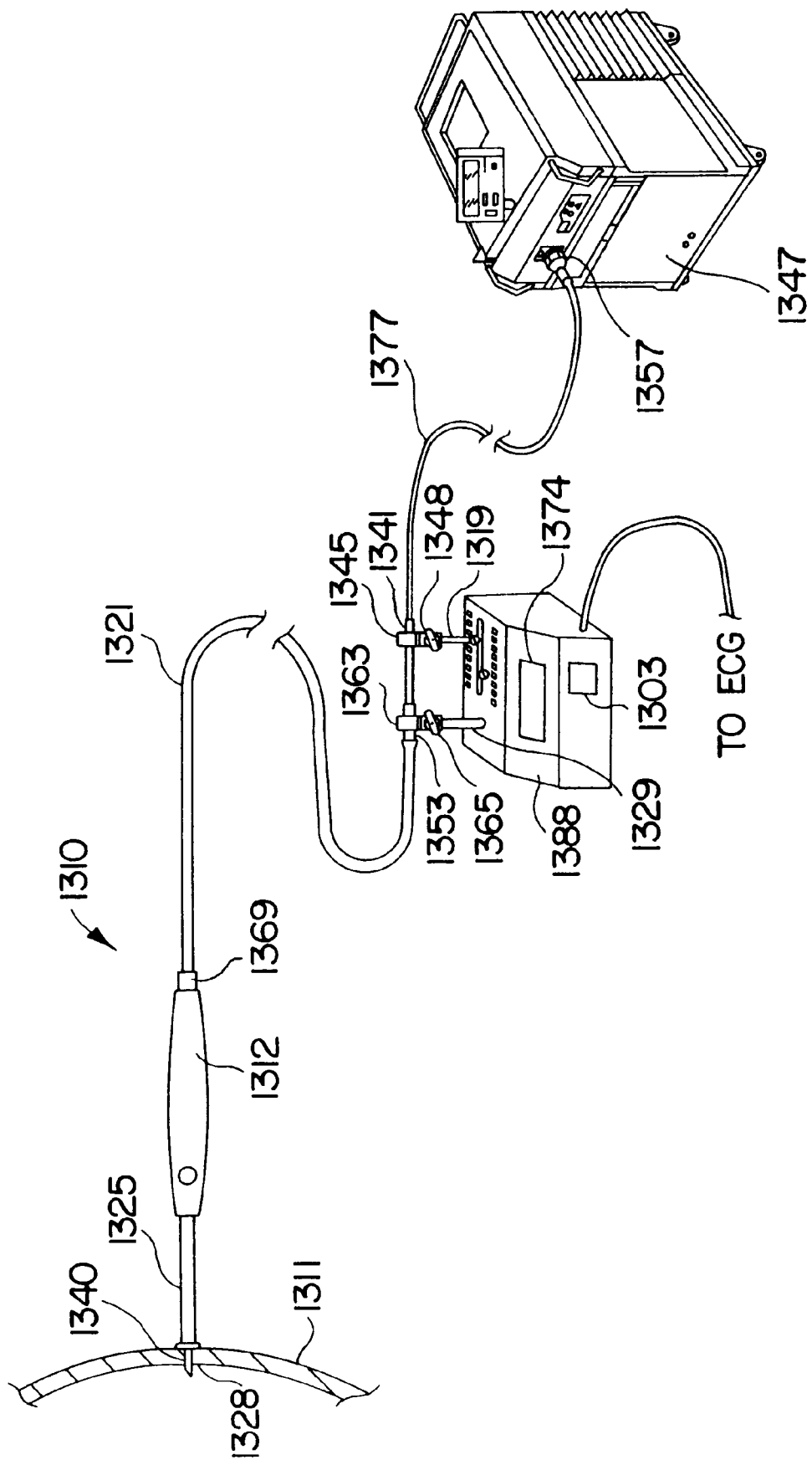
FIG. 18 is a perspective view of another embodiment of the present invention having an external actuator for advancing and withdrawing the fiber and needle from a handpiece.

FIG. 18 provides a perspective view of a preferred embodiment of the present invention wherein an external actuator is used for advancing and withdrawing the optical fiber and needle from a handpiece. The operation of the device shown in FIG. 18 is similar to the embodiments described above. Correspondingly, where appropriate, the last two digits in the 1300 series of numerals depicted in FIG. 18 are connected to elements which have the same function and/or structure as those described with regard to FIGS. 1, 4, 5, 6, and 11.

The device 1310 of FIG. 18 is operatively connected to external actuator 1388 which minimizes both the size and weight of the handpiece or housing 1312. Further, the embodiment of FIG. 18 reduces the number of leads that must be connected to the handpiece 1312 such as air lines and electrical wires for advancing the needle and receiving feedback regarding the needle's position as it is being advanced.

The external actuator 1388 is operably connected to handpiece 1312, a laser energy source 1347, and a conventional ECG (not shown). The laser 1347 is connected to fiber 1377 by conventional fiber optical connector 1357. The laser 1347 receives position signals and command signals from the handpiece 1312 and actuator 1388. When enabled by activation of a footswitch or other means, a preselected amount of laser energy is transmitted into fiber 1377 in response to the position signals. The laser energy is transmitted, via fiber 1377, to the handpiece 1312.

Besides being connected to the laser 1347, the fiber 1377 is also connected to the actuator 1388. The fiber 1377 is attached to drive arm 1319 of actuator 1388 and extends through a flexible cannula 1321 into the handpiece 1312. The fiber 1377 is allowed to slide within the cannula 1321 with one end of the cannula being attached to a fixed arm 1329 of the actuator 1388 and the other end of the cannula being attached to the handpiece 1312.

Figure 19:
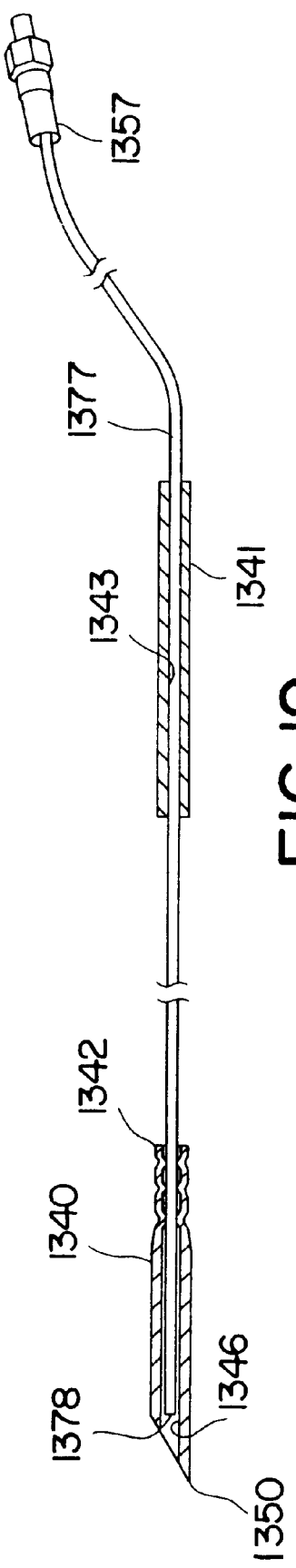
FIG. 19 is a perspective partially cross-sectional view of the needle and fiber of FIG. 18 with a support tube attached to the fiber.

As shown in FIG. 19, needle 1340 is attached proximate to the distal end of fiber 1377. The needle 1340 has a length of about 1 to 10 centimeters, preferably about 4 to 7 centimeters. The first end 1342 of the needle 1340 is crimped onto the fiber 1377, from which the fiber's buffer coating may have earlier been removed. Further, the distal end 1378 of the fiber is preferably positioned within the needle bore 1346 and is proximate to needle point 1350.

A support tube 1341 is also attached to the fiber 1377 for preventing the core of the fiber from being damaged by the force exerted by advancing the drive arm 1319 of actuator 1388. The support tube 1341 is preferably made of metal or a metal alloy and has a longitudinal open bore 1343 for receiving the fiber 1377 which passes through the bore. The fiber 1377 is secured to the tube 1341 by glue or the like.

Returning to FIG. 18, the outer surface of support tube 1341 is removably grasped by clamp 1345 of drive arm 1319. The clamp 1345 releases and secures the support tube 1341 by loosing and tightening, respectively, clamp adjustment handscrew 1348.

Figure 20:
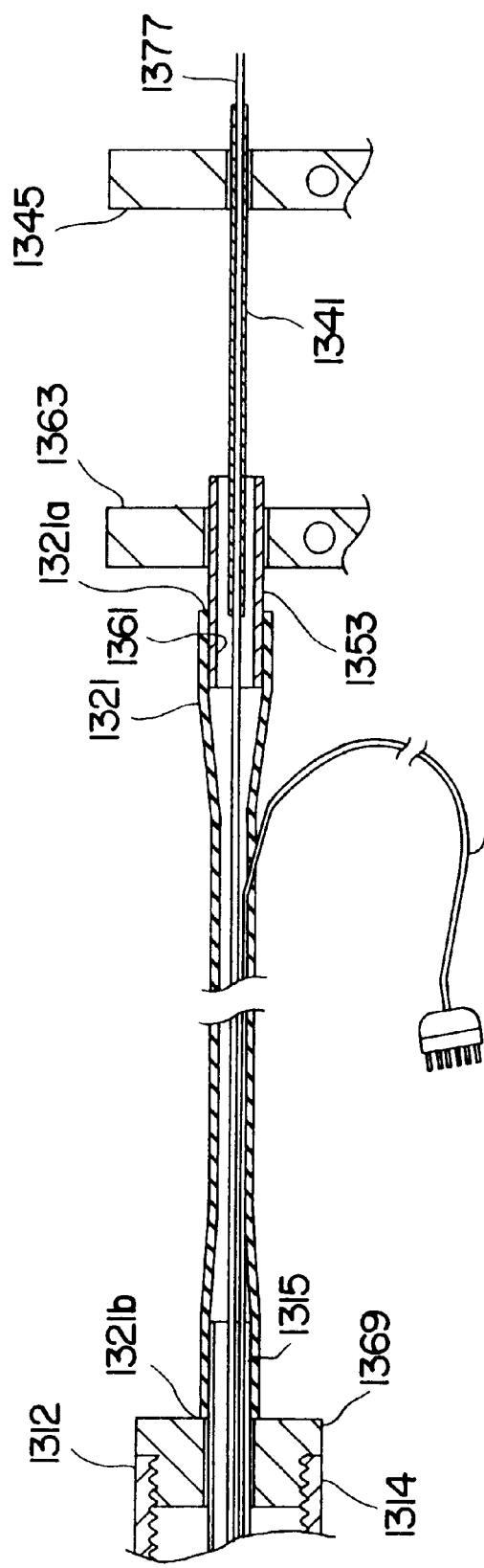
FIG. 20 is a cross-sectional view of the fiber of FIG. 18 passing through both the support tube and a bushing, and then extending into the handpiece.

FIG. 20 depicts the support tube 1341 and attached fiber 1377 passing through a bushing 1353 removably mounted onto the fixed arm 1329 of the actuator 1388. The bushing 1353 may be made of metal or plastic and has a longitudinal open bore 1361 for slidably receiving support tube 1341 and fiber 1377. The inner diameter of the bushing bore 1353 is greater than the outer diameter of the support tube 1341 in order to allow the support tube to freely slide within the bushing 1353.

The bushing 1353 is removably mounted to clamp 1363 of fixed arm 1329. The outer surface of the bushing 1353 is removably grasped by the clamp 1363. The clamp 1363 either releases or securely holds the tube by loosing or tightening, respectively, clamp adjustment handscrew 1365.

One terminal end 1321a of the cannula 1321 is attached to the bushing 1352 by partially inserting the bushing into the cannula 1321. Glue or the like may also be used in securing the cannula 1321 to the bushing 1352.

The other terminal end 1321b of the cannula 1321 is connected to a nipple 1315 extending from plug 1369 of handpiece 1312. The cannula 1321 is fitted over the outer surface of the nipple 1315 and may be secured to the nipple by glue or the like.

Figure 21:
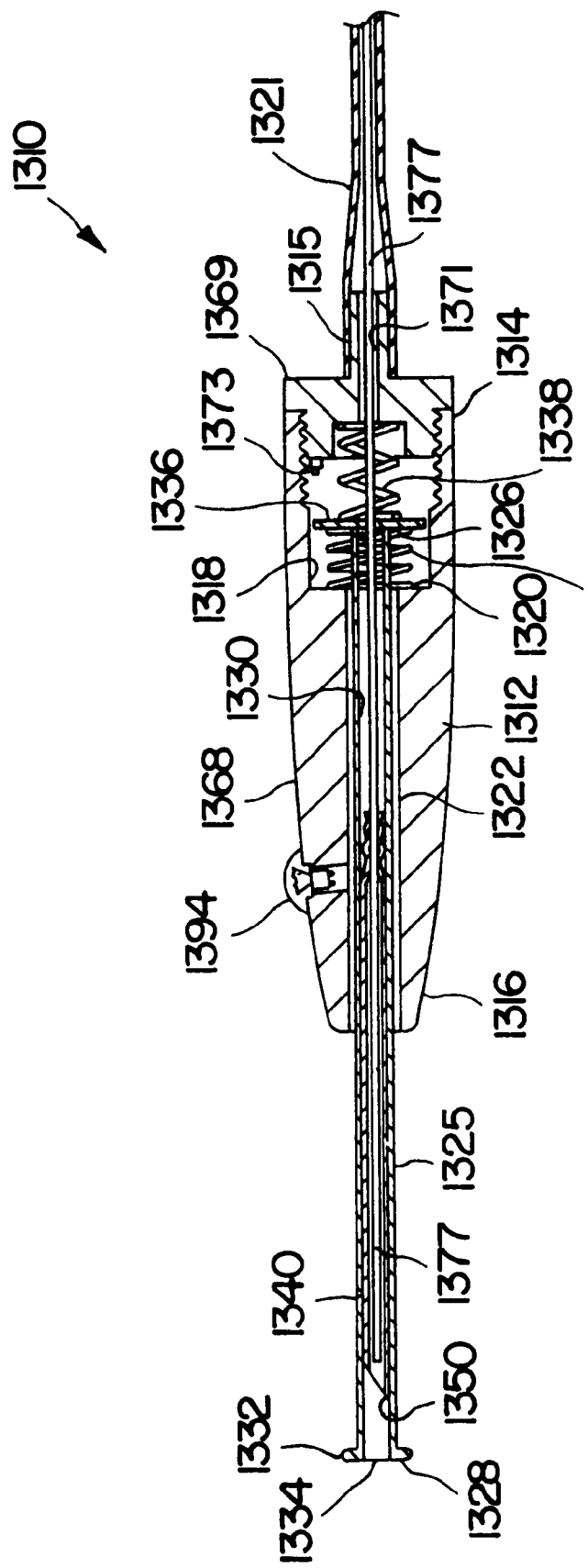
FIG. 21 is a partial cross-sectional view of the handpiece of FIG. 18.

FIG. 21 provides a partial cross-sectional view of the handpiece 1310. The handpiece 1310 includes a generally cylindrical housing 1312 having a first end 1314 and a tapered second end 1316 with an elongated cavity 1318 extending therebetween.

Extending within the housing cavity 1318 is a shoulder 1320. The shoulder 1320 is ring shaped and results in the housing cavity 1318 having a cylindrical longitudinal portion or passage 1322 that is in communication with the outside 1368 of the housing 1312 at the first end 1316.

Slidably mounted within the housing cavity 1318 and extending from the first end 1316 of the handpiece 1310 is a hollow needle collar or guide 1325. The needle collar 1325 is generally cylindrical in shape with an inner end 1326, an outer end 1328, and an open bore 1330 extending therebetween.

The inner end 1326 of the needle collar 1325 extends past shoulder 1320 and has a radially outwardly extending retaining ring 1336 with a larger outer diameter than the inner diameter of cavity passage 1322. Likewise, the outer end 1328 of the needle collar 1325 which protrudes from passage 1322 has a rounded flange 1332 extending around its periphery. The rounded flange 1332 results in the outer end 1328 of the needle collar 1325 having a flat disk shaped surface with the aperture 1334 to bore 1330 being located in the center.

Located between retaining ring 1336 and shoulder 1320 is coiled spring 1382 which wraps around the outer surface of the needle collar 1325. The coiled spring 1382 retractably biases the collar 1325 towards the first end 1314 of the housing 1312.

Threading mounted onto the first end 1314 of the housing 1312 is plug 1369 having an open bore 1371 in communication with the housing cavity 1318 and extending through nipple 1315. Extending through plug bore 1371 and into the needle collar bore 1330 is fiber 1377.

Further, mounted onto the plug 1369 is an electrical switch 1373 which faces towards retaining ring 1336. The switch 1373 provides a means for detecting when the needle collar 1325 has been pushed a fixed distance within the housing cavity 1318. Correspondingly, the switch 1373 is activated only when the retaining ring 1336 of the needle collar 1325 abuts against the switch.

Resiliently biased against retaining ring 1336 and plug 1369 is coiled spring 1338 which forward biases the collar 1325 away from the first end 1314 of the housing 1312.

Attached to the housing 1312 is LED 1394 for indicating that the device 1310 is either ready to, or has completed, making a channel within tissue. The LED 1394 is operably connected to the control unit 1347 by conventional means such as wire leads within wire harness 1395.

Figure 22:
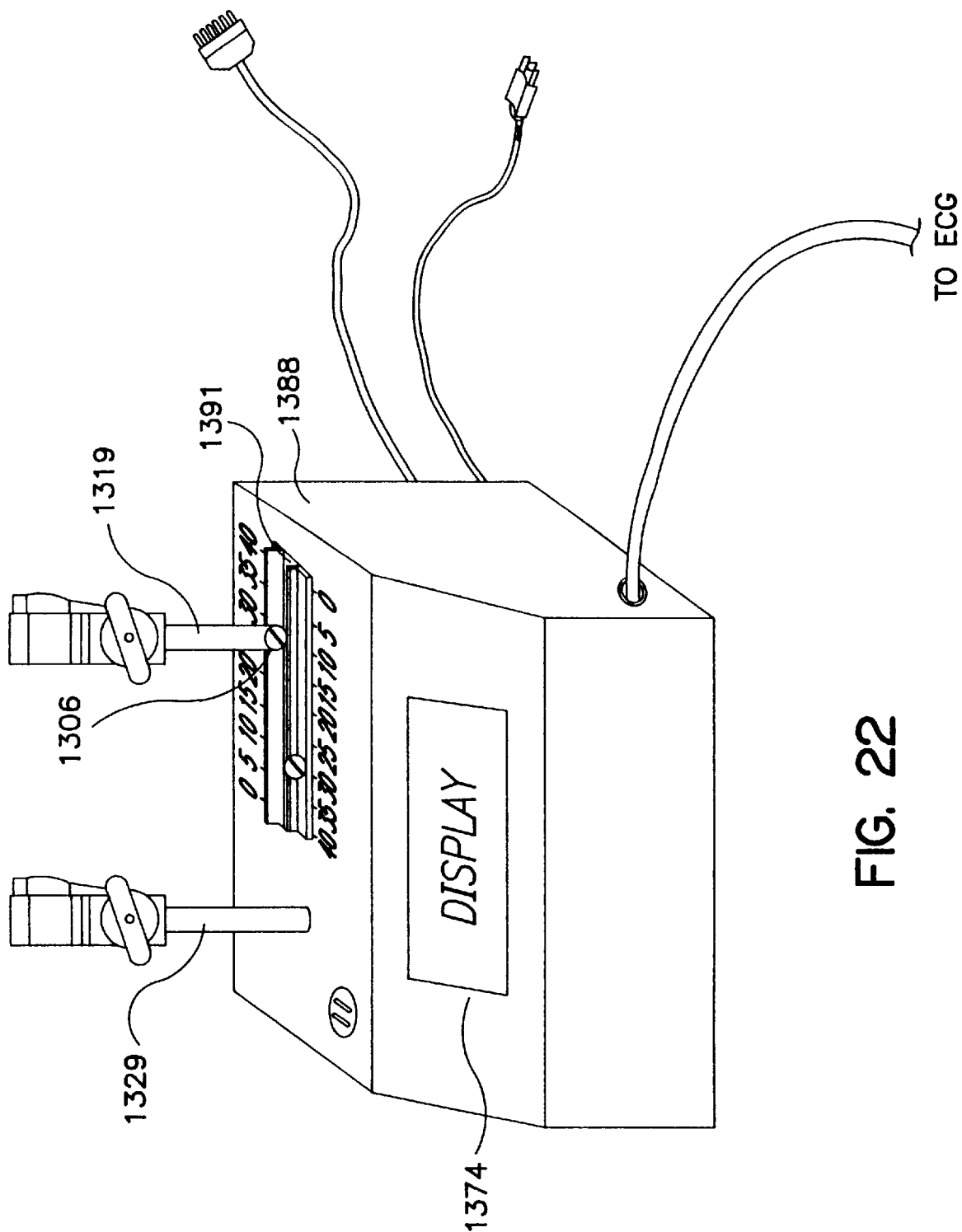
FIG. 22 is a perspective view of the external actuator depicted in FIG. 18.
Figure 24:
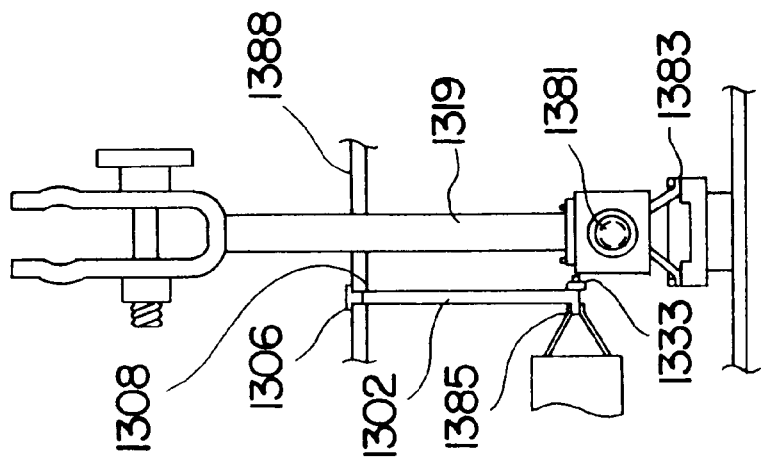
FIG. 24 is an end view of the external actuator along line 24—24 of FIG. 23.
Figure 23:
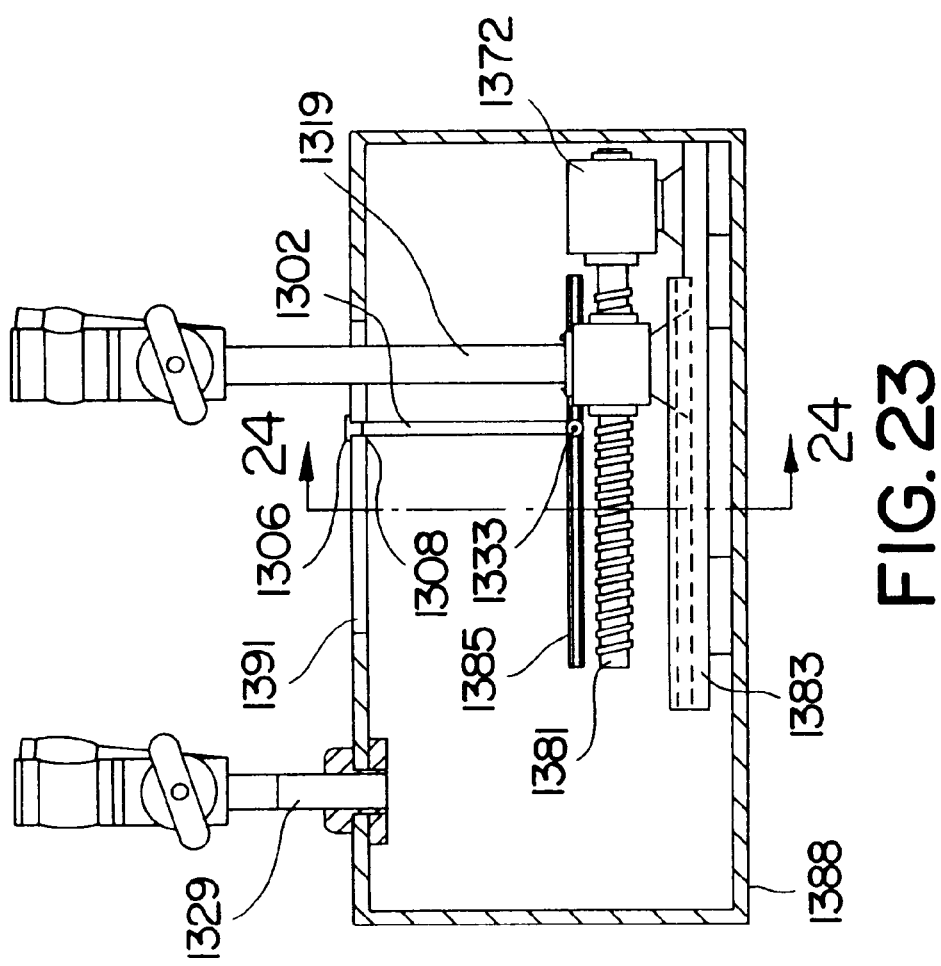
FIG. 23 is a fragmentary partial cross-sectional side view of the external actuator of FIG. 22.

FIGS. 22–24 depict the external actuator 1388 for advancing and withdrawing the optical fiber 1377 and needle 1340 from the handpiece 1310. The actuator 1388 includes a stepper motor 1372 and a conventional active touch-screen display 1374. The stepper motor 1372 operates to advance and withdraw the optical fiber 1377 and needle 1340 by moving drive arm 1319 towards and away from fixed arm 1329.

As seen in FIG. 23, stepper motor 1372 is mounted to the actuator housing and operates to bidirectional rotate shaft 1381 which is threadingly engaged by drive arm 1319. Also mounted to the actuator housing and in spaced parallel relationship to shaft 1381 is track 1383 for sliding engaging drive arm 1319 between the stepper motor 1372 and fixed arm 1329.

In operation, longitudinal axial rotation of the shaft 1381 by the stepper motor 1372 in the clockwise direction, for example, results in the drive arm 1319 advancing towards the fixed arm 1329. Conversely, rotation in the counterclockwise direction moves the drive arm 1319 away from the fixed arm 1329.

Also mounted to the housing of the external actuator is an elongated track 1385 for slidingly adjusting the position of sensor 1333. The track 1385 is generally in spaced parallel relationship to the stepper motor shaft 1381. The sensor 1333 can be moved along track 1385 by attached post 1302 which extends into a elongated channel 1391 between arms 1319 and 1329.

Threadably attached to the distal end 1308 of post 1302 is a set screw 1307 for adjustable fixing the position of sensor 1333 along track 1385. The set screw 1307 abuts against the outside of the actuator housing and is adjustably secured to the housing by tightening the set screw. Correspondingly, positioning of the set screw 1308 results in like placement of the sensor 1333 along track 1385.

The sensor 1333 is activated, preferably, when it comes in contact with, or is brushed by, drive arm 1319. As such, the sensor 1333 detects when the drive arm 1319 is within a predetermined distance from the fixed arm 1329 which corresponds to the distance that the needle 1340 is advanced, or retracted, from the second end 1328 of the needle collar 1325.

Figure 25:
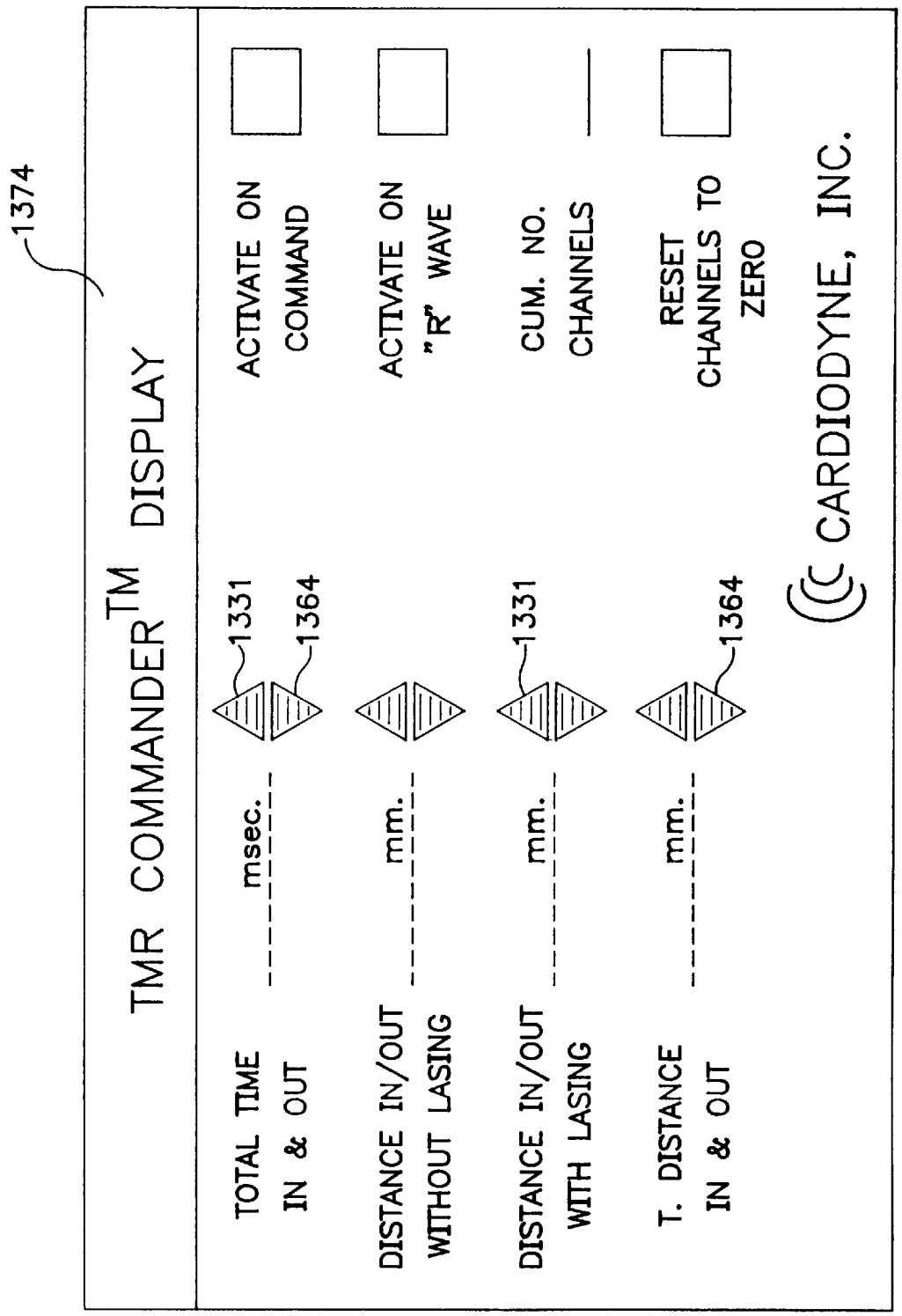
FIG. 25 is a touch-screen display provided by the external actuator of FIG. 22.
Figure 30:
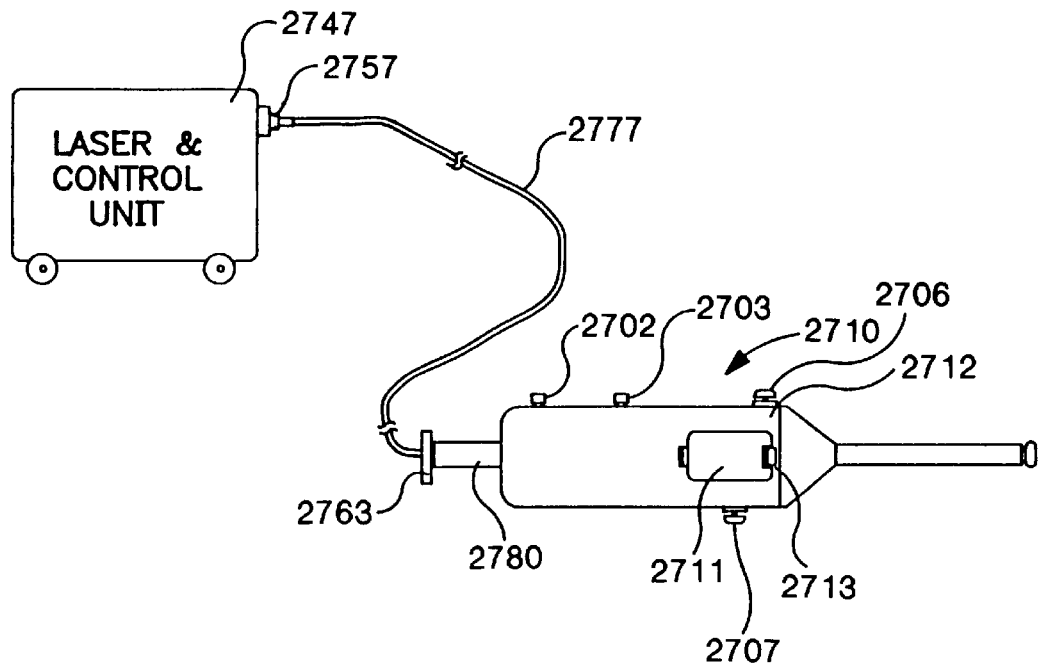
FIG. 30 is a perspective top view of another device, connected to a laser energy source, that embodies the present invention and includes a door for accessing a disposable needle.

FIG. 25, depicts a preferred embodiment of the display 1374 provided by the external actuator 1388. The display 1374 provides for selection and activation of various functions to be performed during a TMR procedure. The display 1374 is stimulated by conventional means such as the touch of a finger.

The display 1374 includes options such as a "ACTIVATE ON COMMAND" touch area for activating the device 1310 to form a channel by depressing a button mounted on the handpiece or the like. The display 1374 also includes an "ACTIVATE ON "R" WAVE" touch area to command the device 1310 to form a channel when the next recognizable "r" wave is determined. Further, the display 1374 includes a "CUMULATIVE NUMBER OF CHANNELS" area for displaying how may channels have be formed by the device 1310. The count shown on the "CUMULATIVE NUMBER OF CHANNELS" area can be reset to zero by touching the "RESET CHANNELS TO ZERO" touch area.

Other operational settings such as the time and distance that the needle 1340 is to advance and retract from the handpiece 1312 are provided by the display 1374. These settings are selected by up touch area arrows 1331 and down touch area arrows 1364 provided on the display.

Referring back to FIGS. 18 and 26, the laser 1347 is enabled by depressing a footswitch or the like. The laser 1347 initially provides laser energy which is diverted into a heat sink by a mirror or shutter as explained above. The device 1310 is then operated by pressing the second end 1328 of the needle collar 1325 against heart 1311 until retaining ring 1336 abuts against switch 1373. Activation of switch 1373 results in the illumination of LED 1394 to indicate that the device 1310 is armed and is awaiting the next recognizable "r" wave of the patent's ECG.

Within the external actuator 1388 is a controller 1303 for determining when to form the channel in heart 1311. The controller 1303 makes its determination by interposing an appropriate delay time from the next recognizable "r" wave of the patient's ECG, while taking care to avoid activation in the event any unusual variation in heart rhythm.

When the controller 1303 determines that a channel is to be made, the controller operates stepper motor 1372 to advance movable arm 1319 towards fixed arm 1329. As the arms 1319,1329 are moved towards each other, support tube 1341 is pushed further within bushing 1353 which advances needle 1340 from the second end 1328 of the needle collar 1325 and into heart 1311.

As the fiber 1377 and attached needle 1340 are being advanced, movable arm 1319 actives switch 1333 which results in laser energy being emitted, via fiber 1377, from the fiber distal end 1378. The laser energy is, preferably, transmitted into the fiber by retracting a shutter or mirror within the laser unit 1347 as explained, in detail, above.

The microcontroller 1303 continues to advance the needle 1340 until it is advanced the preselected distance entered by the surgeon using display 1374 as depicted by FIG. 26. Thereafter, the microcontroller 1303 reverses the rotational direction of the stepper motor to retract the needle 1340 back into needle collar 1325.

As the needle 1340 is being retracted, movable arm 1319 again activates switch 1333 which stops the transmission of laser into fiber 1377 by deflecting the laser energy provided by the laser unit 1347 into a beam dump as explained, in detail, above.

The microcontroller 1303 continues to retract the needle 1340 until the needle point 1350 is positioned back into the needle collar bore 1330. The LED 1394 is then turned off by microcontroller 1303 to indicated that the channel making process has been completed.

The surgeon may then remove his foot from the laser's footswitch and reposition the handpiece 1312 to repeat the process of making a channel in the heart 1311 or he may continue to depress the footswitch throughout the making of any number of channels.

FIG. 27 depicts a cross-sectional view of another handpiece in accordance with the present invention. The handpiece 1412 is similar to that shown in FIG. 21 except that the needle collar 1425 is securely mounted to the handpiece and an activating button 1467 is provided. Correspondingly, where appropriate, the last two digits in the 1400 series of numerals depicted in FIG. 27 are connected to elements which have the same function and/or structure as those described with regard to FIGS. 18–26.

In FIG. 27, needle collar 1425 is secured to plug 1369 and extends from the second end 1416 of the handpiece 1412. Attached to the portion 1437 of the needle collar 1425 that extends from the handpiece second end 1416 is cannula 1421.

The fiber 1477 within the cannula 1421 extends into the needle collar bore 1430. The pointed end 1450 of the needle 1440 attached to the fiber 1477 is positioned proximate to the needle collar second end 1428.

Activating button 1467 is mounted on the outside of the handpiece 1412 and is operably connected to the control unit. The button 1447 is depressed by a surgeon when the second end of the needle collar 1428 is abutted against the heart. Depressing the button 1640 commands the device to being forming a channel in the heart as described above with regard to FIGS. 18–26.

Referring to FIGS. 18 and 27, by adjusting the position of fiber 1477 within clamp 1345 of activator arm 1319, the distal end 1450 of needle 1440 may be extended 1 to 6 millimeters, preferably about 3 to 4 millimeters, distally from flange 1428 of needle collar 1425. In this embodiment, when device 1412 is pressed against the heart, needle 1440 penetrates into the epicardium. When button 1467 is depressed on the next recognizable "r" wave, the needle 1440 and fiber 1477, with laser transmission, advance through the endocardium into the heart chamber and retract to their original position. Device 1412 and needle 1440 are then manually withdrawn from the heart.

FIG. 28 shows an alternate embodiment of the handpiece shown in FIG. 27 except that the needle collar is detachably secured to the handpiece and is curved at an angle of approximately thirty (30) degrees.

In FIG. 28, a threaded collar fitting 1570 is attached to the first end 1514 of the handpiece 1512. The needle collar 1525 longitudinally extends through an open bore 1575 in fitting 1570 and into housing cavity 1518. Adhesive 1576 is used to secure the needle collar to the fitting 1570. Further, the portion of the needle collar 1525 which extends from the handpiece 1512 is bent at an angle of approximately thirty degrees (30°).

In this embodiment, needle 1540 is 0.5 to 2.0 centimeters in length, preferably about 0.8 to 1.5 centimeters in length. Tubing 1584 surrounds the fiber 1577 and is attached proximate to needle 1540 to avoid the proximal end of needle 1540 hanging up on flange 1528 of needle collar 1525 when being retracted thereinto. Preferably, the tubing 1584 is made of plastic and has the same outside diameter as that of the needle 1540. The tubing 1584 is attached to the fiber 1577 by adhesive.

Tubing 1584 is about 2 to 10 centimeters in length, and preferably is 6 centimeters in length, such that the tubing is longer than the stroke length of the external actuator.

FIG. 29 illustrates another handpiece 1612 which is similar to that shown in FIG. 28 except that the portion of the needle collar 1625 which extends from the handpiece is bent at an angle of approximately ninety degrees (90°). Alternate shapes of needle collar 1625 may range from 20° to 180°.

In the device 1310 previously disclosed and illustrated by FIGS. 18–26, considerable recoil was encountered when the needle 1340 penetrated the epicardium, which is a tough, very dense, outer layer of the heart muscle. This recoil can be reduced by increasing the rate at which needle 1340 penetrates the epicardium, ramping up to the speed at which the needle 1340 penetrates the endocardium. The recoil effect can also be reduced, as described above, by allowing the needle 1340 to extend 3 to 6 millimeters from the second end 1328 of the needle collar 1325. When the second end 1328 of needle collar 1325 is manually pressed against the heart, the needle passes into or through the epicardium. When the external actuator 1388 is activated, significantly less recoil results as the needle 1340 traverses the remainder of the epicardium and the endocardium.

However, in order to prevent scratching of the heart or other tissue by the exposed needle when moving the device around the side or posterior surface of the heart, the needle may be temporarily retracted within the tube and extended when the device has been re-positioned.

Extending the needle from the tube also allows the needle to cool more effectively in the air, after lasing, and avoids heating the second end 1328 of the needle collar 1325 by not enclosing the hot needle therewithin.

Another benefit of extending the needle 1340 3 to 6 millimeters from the second end 1328 of the needle collar 1325 is that additional lasing time is obtained, allowing for more energy pulses to be emitted and a more uniform, larger diameter channel to be created. For example, if the heart wall is 15 millimeters thick, in the earlier described procedure, the needle would travel a total of 18 millimeters (3 millimeters into the heart chamber) and 18 millimeters back. Of this distance, for example, 4 millimeters in and 4 millimeters out of the epicardium would be without lasing. If the entire insertion and withdrawal is done in 0.4 seconds of the 0.6 second period of diastole, assuming a heart rate of 60, the rate of speed would be 36 millimeters in 0.4 seconds or 90 millimeters/second. Lasing would occur during 28 millimeters of the total 36 millimeters distance for 0.313 seconds (0.78 of 0.04 seconds). At a pulse repetition rate of 30 Hertz (2 joules per pulse), an average of 9.39 pulses would be emitted.

However, if the needle extends 4 millimeters distally from the needle collar, the total distance traveled, in and out, would be 28 millimeters (11 millimeters+3 millimeters in and 11 millimeters+3 millimeters out). Lasing can occur during the entire 0.4 second period. At the same pulse repetition rate of 30 Hertz, 12 pulses of energy would be emitted.

As discussed previously, in creating a channel in tissue to be vascularized, in one preferred embodiment having an inner, middle and outer layer such as heart tissue having an endocardium, myocardium and epicardium, it is advantageous to initially penetrate the needle through the outer layer when approaching the heart from the outside, prior to lasing in the middle and inner layers. In another embodiment, a channel is created by lasing from the inside of the heart chamber through the endocardium and myocardium.

In a preferred embodiment, wherein a cavity or pocket is desired to be created in the myocardium, into which a therapeutic agent is to be deposited, with minimal communication through the epicardium or endocardium, the needle penetrates the epicardium from outside the heart or the endocardium from the inside of the heart chamber, without lasing, before emitting laser energy in the myocardium. The therapeutic agent is injected into the just created pocket as the needle is withdrawn from the myocardium.

In one embodiment, it may be advantageous to actuate the device pneumatically, i.e., by using compressed air. FIGS. 30–34 depict such an apparatus which also includes a disposable needle. Correspondingly, where appropriate, the last three digits in the 2000 series of numerals depicted in FIGS. 30–34 are connected to elements which have the same function and/or structure as those described with regard to FIGS. 1, 4, 5, 6, 7–11.

The device 2710 includes a generally rectangular door 2711 that is hinged onto the device housing 2712. The door 2711 includes a conventional clip or latch 2713, opposite the hinge, for securing the door 2711 over an aperture which is in communication with the housing cavity 2718.

Figure 31:
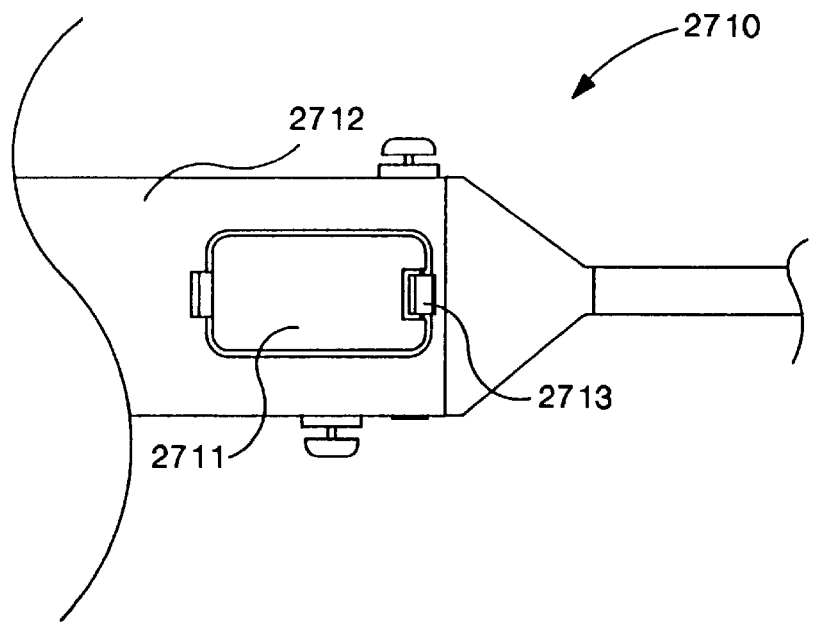
FIG. 31 is an enlarged partial top view of the device of FIG. 30 illustrating the door to access the disposable needle.

As shown in FIG. 31, the door 2711 also includes a resilient guide 2721 which extends from the interior surface 2729 of the door. The guide 2721 includes a stem 2741 which extends generally perpendicular from the door 2711 with a foot 2743 that outwardly projects from the distal end of the stem. Preferably, the foot 2743 has an extended portion 2745 that slopes away from the door interior 2729 and is contoured to press against the needle as explained, in detail, below.

FIGS. 31, 32, and 33 depict one end of the sleeve 2780 within the device 2710 having a socket or grip 2717 for detachably connecting the sleeve 2780 to the needle 2740. The grip 2717 includes a planar annular face 2749 with an arcuate, generally semicircular, lip 2753 perpendicularly projecting from the outer margin of the face 2749. Preferably, the lip 2753 is concave when view from the door 2741 and has an inwardly sloped distal portion 2761.

By placing the first end 2742 of the needle 2740 against sleeve face 2749, the lip 2753 adjoins against the outwardly flared proximal end 2742 of the needle 2740. Thus, the lip 2753 receives and partially engages the needle 2740.

When fiber 2777 is not extending within the needle bore 2746, the needle 2740 is removed from the device 2710 by opening the door 2711 and extracting the needle 2740. As the first end 2742 of the needle 2740 is pulled from the housing cavity 2728, the second end 2744 of the needle first vacates the needle collar bore 2730 in addition to the device cavity 2718.

Conversely, the needle 2740 is inserted within the device 2710 by opening the door 2711 and inserting the second end 2744 of the needle within the device cavity 2728. Preferably, the needle collar bore opening within the device cavity 2728 is funnel shaped for ease in inserting the needle 2740 into the collar 2725. The second end 2744 of the needle 2740 is advanced within the needle collar bore 2730 until the first end 2726 of the needle 2740 is allowed to adjoin against the face 2749 of the sleeve 2780.

Preferably, the inner diameter of the needle bore 2746 has approximately a 1.5 to 2.0 millimeter diameter which allows for a 500 to 1000 micron core fiber to be positioned within bore 2746.

As shown in FIG. 34, sleeve 2780 is longitudinally axially aligned and spaced from the needle collar 2725. Accordingly, while inserting and removing the needle 2740 from the device 2710, needle 2740 must be angled into the device cavity 2718 between the sleeve 2780 and needle collar 2725. As such, it is preferred that needle 2740 allow for resilient flexing while it is both inserted and removed from the needle collar first end 2726 within device 2710.

As stated above, the semicircular lip 2753 of grip 2717 adjoins against the outwardly flared proximal end 2742 of the needle 2740 when needle 2740 is installed within the device 2710. The lip 2753 and the guide foot 2743 forms a socket 2717 for coupling the needle 2740 to the sleeve 2780 by closing the door 2741 such that the foot 2743 of guide 2721 adjoins against the flared portion 2742 of the needle 2740.

With the needle 2740 secured by the grip 2717 to sleeve 2780, the sleeve face 2749 pushes the needle second end 2744 from the needle collar bore 2730 when the sleeve is advanced towards the needle collar 2725. Further, because the guide 2721 is positionally fixed relative to the device housing 2712 but the needle 2740 is not, it is preferred that the extended portion 2745 of foot 2743 resiliently flex in order to allow the needle first end 2742 to advance towards the needle collar 2725 while the guide 2721 remains at its fixed position. Further, the length of the foot 2745 should be greater than the distance traveled by the needle first end 2726 so that a socket 2717 is always provided for continuously securing the needle to the sleeve 2780 as the needle 2740 is advanced and retracted.

The fiber 2777 is coupled by a conventional optical fiber connector 2757 to a laser source 2747 and attaches, via a threaded fiber lock 2763, to the distal end of sleeve 2780. The fiber 2777 longitudinally extends through bore 2783 in sleeve 2780 and into needle bore 2746. Preferably, the second end 2778 of the fiber 2777 is positioned within the needle bore 2746 such that the fiber 2777 is located adjacent to the needle point 2750, but does not protrude from needle bore 2746.

The threaded fiber lock 2763 provides for selectably adjusting the distance between the fiber distal end 2778 and the second end 2744 of needle 2740. The fiber lock 2763 threadably engages the distal end of sleeve 2780 and has an open bore 2765 in communication with the sleeve bore 2783.

The fiber lock 2763 also includes a tubular compression fitting 2769 positioned within the fiber lock bore 2765. The fiber 7727 extends through the fiber lock bore 2765 and compression fitting 2769. The fiber lock 2763 secures the position of the fiber 2777 within the needle bore 2746 by screwing the fiber lock 2763 into the sleeve bore 2783 such that the compression fitting 2769 tightens around, and thus secures, the fiber. Accordingly, the distance between the fiber distal end 2778 and the second end 2744 of needle 2740 is fixably selectable by loosening the compression fitting 2769, moving the fiber 2777 to the desired position, and tightening the compression fitting.

As shown in FIG. 34, radially outwardly extending from the sleeve 2780 is a flange or piston 2771. Preferably, the piston 2771 and the sleeve 2780 are of unitary construction.

The piston 2771 is slidably positionable within an actuator device such as cylinder 2788 which has a generally cylindrical chamber 2701. The cylinder 2788 is secured by conventional means to the housing 2712 within cavity 2718. The sleeve 2780 slidably extends through the cylinder 2788 with the piston 2771 located in the chamber 2701.

Attached to the cylinder 2788 and extending from the outside of the housing 2712 are tubular ports 2702 and 2703 which are in fluid communication with the cylinder chamber 2701. The ports 2702,2703 are generally coupled at each longitudinal end of the cylinder chamber 2701. The ports 2702,2703 provide for a fluid medium, preferably air, to ingress and egress from the chamber 2701.

Between the piston 2771 and the sleeve grip face 2717 is a shoulder flange 2704 for limiting the travel of the sleeve 2780 within the housing cavity 2718. Preferably, the shoulder flange 2704 and the sleeve 2780 are of unitary construction with the shoulder flange radially outwardly extending from the sleeve 2780.

The travel of the shoulder flange 2704 within the housing cavity 2718, and thus sleeve 2780, is bounded by wall 2786 and movable partition 2792. Wall 2786 generally radially inwardly extends from the housing 2712 into cavity 2718. The wall 2786 only partially extends into the housing cavity 2718 to form an aperture 2787 having an inner diameter which is less than the outer diameter of the shoulder flange 2704. Thus, the shoulder flange 2704 cannot pass through the aperture 2787 in wall 2786.

Attached to the wall 2786 proximate to aperture 2787 and facing the shoulder flange 2704 is switch 2705 for indicating when the sleeve 2780, and thus the needle 2740, is retracted. Preferably, switch 2705 is activated when it is abutted by shoulder flange 2704.

Movable partition 2792 also radially inwardly extends within the housing cavity 2718. An aperture 2798 is located generally in the center of the partition 2792 with the sleeve 2780 passing therethrough. Further, radially extending from the periphery of the movable partition 2792 are a plurality of support beams 2719. Associated with each support beam 2719 is an elongated channel 2791a,b which extends through the housing 2712 and between the wall 2786 and annular abutment 2723. Correspondingly, each channel 2791a,b allows its associated support beam 2719 to advance from the housing cavity 2718 to a position generally flush with the outside 2768 of the housing 2712.

Attached to partition 2792 is a locking member comprising a set screw 2706 for adjustably fixing the moveable partition to the housing 2712. Preferably, the set screw 2706 is threadably secured to the movable partition 2792 and extends from the partition, to the outside 2768 of the housing 2712, via elongated channel 2791a. As such, the position of the partition 2792 is adjusted by releasing set screw 2706, moving the partition to the desired location within the housing cavity 2718, and tightening the set screw.

Also attached to partition 2792 proximate to aperture 2798 and facing the shoulder flange 2704 is switch 2759 for indicating when the sleeve 2780, and thus the needle 2740, is fully extended from the device 2710. Preferably, switch 2759 is activated when it is abutted by shoulder flange 2704.

Extending along elongated channel 2791b is a set screw 2707 and clamp assembly 2708 for adjustable moving a sensor 2733 within the housing cavity 2718. The clamp assembly 2708 abuts against both the inside 2718 and the outside 2768 of the housing 2712 with the set screw 2707 extending through the channel 2791b and threadably secured to the clamp assembly.

Sensor 2733 is attached to the clamp 2708 within the housing cavity 2718. The sensor 2733 detects when the sleeve 2780, and thus the needle 2740, has traveled a predetermined fixed distance. As such, the sensor 2733 projects a distance within the housing cavity 2718 that is generally equal to the distance between the housing 2712 and the periphery of shoulder flange 2704.

The set screw 2707 allows for both adjustably securing the clamp 2708 to, and releasing it from, the housing 2712. Correspondingly, positioning of the clamp 2708 results in like placement of the sensor 2733 within the housing cavity 2718. The sensor 2733 is activated, preferably, when it comes in contact with, or is brushed by, the shoulder flange 2704.

Radially outwardly extending from the needle collar 2725 and within the housing cavity 2718 is a stop flange 2709. Further, a post 2715 extends within the housing cavity 2718 to limit the travel of the needle collar 2725 to between the post 2715 and the tapered second end 2716 of the housing 2712.

Mounted on the distal end of post 2715 and facing towards the stop flange 2709 is switch 2773 for detecting when the needle collar 2725 has been pushed a fixed distance within the housing cavity 2718.

As indicated above, before the device 2710 is used for forming a channel within tissue, the distal end 2778 of fiber 2777 is inserted through the bore 2765 of compression fitting 2769. The fiber 2777 proceeds through the fiber lock 2763 and the sleeve bore 2783 such that the fiber is finally positioned within the needle bore 2746.

Preferably, the distal end 2778 of the fiber 2777 is positioned proximate to the needle opening 2751. Fiber lock 2763 is tightened to maintain the position of the distal end 2778 of the fiber 2777 relative to the needle opening 2751.

In a procedure where the heart has been arrested, device 2710 is preferably used with an excimer laser for controllably emitting substantially non-thermal laser energy from the distal end 2778 of fiber 2777. In a procedure where the heart is beating, a laser generating a greater amount of energy is desired.

Before use, the laser 2747 is set to deliver a desired amount of energy. The laser 2747 is enabled to generate laser energy by depressing a footswitch or the like. However, it is desired that no laser energy be transmitted into the fiber 2777, and thus emitted from the fiber distal end 2778, until sensor 733 is activated as explained, in detail, further herein, particularly until needle 2740 initially penetrates the myocardium.

Preferably, in a procedure where the heart has been arrested, device 2710 is positioned by hand such that the second end 2728 of the needle collar 2725 evenly contacts the surface of the heart, i.e., the inner or outer layer. The housing 2712 of the device 2710 is then manually pressed towards the heart such that the needle collar 2725 retracts within the housing cavity 2718 as springs 2738 compress, or as otherwise operated as discussed below.

The advancement of the needle collar 2725 into the housing cavity 2718 is terminated by stop flange 2709 abutting against, and thus activating, switch 2773. Compressed air, provided by a conventional air pump (not shown), is injected into forward air inlet port 2702 by the activation of switch 2773. The compressed air enters the cylinder chamber 2701 and forces against piston 2771 such that the piston, and thus sleeve 2780, are advanced towards partition 2792 and springs 2782 are compressed between flange 2704 and partition 2792. Preferably, the compressed air forces the sleeve 2780 to advance at a preselected velocity of about one (1) to three (3) millimeters per second.

As the sleeve 2780 advances, attached needle 2740 and fiber 2777 are advanced a desired distance, preferably approximately one third (⅓) of the way through the heart wall, until needle 2740 and fiber 2777 initially penetrate the middle layer or myocardium. It is contemplated that needle 2740 and fiber 2777 could initially advance through the inner or outer lay, i.e., the endocardium or epicardium. Sensor 2733 is activated by contact with the shoulder flange 2704. The position of the sensor 2733 is preset by using ultrasound imaging or the like to estimate the thickness of the heart wall.

Sensor 2733 is activated when it comes in contact with the shoulder flange 2704. In response to activation of sensor 2733, the laser unit 2747 transmits laser energy through fiber 2777 which is emitted from the fiber distal end 2778. The fiber 2777 and the needle 2740 continue to advance together, preferably, through the heart tissue, whether first passing through the inner or outer layer. As such, it is desired that the needle 2740 and fiber 2777 are capable of fully traversing through heart wall tissue having a thickness from about 1.5 to 3.5 centimeters, and into the heart chamber or out of the outer layer, by about 0.2 to 0.5 centimeters. Moreover, it is contemplated that only the fiber 2777 may pass through the tissue into the heart chamber while lasing.

The needle 2740 and fiber 2777 pass through the heart wall at the chosen rate of speed until shoulder flange 2704 contacts, and thus actives, reversing microswitch 2759. The switch 2759 is operably connected to the control unit 2747 which detects when the switch has been activated. In response to the switch activation, the control unit 2747 terminates the injection of air into forward air inlet port 2702 and injects air into reverse air inlet port 2703.

The compressed air enters the cylinder chamber 2701 and forces against piston 2771 such that the piston, and thus sleeve 2780, are advanced away from partition 2792 and springs 2782 are allowed to decompress. As such, needle 2740 and fiber 2777 are withdrawn from the heart tissue.

During the withdrawal, shoulder flange 2704 brushes against switch 2733 which commands the control unit 2747 to stop the transmission of laser energy through the fiber 2777 and emanating from the fiber distal end 2778. However, an embodiment is contemplated in which laser transmission continues until some point after the fiber 2777 is withdrawn from the heart chamber and/or tissue. In such embodiment, switch 2733 could be operably connected to a timer (not shown) in control unit 2725 that would continue laser transmission for a predetermined time after shoulder flange 2794 brushes against switch 2733.

The travel of the needle 2740 and fiber 2777 back into needle collar 2725 is stopped when shoulder flange 2704 adjoins against microswitch 2705. Further, the control unit 2747, which is operably connected to microswitch 2705, stops the injection of air into reverse air inlet port 2703 when the flange 2704 adjoins against switch 2705.

Device 2710 is then lifted off the heart tissue, either the epicardium or endocardium, which results in the needle collar 2725 resuming its original position wherein springs 2738 resiliently press stop flange 2709 against the tapered second end 2716 of device housing 2712. The device 2710 is then repositioned to another location on the tissue and the channel making process is began again.

As will be appreciated by those skilled in the art, device 2710 may be mechanically advanced by means other than an air piston, such as a stepper motor or other mechanical means known in the art. However, it is preferred that the rate of advancement be selectable by either mechanical means or by entering a selected rate into a computer/controller as described, in detail, below.

It is further contemplated that needle collar 2725 is fixedly attached or mounted to the housing 2712. In this contemplated embodiment, stop flange 2709 and switch 2773 could be replaced by a push button located on housing 2272 and operably connected to the computer/controller.

As known by those skilled in the art, conventional holmium lasers have a "ramp-up" time of up to 1 second or longer from the time the laser medium is stimulated to produce laser energy until the time when laser energy is actually provided. Thus, it is desired that if device 2710 is used with a conventional holmium laser during surgery, then the delivery of laser energy into fiber 2777 should be gated in the manner illustrated by FIG. 12 to allow the transfer of laser energy into the fiber as soon as commanded.

Preferably, the laser source, which is operably connected to the fiber 2777, is activated to emit laser energy by depressing a foot switch or other switching device (not shown). Activation of the laser source results in the laser energy beam being provided after a sufficient "ramp-time" has elapsed and prior to the commencement of the channel making process. During this time, mirror is in its second position, diverting the laser beam into the beam dump.

When the emission of laser energy into fiber 2777 is desired, the mirror moves into its first position and allows for the virtually undelayed delivery of laser energy into the fiber by moving the mirror 816 out of path of the laser energy. Thus, there is no need to wait for a prolonged "ramp-up" time because the laser energy is continuously available for transmission into the fiber 2777.

If the heart is beating during the procedure, the device 2710 is positioned so that the second end 2728 of needle collar 2725 is close to touching the epicardium or the endocardium of the heart when the heart is fully expanded. The device is then pressed against the heart such that springs 2738 are compressed and stop flange 2709 abuts against, and thus activates, switch 2773. In response to switch 2773 being activated, the control unit 2747 is enabled to control the entry and withdraw of the needle 2740 and fiber 2777 within the heart.

It is desired that the control unit 2747 monitor the heart by a conventional ECG sensing means to control the operation of the device 2710. Device 2710 is controlled by using a signal recognition and timing procedure similar to that disclosed by U.S. Pat. No. 4,788,975, issued to Shturman et al., and incorporated herein by reference. (Trimedyne, Inc., Irvine, Calif.).

Preferably, the heart is in diastole when the device 2710 forms a channel within the heart by advancing and withdrawing the needle 2740. It is desired that the control unit 2747 determine when to form the channel in the heart by interposing an appropriate delay time from the "r" wave of the patient's ECG, taking care to avoid activation of the device in the event of a premature ventricular contraction or any other unusual variation in heart rhythm.

Forming the channel when the heart is in diastole is preferred, because, at that moment, the electrical activity of the heart is least affected by the trauma of the entry of the needle 2740 and the emission of laser energy. Also, the heart chamber is full of blood and the heart wall is at its thinnest.

The present invention may be positioned within the chest cavity by placing the device 2710 during open heart surgery or, preferably, through a puncture between the ribs of the patient. To ensure that the device 2710 is properly positioned in relation to the heart, the surgeon can observe the second end 2728 of the needle collar 2725 by placing an endoscope through a second puncture within the chest wall and either between the ribs or from beneath the rib cage, or by inserting device 2710 through the working channel of an endoscope.

FIG. 35 depicts an embodiment of the present invention which provides for advancing the needle and fiber together, and then advancing the distal end of the fiber from the needle. Correspondingly, where appropriate, the last two digits in the 2000 series of numerals depicted in FIG. 35 are connected to elements which have the same function and/or structure as those described with regard to FIGS. 1, 4, 5, 11, 13 and 30–34.

In FIG. 35, the sleeve 2980 has a compression coupling 2911 extending from the shoulder flange 2904. The compression coupling 2911 includes a needle attachment 2913 and springs 2982.

The needle attachment 2913 provides grip 2917 mounted to a generally disk shaped retaining member 2921. Preferably, the needle attachment 2913 is of unitary construction with an open bore 2929 that passes through the retaining member 2921 and grip 2917. The open bore 2929 also is in longitudinal axial alignment with the needle collar bore 2930 and the sleeve bore 2983.

The grip 2917 of the needle attachment 2913 provides for removably connecting the needle 2940 to the coupling. Further, the retaining member 2921 allows for separately controlling the advancement of the needle 2940 from that of the fiber 2977.

The retaining member 2921 is slidably mounted to guide posts 2941 extending perpendicularly from the sleeve flange 2904. The guide posts 2941 slidably pass through the retaining member 2921 with fasteners 2943 attached to their distal ends to keep the retaining member from sliding off the posts.

Adjustably positionable between the retaining member 2921 and the sleeve flange 2904 is movable partition 2992 for preselecting the desired depth that the needle 2940 and the fiber 2977 are to penetrate within tissue, preferably the middle layer, before the fiber distal end 2978 advances from the needle bore 2946. Aperture 2998 is located generally in the center of the partition 2992 with the fiber 2977 passing therethrough.

Attached to partition 2992 is set screw 2906 for adjustably fixing the moveable partition to the housing 2912. The set screw 2906 extends from the partition 2992, to the outside 2968 of the housing 2912, via elongated channel 2991*a*. The position of the partition 2992, and thus the distance the fiber 2977 and needle 940 travel together, is preselected by securing the partition to the desired location within the housing cavity 718.

Mounted to the sleeve flange 2904 and the retaining member 2921 are springs 2982 which unobtrusively pass through apertures in moveable partition 2992. The springs 2982 resiliently push retaining member 2921 away from the sleeve flange 2904 and against fasteners 2943.

Also attached to partition 2992 and facing shoulder flange 2904 is switch 2959 for indicating when the fiber distal end 2978 is fully extended from the needle bore 2946 by a preselected distance. The switch 2959 is activated when it is abutted by shoulder flange 2904 which also stops the extension of the fiber distal end 2978 from the needle bore 2946.

As such, adjusting the position of the moveable partition 2992 within housing cavity 2918 establishes the distance that the fiber distal end 2978 will extend from the bore 2947.

Located between retaining member 2921 and annular abutment 2723 is a moveable partition 2956 for selecting a desired needle penetration depth beyond the second end 2928 of needle collar 2925. The movable partition 2956 is generally shaped like a flat washer with a hole 2962 in its center and the needle 2940 passing therethrough.

Radially extending from the periphery of the movable partition 2956 are a plurality of support beams 2964 which extend within channels 2991. Each support beam is generally flush with the outside 2968 of the housing 2912.

Attached to moveable partition 2956 is a locking member comprising set screw 2958 for adjustably fixing the position of the partition. The set screw 2958 is threadably secured to the movable partition 2956 and extends onto the outside 2968 of the housing 2712. The position of the partition 2956 is adjusted by releasing set screw 2958, moving the partition to the desired location within the housing cavity 2718, and tightening the set screw 2958.

Mounted to the moveable partition 2956 and the retaining member 2921 are springs 2945 which resiliently push the retaining member away from the partition. Preferably, however, springs 2982 apply more force to press the retaining member 2921 towards partition 2956 than springs 2945 apply to press the retaining member away from partition 2956.

Extending through moveable partition 2956 and annular abutment 2923 are a plurality of bores 2962' wherein each bore is in longitudinal axial alignment with one of the guide posts 2941. The bores 2962' allow the guide posts 2941 to unobstructively pass through partition 2956 and abutment 2923 when the sleeve flange 2904 is advanced towards the partition.

Mounted onto partition 2956 and facing the retaining member 2921 is switch 2933 for detecting when the retaining member, and thus the needle 2940, has traveled a predetermined fixed distance with the needle second end 2944 protruding from the needle collar bore 2930. Preferably, switch 2933 is activated when it is abutted by retaining member 2921.

As stated above, the device 2910 of FIG. 35, is constructed so that needle 2940 and fiber 2977 may advanced together to a preselected distance, initially penetrating the middle layer of the heart, i.e., the myocardium. Thereafter, fiber 2977, alone, may be advanced through the heart tissue, whether advancing through either the epicardium or endocardium.

As the fiber 2977 is withdrawn from the epicardium, or the endocardium as appropriate, laser energy is being emitted from the fiber distal end 2978 until the fiber distal end is extracted back into the need bore 2946. After which, the emission of laser energy ceases and needle 2940 and fiber 2977 are retracted together.

The sleeve 2980, and thus the needle 2940, is advanced by infusing air into forward air inlet 2902. The air pushes the piston 2971 and attached sleeve 2980 such that springs 2945 compress while springs 2982 remain substantially decompressed.

As the sleeve 2980 advances, the retaining member 2921 abuts against switch 2933 which stops the travel of the needle 2940 from the needle collar bore 2930. Further the laser unit is enabled to begin transmitting laser energy which is emitted from the distal end 2978 of fiber 2977.

As sleeve 2980 continues to advance towards partition 2956, fiber 2977, which is affixed to the sleeve 2980 by fiber lock 2963, extends from the needle second end 2944 as springs 2982 begin to compress. The distance that the fiber 2977 extends from the needle 2940 is restricted by the sleeve flange 2904 abutting against reversing microswitch 2959.

Activation of switch 2959 commands the control unit to discontinue injecting air into port 2902 and begin pumping air into port 2903. As such, the fiber distal end 2978 is retracted back into the needle bore 2946 and the needle 2940 is retracted back into the needle collar bore 2930.

In the device 2910 of FIG. 35, the distance that needle 2940 and fiber 2977 advance substantially together is predetermined by adjustably positioning partition 2956 within the housing 2912 and tightening set screw 2958. Further, the distance fiber 2977 advances from the needle 2940 is predetermined by positioning partition 2992 within the housing 2912 and tightening set screw 2906.

Figure 36:
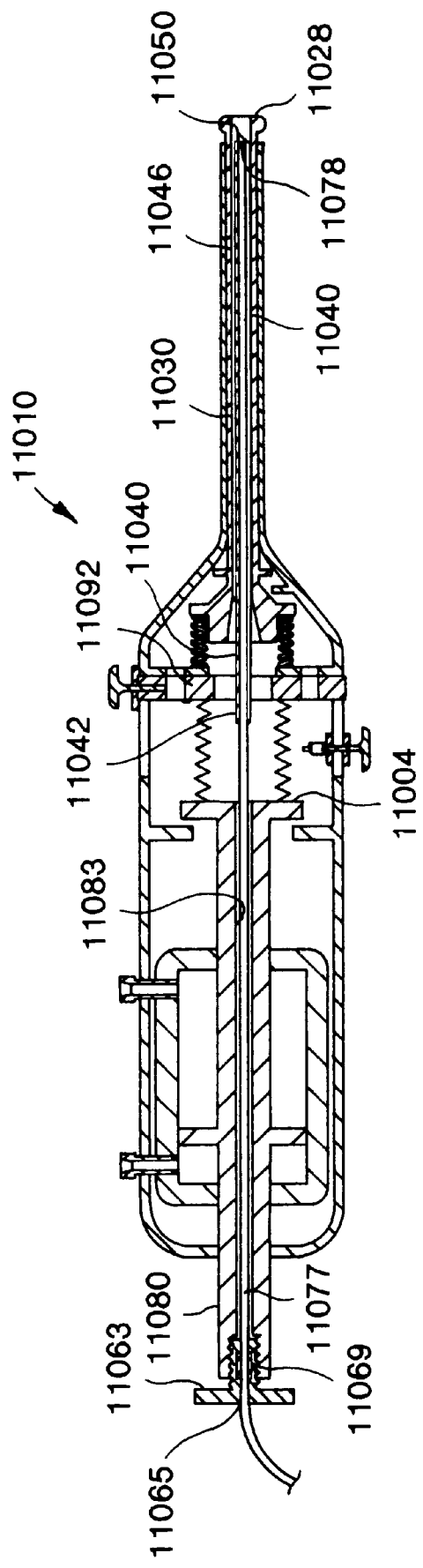
FIG. 36 is a cross-sectional side view of a further embodiment of the present invention with the needle crimped onto the fiber.

FIG. 36 illustrates another embodiment of the present invention which is similar to FIGS. 14 and 34. However, instead of having a grip for detachably connecting the sleeve to the needle, the needle is crimped onto the fiber wherein any buffer coating may have earlier been removed therefrom. Correspondingly, where appropriate, the last two digits in the 10000 series of numerals depicted in FIG. 36 are connected to elements which have the same function and/or structure as those described with regard to FIGS. 1, 4, 5, 6, 11, 13, 14 and 34.

In FIG. 36, device 10010 includes disposable needle 11040 and fiber 11077. The first end 11042 of the needle 11040 is fixedly attached, preferably by crimping, onto the fiber 11077 from which the fiber's buffer coating may have earlier been removed. Preferably, the distal end 11078 of the fiber 11077 is positioned within the needle bore 11046 and is proximate to needle point 11050.

The fiber 11077 is attached to the distal end of sleeve 11080 by fiber lock 11063. The fiber 11077 longitudinally extends through sleeve bore 11083. The fiber 11077 and attached needle 11040 also extend within the needle collar bore 11030 with, preferably, the needle point 11050 being positioned within the needle collar bore and proximate to the needle collar second end 11028.

The threaded fiber lock 11063 provides for selectably adjusting the distance between the needle point 11050 and the needle collar second end 11028. The fiber lock 11063 secures the position of the fiber 11077 and needle 11040, relative to sleeve 11080, by screwing the fiber lock 11063 into the bore 11083 of the sleeve 11080 such that compression fitting 11069 tightens around, and thus secures, the fiber 11077.

The needle 11040 and fiber 11077 are installed within the device 11010 by loosing the compression fitting and inserting the needle pointed end 11050 into the fiber lock bore 11065. The needle 11040 is then advanced through the sleeve bore 11083 and into the needle collar bore 11030 by pushing fiber 11077 into the sleeve bore 11083. Finally, the fiber lock 11063 is tightened onto the fiber 11077

With the needle 11040 installed in the device 11010 as shown in FIG. 36, the needle first end 11042 extends out of the sleeve bore 11083. The needle 11040 is approximately 3 to 7 centimeters in length with a preferred length of 4 to 6 centimeters.

Axial movement of sleeve 11080 results in like moment of the fiber 11077 and needle 11040 since the fiber is attached to the sleeve and the needle is attached to the fiber. As such, the operation of device 11010 is similar to that described above for devices 710 and 2710 shown in FIGS. 11 and 30–34.

Figure 37A:
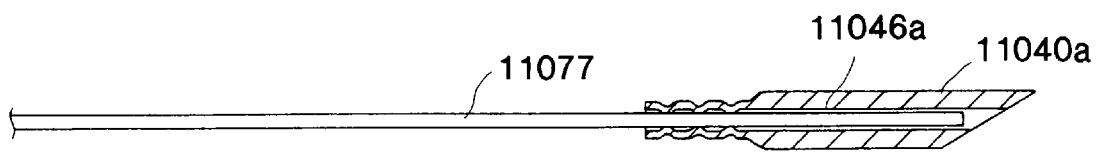
FIGS. 37A–37B each depict a cross-sectional side view of various disposable fiber and needle configurations for use with the device of FIG. 36.
Figure 37B:
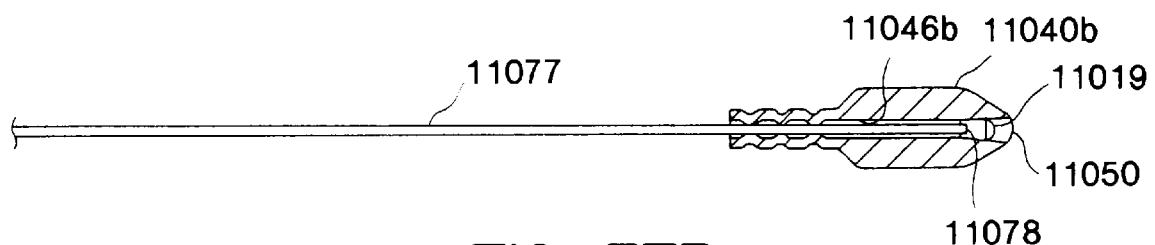

FIGS. 37A and 37B illustrate other disposable fiber and needle configurations for use with the device of FIG. 36. FIG. 37A depicts a needle 11040*a* having a bore 11046*a* with an inner diameter of approximately 1.5 to 2.0 millimeters. The needle 11040*a* is fixedly attached, preferably by crimping, onto a 500 to 1000 micron core fiber. In the event the buffer coating of the fiber is removed before crimping the needle to the fiber, the needle bore would be correspondingly smaller.

FIG. 37B shows a device consisting of a SPECTRAPROBE™ needle which is a hollow lasing needle attached to the fiber as in U.S. Pat. No. 4,773,413, to Hussein et al., and incorporated herein by reference. (Trimedyne, Inc., Irving, Calif.). The SPECTRAPROBE™ needle 11040*b* has a bore 11046*b* with an inner diameter suitable for crimping the needle onto a 200–365 micron core diameter fiber or a bundle of 50–100 core fibers. The SPECTRAPROBE™ needle 11040*b* has an outer diameter of about 1.0 to 2.5 millimeters, preferably about 1.5 millimeters. Lens 11019 is fixed within bore 11046*b* and proximate to the distal end 11050 of SPECTRAPROBE™ needle 11040*b*. The lens 11019 diverges the laser energy emitted from the fiber distal end 11078 beam so that a channel larger than the diameter of the optical fiber 11077 is created.

Figure 38:
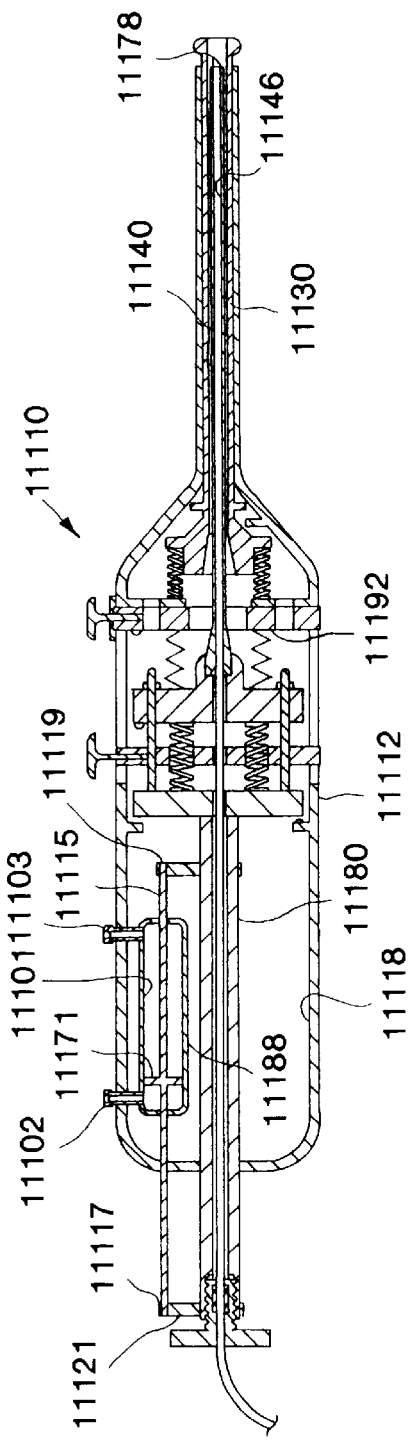
FIG. 38 is a cross-sectional side view of another device in accordance with the present invention wherein the device is actuated by using compressed air.

FIG. 38 depicts another embodiment of the present invention wherein the device is actuated by using compressed air. The device 11110 is similar to that shown in FIGS. 13 and 35 except that the sleeve 11180 does not pass through cylinder chamber 11101 and the piston 11171 does not extend from the sleeve. Correspondingly, where appropriate, the last two digits in the 11100 series of numerals depicted in FIG. 38 are connected to elements which have the same function and/or structure as those described with regard to FIGS. 1, 4, 5, 6, 13 and 35.

As illustrated by FIG. 38, cylinder 11188 is secured by conventional means to the housing 11112 within cavity 11118. Shaft 11115 slidably extends through the cylinder 11188 with piston 11171 radially outwardly extending from the shaft 11115 within the cylinder chamber 11101.

Preferably, shaft 11115 extends in spaced parallel relationship to sleeve 11180. The ends 11117,11119 of the shaft 11115 extend from the cylinder chamber and are attached, via arms 11121,11123, to the sleeve.

Ports 11102,11103 extend from the device housing 11112 and provide for a fluid medium, preferably air, to ingress and egress from the chamber 11101. The injection of air within port 11102 pushes piston 11171, and thus interconnected sleeve 11180, towards partition 11192. This results in the needle 11140 and fiber 11177 advancing together into the heart tissue, initially penetrating the myocardium and then the fiber, alone, advancing through the epicardium, or the endocardium as appropriate.

Conversely, the injection of air into port 11103 pushes piston 11171, and thus sleeve 11180, away from partition 11192. As such, the fiber distal end 11178 is retracted back into the needle bore 11146 and the needle 11140 is retracted back into the needle collar bore 11130.

Figure 39:
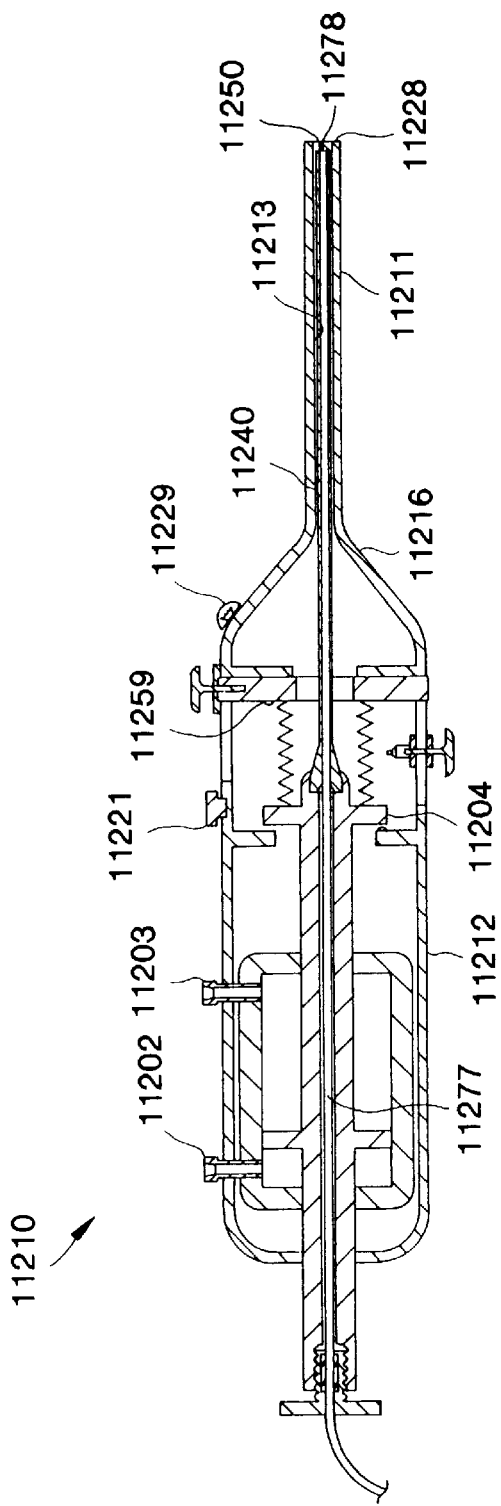
FIG. 39 is a cross-sectional side view of yet another embodiment of the present invention.

FIG. 39 provides a cross-sectional side view of yet another embodiment of the present invention having an activating button and arming light emitting diode (LED). The device 11210 of FIG. 39 is similar to that depicted in FIGS. 11 and 34 except that needle collar 725 and 2725 have been eliminated. Correspondingly, where appropriate, the last two digits in the 11200 series of numerals depicted in FIG. 39 are connected to elements which have the same function and/or structure as those described with regard to FIGS. 1, 4, 5, 6, 11, and 34.

In FIG. 39, shaft 11211 extends from the second end 11216 of the housing 11212. The needle 11240 extends within an open bore 11213 passing through the shaft 11211. Preferably, the needle 11240 is positioned within bore 11213 with the needle point 11250 located proximate to the distal end 11228 of the shaft 11211.

Mounted to the housing are activating button 11221 and indicator LED 11229. The activating button 11221 is connected to the control unit by conventional means to command the control unit to advance and retract the needle 11240 by injecting air into ports 11202 and 11203, respectively. Moreover, the indicator LED is operably connected to the control unit to indicate when the laser unit is ready to transmit laser energy via fiber 11277.

In operation, the shaft distal end 11228 is held against the heart's inner or outer layer. If indictor LED 11229 is illuminated, laser energy is available for making a channel in tissue, activating button 11221 is depressed.

Air is injected into port 11202 as controlled by the control unit to advance the needle point 11250 from the bore 11213 of shaft 11211 initially penetrating the myocardium after which laser energy is transmitted. The needle 11240 is fully extended when sleeve flange 11204 abuts against switch 11259 which indicates that the control unit is to retract the needle. Correspondingly, the control unit stops injecting air into port 1202 and begins injecting air into port 1203 which results in the needle being retracted back into bore 1213.

As provided below, the laser energy source is in operable communication with a proximal end of the fiber 11277. Preferably, during the advancement and retraction of the needle 11240 from bore 11213, laser energy is transmitted into a proximal end of the fiber 11277 and emitted from the fiber distal end 11278 in the same manner as that described for the embodiment shown in FIGS. 11 and 34.

Figure 40:
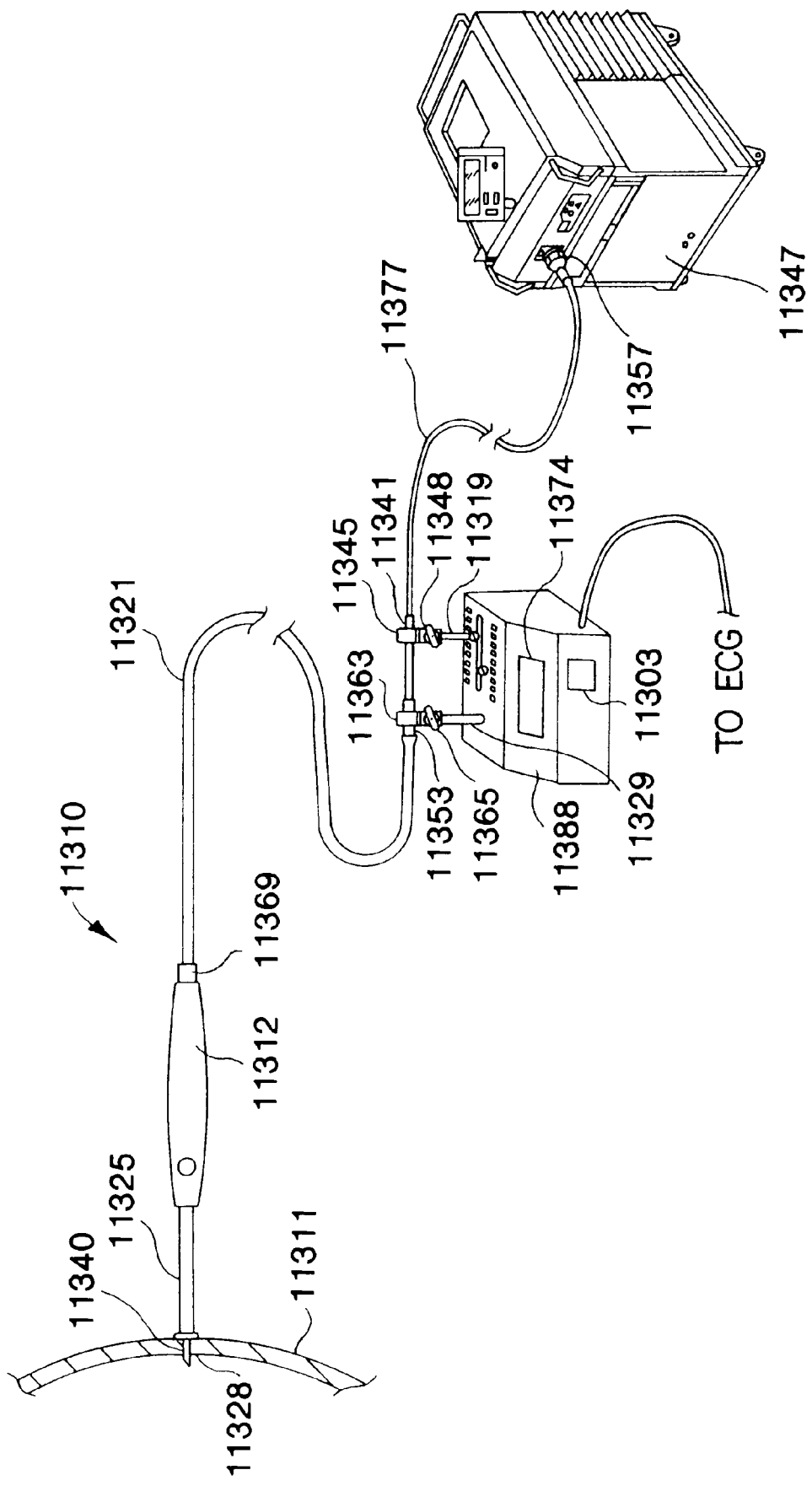
FIG. 40 is a perspective view of another embodiment of the present invention having an external actuator for advancing and withdrawing the fiber and needle from a handpiece.

FIG. 40 provides a perspective view of a preferred embodiment of the present invention wherein an external actuator is used for advancing and withdrawing the optical fiber and needle from a handpiece. The operation of the device shown in FIG. 40 is similar to the embodiments described above. Correspondingly, where appropriate, the last two digits in the 11300 series of numerals depicted in FIG. 40 are connected to elements which have the same function and/or structure as those described with regard to FIGS. 1, 4, 5, 6, 11, 18, and 34.

The device 11310 of FIG. 40 is operatively connected to external actuator 11388 which minimizes both the size and weight of the handpiece or housing 11312. Further, the embodiment of FIG. 40 reduces the number of leads that must be connected to the handpiece 11312 such as air lines and electrical wires for advancing the needle and receiving feedback regarding the needle's position as it is being advanced.

The external actuator 11388 is operably connected to handpiece 11312, a laser energy source 11347, and a conventional ECG (not shown). The laser 11347 is connected to a proximal end of fiber 11377 by conventional fiber optical connector 11357. The laser 11347 receives position signals and command signals from the handpiece 11312 and actuator 11388. When enabled by activation of a footswitch or other means, a preselected amount of laser energy is transmitted into fiber 111377 in response to the position signals. The laser energy is transmitted, via fiber 111377, to the handpiece 11312.

Besides being operably connected to the laser 11347, the fiber 11377 is also connected to the actuator 11388. The fiber 11377 is attached to drive arm 11388 of actuator 11388 and extends through a flexible cannula 11321 into the handpiece 11312. The fiber 11377 is allowed to slide within the cannula 11321 with one end of the cannula being attached to a fixed arm 11329 of the actuator 11388 and the other end of the cannula being attached to the handpiece 11312.

Figure 41:
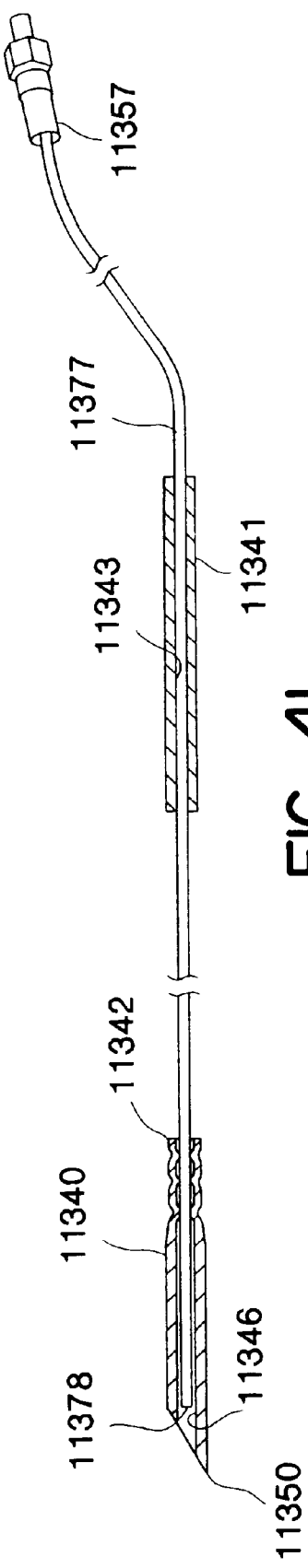
FIG. 41 is a perspective partially cross-sectional view of the needle and fiber of FIG. 40 with a support tube attached to the fiber.

As shown in FIG. 41, needle 11340 is attached proximate to the distal end of fiber 11377. The needle 11340 has a length of about 1 to 10 centimeters, preferably about 4 to 7 centimeters. The first end 11342 of the needle 11340 is fixedly attached, preferably by crimping, onto the fiber 11377, from which the fiber's buffer coating may have earlier been removed. However, it is also contemplated that fiber 11377 may slidingly reside in needle 11340. Further, the distal end 11378 of the fiber is preferably positioned within the needle bore 11346 and is proximate to needle point 11350.

A support tube 11341 is also attached to the fiber 11377 for preventing the core of the fiber from being damaged by the force exerted by advancing the drive arm 11319 of actuator 11388. The support tube 11341 is preferably made of metal or a metal alloy and has a longitudinal open bore 11343 for receiving the fiber 11377 which passes through the bore. The fiber 11377 is secured to the tube 11341 by glue or the like.

Returning to FIG. 40, the outer surface of support tube 11341 is removably grasped by clamp 11345 of drive arm 11319. The clamp 111345 releases and secures the support tube 11341 by loosing and tightening, respectively, clamp adjustment handscrew 11348.

Figure 42:
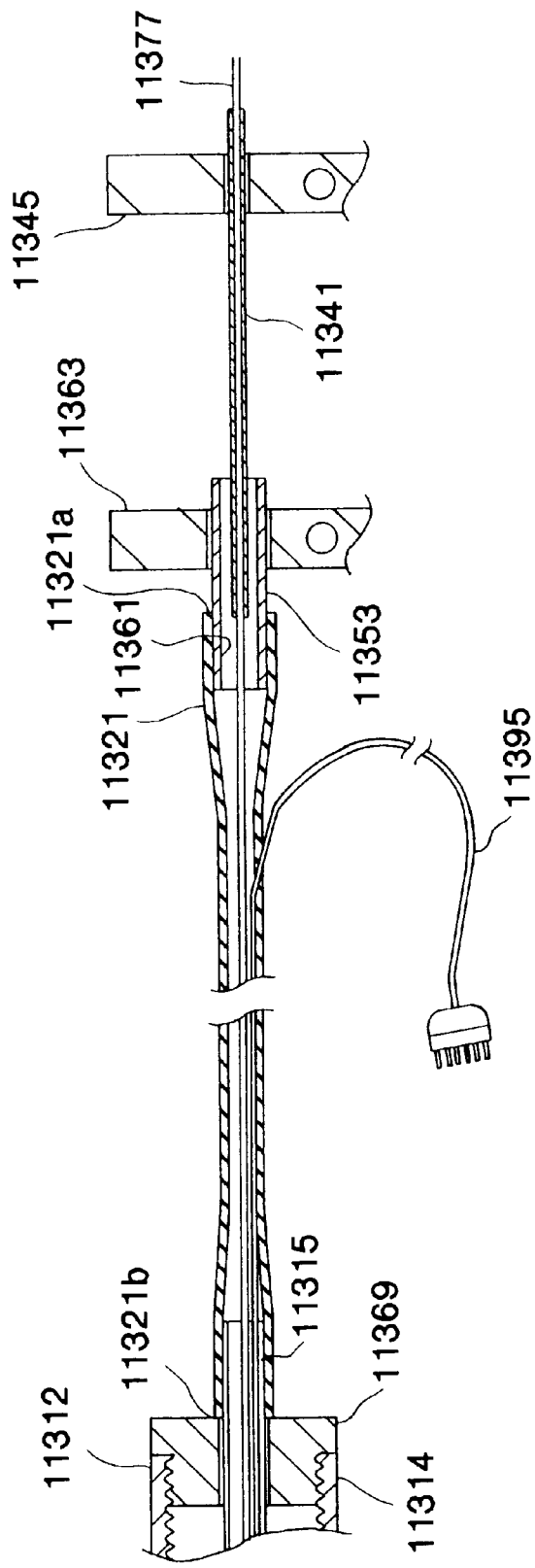
FIG. 42 is a cross-sectional view of the fiber of FIG. 40 passing through both the support tube and a bushing, and then extending into the handpiece.

FIG. 42 depicts the support tube 11341 and attached fiber 11377 passing through a bushing 11353 removably mounted onto the fixed arm 11329 of the actuator 11388. The bushing 11353 may be made of metal or plastic and has a longitudinal open bore 11363 for slidably receiving support tube 11341 and fiber 11377. The inner diameter of the bushing bore 11353 is greater than the outer diameter of the support tube 11341 in order to allow the support tube to freely slide within the bushing 11353.

The bushing 11353 is removably mounted to clamp 111363 of fixed arm 11329. The outer surface of the bushing 11353 is removably grasped by the clamp 11363. The clamp 11363 either releases or securely holds the tube by loosing or tightening, respectively, clamp adjustment handscrew 1365.

One terminal end 11321a of the cannula 11321 is attached to the bushing 11352 by partially inserting the bushing into the cannula 11321. Glue or the like may also be used in securing the cannula 11321 to the bushing 11352.

The other terminal end 11321b of the cannula 11321 is connected to a nipple 11315 extending from plug 11369 of handpiece 11312. The cannula 11321 is fitted over the outer surface of the nipple 11315 and may be secured to the nipple 11315 by glue, bonding or the like.

Figure 43:
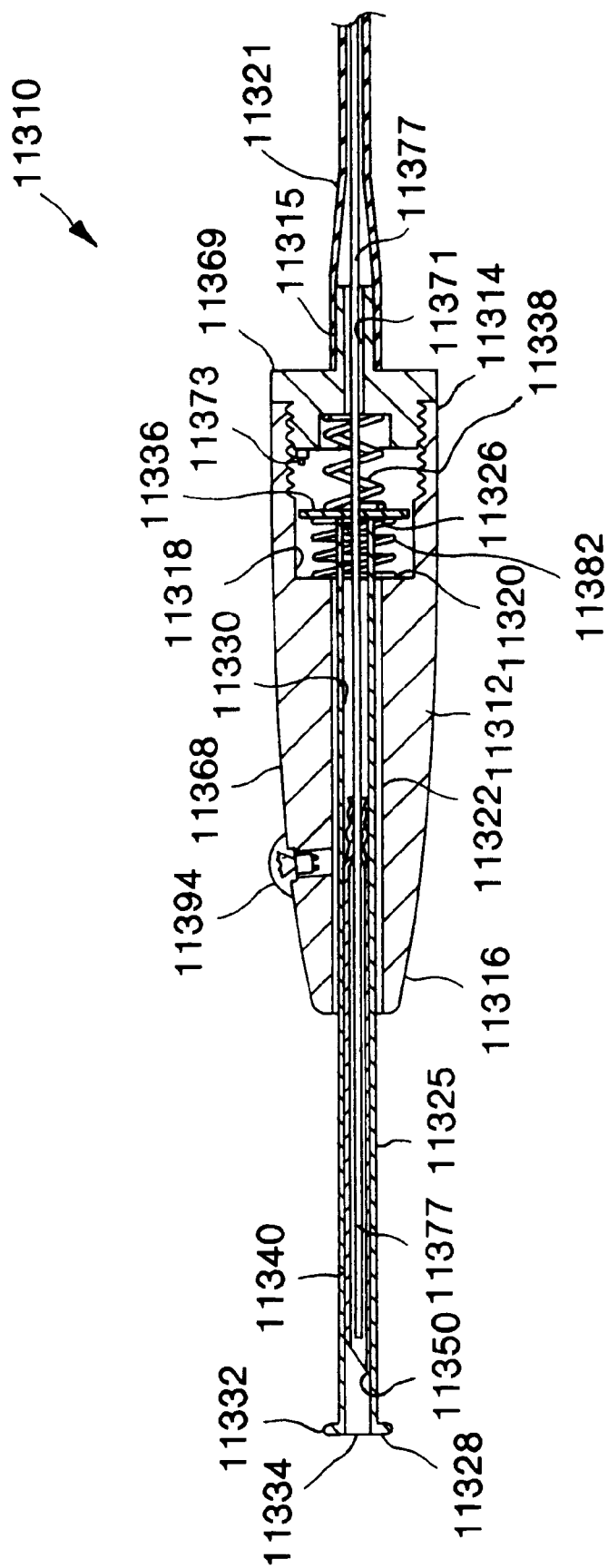
FIG. 43 is a partial cross-sectional view of the handpiece of FIG. 40.

FIG. 43 provides a partial cross-sectional view of the handpiece 11310. The handpiece 11310 includes a generally cylindrical housing 11312 having a first end 11314 and a tapered second end 11316 with an elongated cavity 11318 extending therebetween.

Extending within the housing cavity 11318 is a shoulder 11320. The shoulder 11320 is ring shaped and results in the housing cavity 11318 having a cylindrical longitudinal portion or passage 11322 that is in communication with the outside 11368 of the housing 11312 at the first end 11316.

Slidably mounted within the housing cavity 11318 and extending from the first end 11316 of the handpiece 11310 is a hollow needle collar or guide 11325. The needle collar 11325 is generally cylindrical in shape with an inner end 11326, an outer end 1328, and an open bore 11330 extending therebetween.

The inner end 11326 of the needle collar 11325 extends past shoulder 11320 and has a radially outwardly extending retaining ring 11336 with a larger outer diameter than the inner diameter of cavity passage 11322. Likewise, the outer end 11328 of the needle collar 11325 which protrudes from passage 11322 has a rounded flange 11332 extending around its periphery. The rounded flange 11332 results in the outer end 11328 of the needle collar 11325 having a flat disk shaped surface with the aperture 11334 to bore 11330 being located in the center.

Located between retaining ring 11336 and shoulder 11320 is coiled spring 11382 which wraps around the outer surface of the needle collar 11325. The coiled spring 11382 retractably biases the collar 11325 towards the first end 11314 of the housing 11312.

Threading mounted onto the first end 11314 of the housing 11312 is plug 11369 having an open bore 11371 in communication with the housing cavity 11318 and extending through nipple 11315. Extending through plug bore 11371 and into the needle collar bore 11330 is fiber 11377.

Further, mounted onto the plug 11369 is an electrical switch 11373 which faces towards retaining ring 11336. The switch 11373 provides a means for detecting when the needle collar 11325 has been pushed a fixed distance within the housing cavity 11318. Correspondingly, the switch 11373 is activated only when the retaining ring 11336 of the needle collar 11325 abuts against the switch 11373.

Resiliently biased against retaining ring 11336 and plug 11369 is coiled spring 11338 which forward biases the collar 11325 away from the first end 11314 of the housing 11312.

Attached to the housing 11312 is LED 11394 for indicating that the device 11310 is either ready to, or has completed, making a channel within tissue. The LED 11394 is operably connected to the control unit 11347 by conventional means such as wire leads within wire harness 11395.

Figure 44:
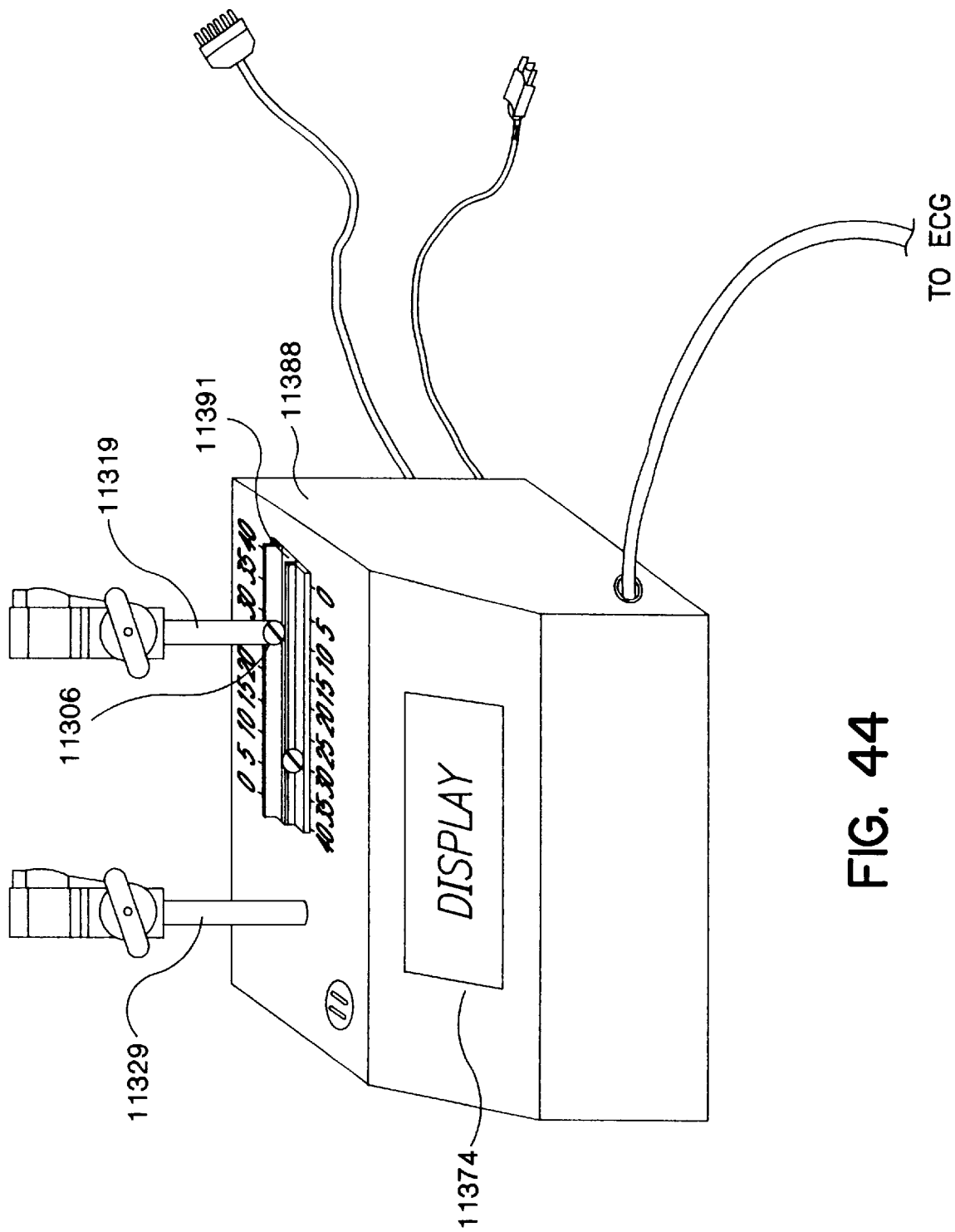
FIG. 44 is a perspective view of the external actuator depicted in FIG. 40.
Figure 46:
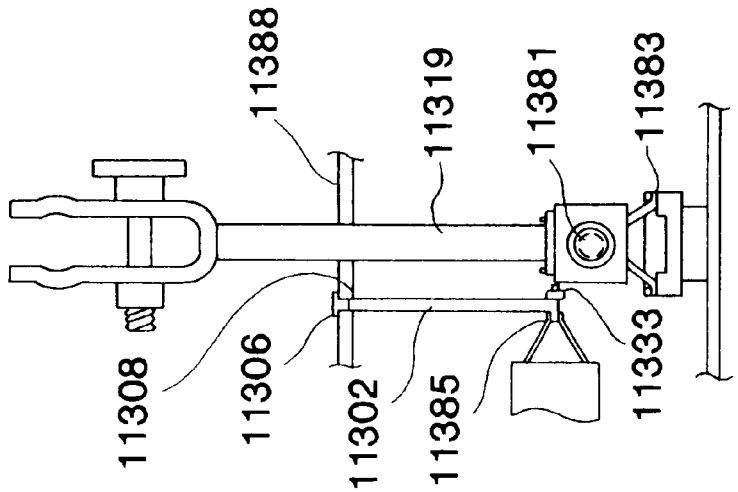
FIG. 46 is an end view of the external actuator along line 46—46 of FIG. 45.
Figure 45:
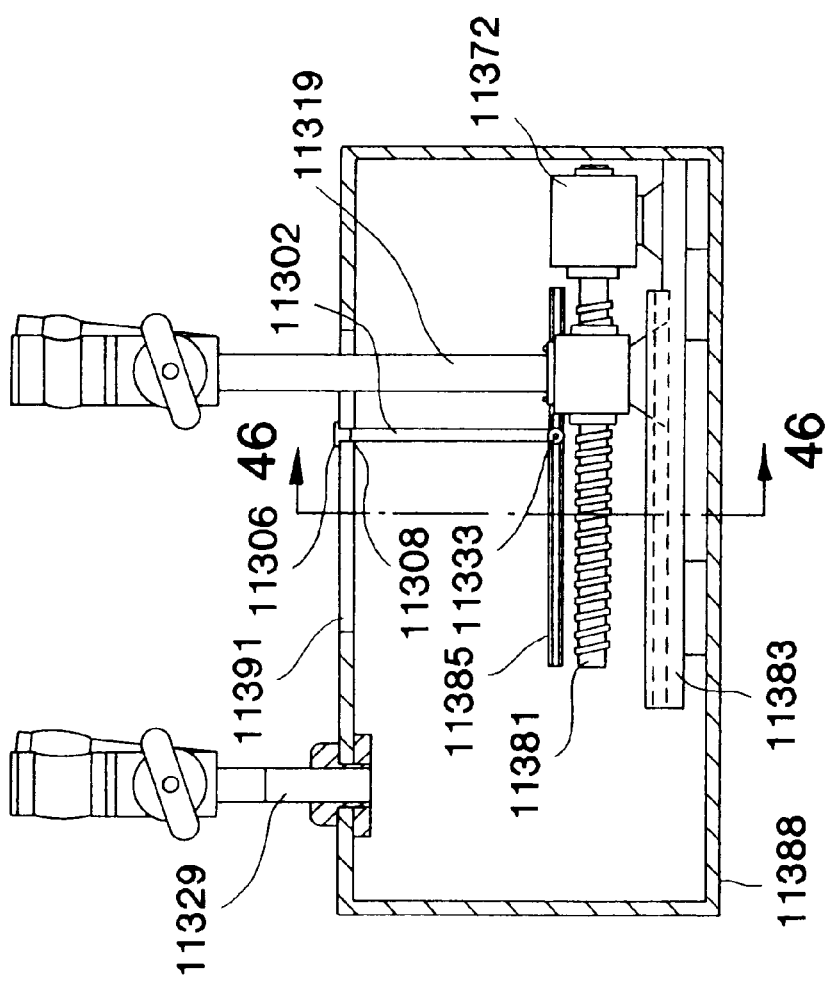
FIG. 45 is a fragmentary partial cross-sectional side view of the external actuator of FIG. 44.
Figure 48:
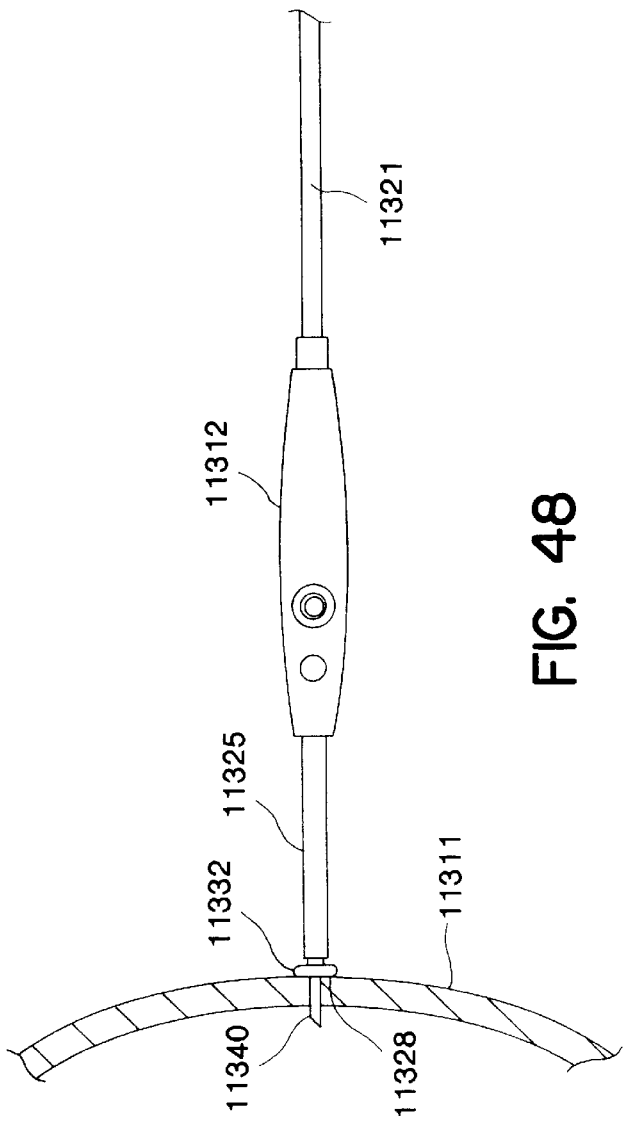
FIG. 48 depicts the handpiece of FIG. 40 pressed against a heart wall with the needle puncturing through the heart.

FIGS. 44–46 depict the external actuator 11388, preferably including a microprocessor, for advancing and withdrawing the optical fiber 11377 and needle 11340 a predetermined distance from the handpiece 11310. The actuator 11388 includes a stepper motor 11372 and a conventional active touch-screen display 11374. The stepper motor 11372 operates to advance and withdraw the optical fiber 11377 and needle 11340 a predetermined distance by moving drive arm 11319 towards and away from fixed arm 11329.

As seen in FIG. 45, stepper motor 11372 is mounted to the actuator housing and operates to bi-directional rotate shaft 11381 which is threadingly engaged by drive arm 11319. While a stepper motor is discussed, other means are contemplated including a piston, air pump or the like. Also mounted to the actuator housing and in spaced parallel relationship to shaft 11381 is track 11383 for sliding engaging drive arm 11319 between the stepper motor 11372 and fixed arm 11329.

In operation, longitudinal axial rotation of the shaft 11381 by the stepper motor 11372 in the clockwise direction, for example, results in the drive arm 11319 advancing towards the fixed arm 11329. Conversely, rotation in the counterclockwise direction moves the drive arm 11319 away from the fixed arm 11329.

Also mounted to the housing of the external actuator is an elongated track 11385 for slidingly adjusting the position of sensor 11333. The track 11385 is generally in spaced parallel relationship to the stepper motor shaft 11381. The sensor 11333 can be moved along track 11385 by attached post 11302 which extends into a elongated channel 11391 between arms 11319 and 11329.

Threadably attached to the distal end 11308 of post 11302 is a set screw 11307 for adjustable fixing the position of sensor 11333 along track 11385. The set screw 11307 abuts against the outside of the actuator housing and is adjustably secured to the housing by tightening the set screw. Correspondingly, positioning of the set screw 11308 results in like placement of the sensor 11333 along track 11385.

The sensor 11333 is activated, preferably, when it comes in contact with, or is brushed by, drive arm 11319. As such, the sensor 11333 detects when the drive arm 11319 is within a predetermined distance from the fixed arm 11329 which corresponds to the predetermined distance that the needle 11340 is advanced, or retracted, from the second end 11328 of the needle collar 11325.

FIG. 47, depicts a preferred embodiment of the display 11374 provided by the external actuator 11388. The display 11374 provides for selection and activation of various functions to be performed during a TMR procedure. The display 11374 in operable communication with a microprocessor in the control unit 11347 is stimulated by conventional means such as the touch of a finger.

The display 11374 includes options such as a "ACTIVATE ON COMMAND" touch area for activating the device 11310 to form a channel by depressing a button mounted on the handpiece or the like. The display 11374 also includes an "ACTIVATE ON "R" WAVE" touch area to command the device 11310 to form a channel when the next recognizable "r" wave is determined. Further, the display 11374 includes a "CUMULATIVE NUMBER OF CHANNELS" area for displaying how may channels have be formed by the device 11310. The count shown on the "CUMULATIVE NUMBER OF CHANNELS" area can be reset to zero by touching the "RESET CHANNELS TO ZERO" touch area.

Other operational settings such as the time and distance that the needle 11340 is to advance and retract from the handpiece 11312 are provided by the display 11374. These settings are selected by up touch area arrows 11331 and down touch area arrows 11364 provided on the display.

Referring back to FIGS. 18 and 40, the laser 11347 is enabled by depressing a footswitch or the like. The laser 11347 initially provides laser energy which is diverted into a heat sink by a mirror or shutter as explained above. The device 11310 is then operated by pressing the second end 11328 of the needle collar 11325 against heart 11311 until retaining ring 11336 abuts against switch 11374. Activation of switch 11374 results in the illumination of LED 11394 to indicate that the device 11310 is armed and is awaiting the next recognizable "r" wave of the patent's ECG.

Within the external actuator 11388 is a controller 11303, for determining when to form the channel in heart 11311, preferably within a predetermined amount of time. The controller 11303, preferably including a microprocessor, makes its determination by interposing an appropriate delay time from the next recognizable "r" wave of the patient's ECG, while taking care to avoid activation in the event any unusual variation in heart rhythm.

When the controller 11303 determines that a channel is to be made, the controller operates stepper motor 11372 to advance movable arm 11319 towards fixed arm 11329. As the arms 11319, 11329 are moved towards each other, support tube 11341 is pushed further within bushing 11353 which advances needle 11340 from the second end 11328 of the needle collar 11325 and into heart 11311 until the needle initially penetrates the middle layer.

As the fiber 11377 and attached needle 11340 initially penetrate the middle layer, movable arm 11319 actives switch 11333 which results in laser energy being emitted, via fiber 11377, from the fiber distal end 11378. The laser energy is, preferably, transmitted into the fiber by retracting a shutter or mirror within the laser unit 11347 as explained, in detail, above.

In one embodiment, the controller (microprocessor) 11303 continues to advance the needle 11340 until it is advanced the predetermined distance entered by the surgeon using display 11374 as depicted by FIG. 47. Thereafter, the microcontroller 11303 reverses the rotational direction of the stepper motor to retract the needle 11340 back into needle collar 11325.

As the needle 11340 is being retracted, movable arm 11319 again activates switch 11333 which stops the transmission of laser into fiber 11377 by deflecting the laser energy provided by the laser unit 11347 into a beam dump as explained, in detail, above, all within a predetermined amount of time.

The controller 11303 continues to retract the needle 11340 until the needle point 11350 is positioned back into the needle collar bore 11330. The LED 11394 is then turned off by microcontroller 11303 to indicated that the channel making process has been completed.

The surgeon may then remove his foot from the laser's footswitch and reposition the handpiece 11312 to repeat the process of making a channel in the heart 11311 or he may continue to depress the footswitch throughout the making of any number of channels.

Figure 49:
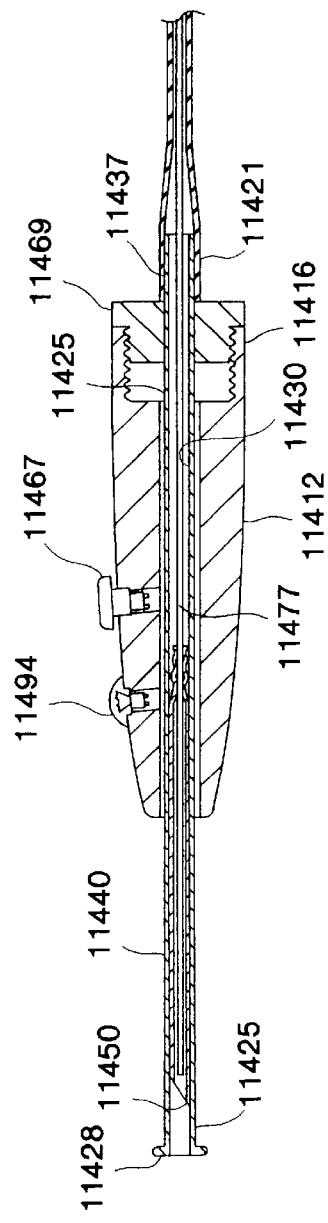
FIG. 49 is a cross-sectional view of another handpiece in accordance with the present invention wherein the needle collar is secured to the handpiece housing.

FIG. 49 depicts a cross-sectional view of another handpiece in accordance with the present invention. The handpiece 11412 is similar to that shown in FIGS. 21 and 43 except that the needle collar 11425 is securely mounted to the handpiece and an activating button 11467 is provided. Correspondingly, where appropriate, the last two digits in the 11400 series of numerals depicted in FIG. 49 are connected to elements which have the same function and/or structure as those described with regard to FIGS. 18–26 and 40–47.

In FIG. 49, needle collar 11425 is secured to plug 11369 and extends from the second end 11416 of the handpiece 11412. Attached to the portion 11437 of the needle collar 11425 that extends from the handpiece second end 11416 is cannula 11421.

The fiber 11477 within the cannula 11421 extends into the needle collar bore 11430. The pointed end 11450 of the needle 11440 attached to the fiber 11477 is positioned proximate to the needle collar second end 11428. Again, it is also contemplated that fiber 11477 could sliding reside within needle 11440.

Activating button 11467 is mounted on the outside of the handpiece 11412 and is operably connected to the controller 11340. The button 11447 is depressed by a surgeon when the second end of the needle collar 11428 is abutted against the heart. Depressing the button 11640 commands the device to begin forming a channel in the heart as described above with regard to FIGS. 18–26 and 40–47.

Referring to FIGS. 18, 27, 40, and 49, by adjusting the position of fiber 11477 within clamp 11345 of activator arm 11319, the distal end 11450 of needle 11440 may be extended 1 to 6 millimeters, preferably about 3 to 4 millimeters, distally from flange 11428 of needle collar 11425. In this embodiment, when device 11412 is pressed against the heart, needle 11440 penetrates into the heart tissue, penetrating either the epicardium or endocardium, before initially penetrating the myocardium. When button 11467 is depressed on the next recognizable "r" wave, the needle 11440 and fiber 11477, with laser transmission, advance through the tissue and then retract to their original position. Device 11412 and needle 11440 are then manually withdrawn from the heart.

FIG. 50 shows an alternate embodiment of the handpiece shown in FIG. 49 except that the needle collar is detachably secured to the handpiece and is curved at an angle of approximately thirty (30) degrees.

In FIG. 50, a threaded collar fitting 11570 is attached to the first end 11514 of the handpiece 11512. The needle collar 11525 longitudinally extends through an open bore 11575 in fitting 11570 and into housing cavity 11518. Adhesive 11576 is used to secure the needle collar to the fitting 11570. Further, the portion of the needle collar 11525 which extends from the handpiece 11512 is bent at an angle of approximately thirty degrees (30°).

In this embodiment, needle 11540 is 0.5 to 2.0 centimeters in length, preferably about 0.8 to 1.5 centimeters in length. Tubing 11584 surrounds the fiber 11577 and is attached proximate to needle 11540 to avoid the proximal end of needle 11540 hanging up on flange 11528 of needle collar 11525 when being retracted thereinto. Preferably, the tubing 11584 is made of plastic and has the same outside diameter as that of the needle 11540. The tubing 11584 is attached to the fiber 11577 by adhesive.

Tubing 11584 is about 100 centimeters in length, such that the tubing is longer than the stroke length of the external actuator.

FIG. 51 illustrates another handpiece 11612 which is similar to that shown in FIG. 50 except that the portion of the needle collar 11625 which extends from the handpiece is bent at an angle of approximately ninety degrees (90°). Alternate shapes of needle collar 11625 may range from 20° to 180°.

In the device 11310 illustrated by FIGS. 40–47, considerable recoil was encountered when the needle 11340 penetrated the epicardium, which is a tough, very dense, outer layer of the heart muscle. This recoil can be reduced by increasing the rate at which needle 11340 penetrates the epicardium, ramping up to the speed at which the needle 11340 penetrates the heart tissue. The recoil effect can also be reduced, as described above, by allowing the needle 11340 to extend 3 to 6 millimeters from the second end 11328 of the needle collar 11325. When the second end 11328 of needle collar 11325 is manually pressed against the heart, the needle passes into or through the epicardium. When the external actuator 11388 is activated, significantly less recoil results as the needle 11340 traverses the remainder of the heart tissue.

However, in order to prevent scratching of the heart or other tissue by the exposed needle when moving the device around the side or posterior surface of the heart, the needle may be temporarily retracted within the tube and extended when the device has been re-positioned.

Extending the needle from the tube also allows the needle to cool more effectively in the air, after lasing, and avoids heating the second end 11328 of the needle collar 11325 by not enclosing the hot needle therewithin.

Another benefit of extending the needle 11340 3 to 6 millimeters from the second end 11328 of the needle collar 11325 is that additional lasing time is obtained, allowing for more energy pulses to be emitted and a more uniform, larger diameter channel to be created. For example, if the heart wall is 15 millimeters thick, in the earlier described procedure, the needle would travel a total of 18 millimeters (3 millimeters into the heart chamber) and 18 millimeters back. Of this distance, for example, 4 millimeters in and 4 millimeters out of the epicardium would be without lasing. If the entire insertion and withdrawal is done in 0.4 seconds of the 0.6 second period of diastole, assuming a heart rate of 60, the rate of speed would be 36 millimeters in 0.4 seconds or 90 millimeters/second. Lasing would occur during 28 millimeters of the total 36 millimeters distance for 0.313 seconds (0.78 of 0.04 seconds). At a pulse repetition rate of 30 Hertz (2 joules per pulse), an average of 9.39 pulses would be emitted.

However, if the needle extends 4 millimeters distally from the needle collar, the total distance traveled, in and out, would be 28 millimeters (11 millimeters+3 millimeters in and 11 millimeters +3 millimeters out). Lasing can occur during the entire 0.4 second period. At the same pulse repetition rate of 30 Hertz, 12 pulses of energy would be emitted.

In Intra-Operative and Endoscopic TMR procedures, in order to make the diameter of the channel larger at the inside surface of the endocardium, (2 to 3 millimeters in diameter as is seen in alligator hearts), the speed at which the needle advances can be varied. If, for example, after the needle manually pierces the epicardium to a depth of 4 millimeters, it can be moved by the external actuator 11388 slower through the myocardium and slowest through the endocardium.

In Intra-Operative and Endoscopic TMR procedures, the device embodied in FIGS. 30–51 is placed against epicardium. When the control system is activated or the next "r" wave occurs, the fiber needle assembly penetrates the epicardium without lasing. The laser control device permits laser energy to be emitted from the distal end of said fiber as it advances through the myocardium and endocardium and into the heart chamber. In one preferred embodiment, the laser control device terminates transmission of the laser energy after the fiber has advanced through the myocardium and endocardium into the heart chamber.

However, an embodiment is contemplated in which the laser control device of FIGS. 30–51 terminates transmission of the laser energy at any time after the fiber has penetrated the chamber. That is, transmission may be terminated any time after the fiber has penetrated the heart chamber or is being withdrawn from the chamber, up to and including the time when the fiber has passed all or part of the way back through the myocardium.

For example, if laser energy is emitted as the fiber needle advances through the myocardium and endocardium into the chamber, having first penetrated the epicardium without lasing, and if laser energy is emitted as the fiber/needle is retracted through the endocardium, and the emission of laser energy is terminated before the fiber/needle re-enters the myocardium, the diameter of the channel in the endocardium will be wider than in the myocardium, having received twice the laser energy, reducing the likelihood of the channel closing.

Conversely, in a Percutaneous TMR procedure, the optical fiber is contained in a catheter inserted into an artery and extended through the aortic valve into the left ventricle. When the catheter is properly positioned against the chamber wall, i.e. the inner layer or endocardium, which may be ascertained through imaging or electrical sending means, the channels are made partially through the heart wall by a SPECTRAPROBE™ fiber optic device that is attached to the optical fiber. The SPECTRAPROBE™ fiber contains a metal tip with a central bore in which a lens, to diverge the laser beam, is mounted.

In any of the above described procedures, a therapeutic agent may be injected into the channel as the fiber/needle/inner catheter assembly is withdrawn, and after the emission of laser energy is terminated.

In a preferred embodiment for creating a cavity or pocket in the myocardium into which a therapeutic agent is to be deposited in a Percutaneous TMR procedure, the optical fiber contained in the catheter has a short length of needle attached to its distal end. The distal end of the catheter is placed against endocardium, so that the fiber/needle penetrates the first layer or endocardium without lasing, before initially penetrating the middle layer or myocardium. The laser control device transmits laser energy from the distal end of the fiber while the fiber needle advances through the middle layer or myocardium. Laser energy transmission ceases and, as the fiber needle is withdrawn from the middle layer or myocardium, the therapeutic agent is infused into the pocket created in the myocardium, after which the fiber/needle withdraws from the endocardium without lasing.

In both the Intra-Operative and Endoscopic or Percutaneous TMR procedures discussed above, it is recognized that injecting a therapeutic agent or drug into the tissue may promote vessel formation or other desired functions, such as adenyl cyclose to promote myocardial adrenergic signaling of agents to promote heart muscle regeneration, and is therefor desirable. In one preferred embodiment, the therapeutic agent is at least one angiogenic growth factor or other therapeutic agents, and/or at least one gene which causes cells to express such a growth factor or other therapeutic agents, which is injected into the channel through the needle, as the needle, and thus the fiber, are being withdrawn without lasing, as laser energy would destroy or damage the agent.

In the embodiments depicted in FIGS. 30–51, retraction of the fiber/needle assembly is accomplished by the control/actuator device linearly withdrawing the optical fiber from the heart tissue. In this embodiment, the transmission of laser energy has ceased when the channel reached the desired depth, although other embodiments are contemplated. The desired depth of channel was previously determined by setting the microprocessor which is in operable communication with the stepper motor controller. Description Delivery of a drug or therapeutic agent 11801 is accomplished by a delivery device 11803, depicted in FIG. 52 where the drug or agent 11801 comprises a drug, an angiogenic growth factor, a gene that causes cells to express an angiogenic growth factor, an adenyl cyclase, a gene that causes cells to express an adenyl cyclase able to cause muscle regeneration, a therapeutic agent, a gene that causes cells to express a therapeutic agent able to cause muscle regeneration or some combination or mixture thereof. While the delivery device 11803 is discussed in conjunction with the device shown in FIG. 50, it is contemplated that it can be used with any of the embodiments described above and depicted in FIGS. 1–51. Correspondingly, the last three digits in the 11000 series of numerals depicted in FIGS. 52–58 are connected to elements which have the same function and/or structure as those described with regard to FIGS. 1–51.

Figure 52:
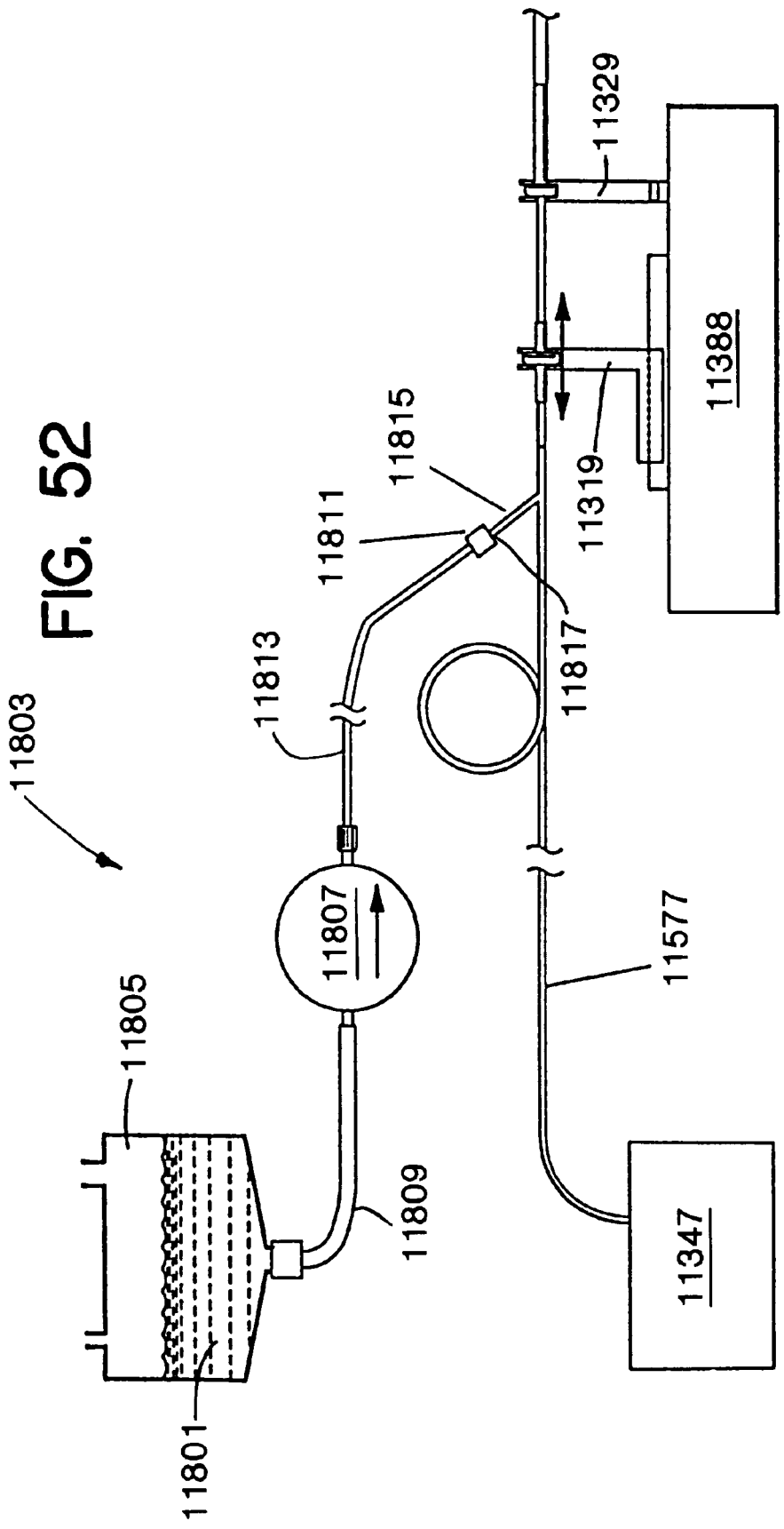
FIG. 52 is a schematic view of one embodiment of a delivery device suitable for use with any of the embodiments depicted in FIGS. 1–51.

As shown in FIG. 52, delivery system 11803 includes a reservoir 11805 and a pump 11807 in fluid communication with the device 11310 and needle (not shown). Additionally, other embodiments are contemplated including delivery device 11803 having a syringe and syringe actuating device. Timing of the delivery, and the amount, of the drug or agent 11801 is controlled by controller 11340 in operable communication therewith. Advancement of the optical fiber and vaporization of the tissue is initiated as discussed above, and may be synchronized with the patient's ECG. Furthermore, the delivery device 11803 is in operable communication with at least the laser control device 11347, preferably by means of controller 11340. In this manner, the drug or agent 11801 is delivered at the desired time after the termination of the laser transmission and during withdrawal of the needle 11040. After transmission of the laser beam is terminated, to avoid adversely effecting the drug or agent 11801, controller 11340 activates the delivery device 11803, initiating delivery of the drug or agent 11801.

In the embodiment discussed above and depicted in FIGS. 30–51, where a drug or other therapeutic agent 11801 is to be deposited into a pocket in the myocardium, laser energy is not transmitted until the needle 11040 initially penetrates the myocardium, after first penetrating the epicardium from the outside or the endocardium from the inside of the heart. In one preferred embodiment, the device 2710, 2910, 10010, 11010, 11210 and 11310 includes a timing device (not shown) in operable communication with the laser source 11347, whereby laser energy is transmitted only during the needle's first passage through the myocardium. The drug or therapeutic agent 11801 is injected as the needle 11040 is being withdrawn from the myocardium.

As provided above, the delivery device 11803 is in fluid communication with the device 11310. Activating the delivery device 11803, activates pump 11807 correspondingly causing the drug or agent 11801 to be dispensed into the channel, and thus exposes the tissue to the drug by means of the needle 11040. Reservoir 11805 is shown in fluid communication with pump 11807 by means of a conduit 11809, while pump 11807 is fluidly connected to a luer lock 11811 by means of a conduit 11813. In turn, the luer lock 11811 is in fluid communication with a port 11817 of a "y" connector 11815.

Figure 53:
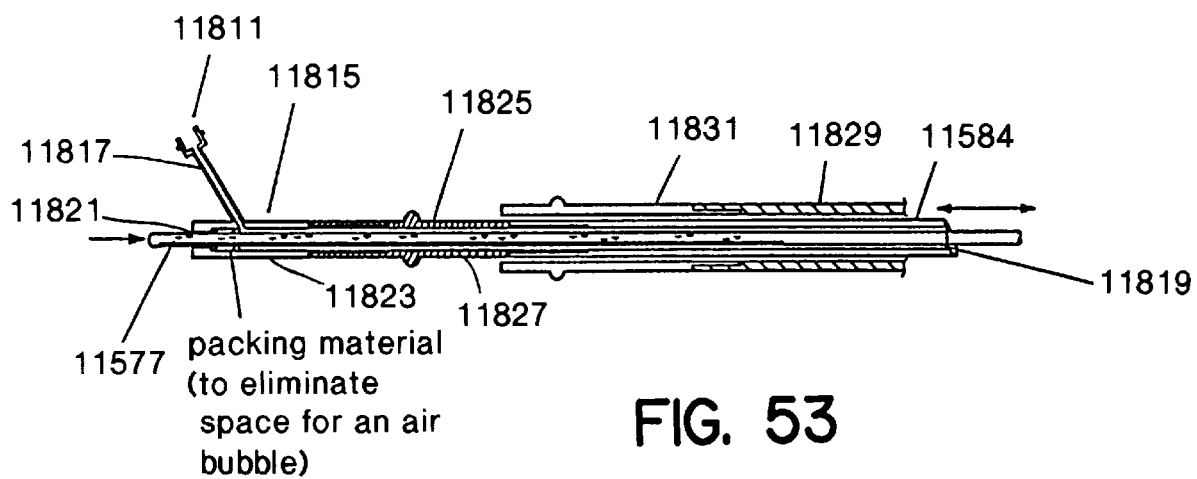
FIG. 53 is a cross-sectional side view of one embodiment of an inner catheter or tubing of the device of FIG. 52, which is held in place by fluid-tight attachment to the optical fiber.

Turning now to FIG. 53, in this embodiment it is clear that tubing 11584 is attached to and in fluid communication with the "y" connector 11815 connected to fiber 11577, preferably by adhesive, but other means are contemplated including bonding, about 100 cm proximal to the distal end of fiber 11577. Here, the optical fiber 11577 is not large enough to completely fill the lumen 11819, and thus tubing 11584 includes at least one fluid communication channel. Therefore, a means for fluidly connecting lumen 11819 of the inner catheter or tubing 11584 and an external fluid/drug/therapeutic agent source is shown, having in this embodiment luer lock 11811 at the end of a rigid, or flexible post, in fluid-tight attachment to the inner catheter or tubing 11584.

In accordance with the present invention, the apparatus will have a source of pulsed laser energy optically connected to the proximal end of (opposite from the needle end) optical fiber 11577 for delivery of laser energy to the needle 11040. In a preferred embodiment, the optical fiber 11577 extends into the needle 11040 from within the lumen 11819 of the inner catheter or tubing 11584 which is in fluid communication with drug delivery device 11803. Luer lock 11811 is attached to port 11817 of "y" connector 11815 by adhesive, bonding or other suitable means and can be used for infusion of drug or agent 11801 into the space between the fiber 11577 and tubing 11584.

The proximal end of the "y" connector 11815 further includes a port 11821 which allows the optical fiber 11577 to extend into and through a lumen 11823 of "y" connector 11815. In one preferred embodiment, the proximal portion of the lumen 11823 not taken up by the optical fiber 11577 is filled with packing material to eliminate space for forming air bubbles. The distal end of the "y" connector 11815 is further attached preferably by adhesive or bonding to a proximal end of a metal sleeve 11825, depicted having a flange, where a lumen 11827 of the metal sleeve 11825 is in fluid communication with the lumen 11823 of the "y" connector 11815.

Metal sleeve 11825 is in turn connected to inner catheter or tubing 11584, which are movably disposed within the proximal end of an outer catheter 11829 which is in operable communication with actuator 11388, where in one embodiment, it is contemplated that flexible cannula 11321 acts as the outer catheter 11829. In the embodiment depicted in FIG. 53, the proximal end of outer catheter 11829 is connected to the distal end of an outer sleeve 11831 having a flange, with the metal sleeve 11825 movably disposed therein. However, it is also contemplated that outer catheter 11829 is a single piece with the metal sleeve 11825 and inner catheter or tubing 11584 movably disposed therein, while the optical fiber 11577 is movably disposed in the metal sleeve 11825 and the inner catheter or tubing 11584. In the above described manner, optical fiber 11577 and tubing 11584 are movably disposed in the outer catheter 11829 which terminates in the handpiece, so that the delivery device 11803 is in fluid communication with needle 11040.

As shown in FIGS. 54–58, additional embodiments of the needle 11040 and optical fiber 11577 are contemplated for practicing the invention. While described in terms of a needle 11040, it is also contemplated, as discussed above, that a blunt ended tip 11833 may also be suitably formed for making the mechanical puncture of the tissue, and thus may incorporate the features described herein with reference to needle 11040. Such a tip 11833 may be formed from suitable metal or plastic.

In these particular embodiments, needle 11040 and/or tip 11833 can be crimped down and firmly attached to the optical fiber 11577 as shown. Tip 11833 is shown as blunt ended, but may be beveled to create a sharper puncturing tip. As shown in all figures, the single optical fiber 11577 may also be a suitable bundle of smaller diameter optical fibers.

Figure 54:
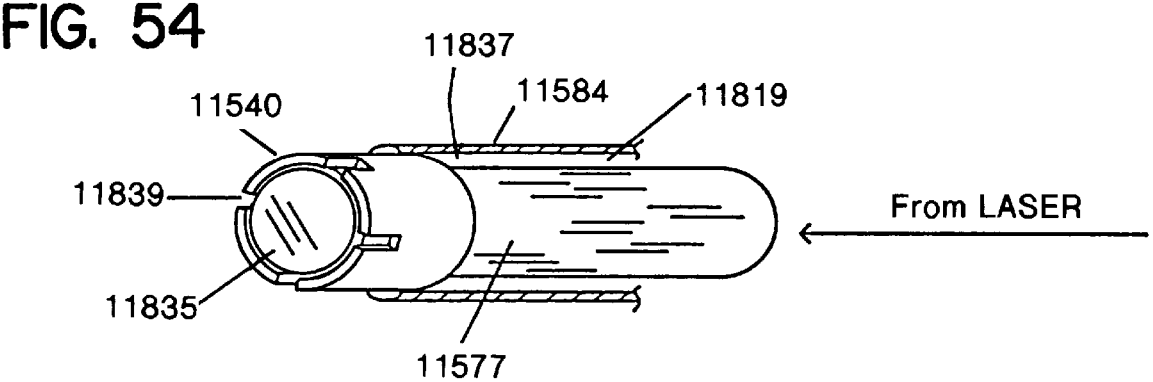
FIG. 54 is a partial sectional view of one embodiment of the optical fiber and inner catheter or tubing for use with the delivery device of FIG. 52 of the present invention (the positioning of an optical fiber within the lumen of the movable catheter or inner tubing is shown with the tubing or inner catheter being cut-away)

As shown in FIG. 54, a lens 11835 is contained in tip 11833, crimped to the optical fiber 11577 as shown, with fluid communication channels 11837 in fluid communication with lumen 11819 and the fluid ports 11839 formed in tip 11833 or needle 11040. The device of FIG. 54 is described in U.S. Pat. No. 4,773,413 to Hussein et al., and incorporated herein by reference. The lens 11835 diverges the beam to make a pocket of a larger diameter.

Figure 55:
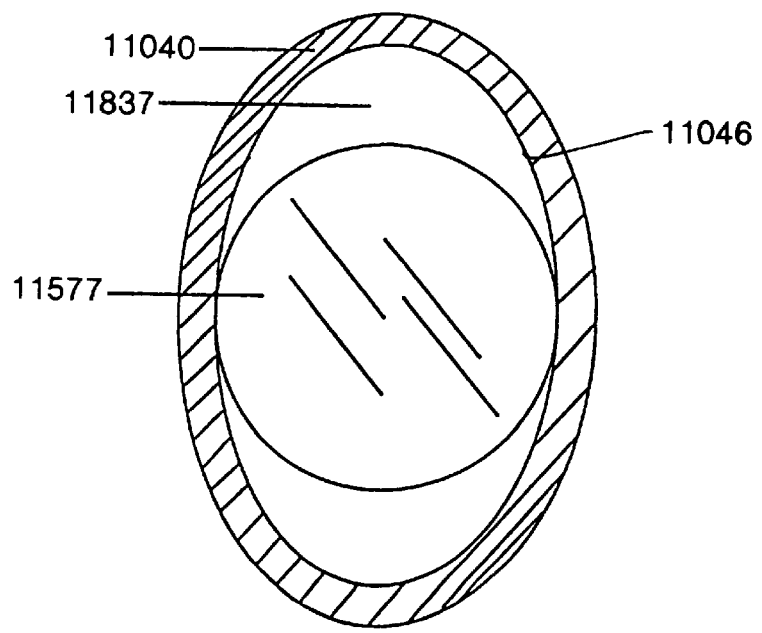
FIG. 55 is a cross-sectional view of one embodiment of the present invention wherein the needle is crimped so as to firmly fix the optical fiber within the bore of the needle, allowing fluid communication via the remaining space of the bore.

FIG. 55 depicts a cross-sectional view of one embodiment of the present invention wherein needle 11040 or tip 11833 is crimped so as to firmly fix the optical fiber 11577 within the bore 11046 thereof. This arrangement provides fluid communication via the remaining space of the bore 11046 XXXX, i.e., the fluid communication channel 11837 and the lumen 11819, and thus the delivery device 11803.

A plurality of fluid communication channels 11837 are shown in needle 11040 or tip 11833 and in fluid communication with lumen 11819. Fluid communication channels 11837 are cut within a buffer or jacket 11841 which fits around the optical fiber 11577 and within the bore 11046 of the needle 11040 or tip 11833 allowing fluid communication therethrough.

FIG. 57 depicts an embodiment in cross section similar to that of FIG. 56, however, protrusions 11843 of inner surface of the bore 11046 of the needle 11040 crimp down upon the fiber optic jacket 11841 holding the fiber optic 11577 firmly within and in place. A plurality of fluid communication channels 11837 in fluid communication with lumen 11819 are available as the spaces between the protrusions 11843.

In FIG. 58, yet another alternative embodiment of the present invention is shown in cross section. In this embodiment, the delivery device 11803 is in fluid communication through lumen 11819 with needle 11040 or tip 11833 via fluid communication channel within the bore 11046 of the needle 11040 and side ports 11545 to allow the drug or agent 11801 to be dispensed, the distal end of the optical fiber 11577 being surrounded by a jacket 11841 that allows the optical fiber 11577 to be fixed within the bore 11046 of the tip 11833 or needle 11040.

The timing device, is preferably accessed through the display 11374. Preferably, the timing device is set so that the laser energy is not transmitted until a predetermined amount of time after the needle initially penetrates the tissue, i.e., the amount of time it takes the needle to penetrate the epicardium or endocardium and initially penetrate the myocardium. In other words, after a predetermined amount of time, the laser energy is diverted from the heat sink into the fiber and onto the tissue to be vaporized.

While a timing device is preferred, other embodiments for transmitting laser energy only after the needle has penetrated the myocardium are contemplated. It is contemplated that the device 2710, 2910, 10010, 11010, 11210 and 11310 include a detecting device that detects a position of the needle, whereby laser energy is transmitted after the needle has initially penetrated the middle layer. This detecting device could take many forms.

Alternatively, ultrasound may be used to assist the surgeon to ascertain the thickness of the heart wall. The ultrasound procedure, may be used before the TMR procedure with the physician preparing a chart of the heart, indicating the thickness of the heart wall at various levels or areas, as well as during the TMR procedure, with the physician or an assistant periodically observing the ultrasound image display. Knowing the thickness of the heart tissue, the surgeon can than determine the distance the needle is to enter the heart tissue without lasing.

Conversely, an ultrasound emitting and receiving probe may be attached at the distal end of the needle collar or on a separate hand held device. The ultrasound image may be displayed on a TV monitor, so that the surgeon can visualize the thickness of the heart tissue at the point where the optical fiber penetrates the heart tissue.

In another preferred embodiment, the aforesaid ultrasound emitter/receiver may also transmit image data to the microprocessor, such as the one in the external actuator 11388, wherein the microprocessor processes the data to determine the thickness of the heart tissue. The microprocessor then operates the actuator 11388 such that the needle is advanced a selected distance into the heart wall and laser energy is emitted when and where desired.

Yet other detecting devices are contemplated including an adjustably positionable partition or sleeve flange. As provided above, an adjustable positionable partition and switch (not shown), similar to partition 2992 and switch 2959, in operable communication with laser source 11347 or display source 11374, could be used in the device for preselecting the desired depth that the needle and the fiber are to penetrate within the heart tissue before laser energy is transmitted. Likewise, an adjustably positionable sleeve flange (not shown) in operable communication with laser source 11347 or display source 11374, similar to sleeve flange 2904, could be utilized to preselect the desired depth that the needle and the fiber are to penetrate within the heart tissue before laser energy is transmitted.

Furthermore, in an intra-operative or endoscopic TMR procedure, with regard to the embodiments depicted above, after the fiber/needle has advanced through the epicardium without lasing from outside the heart, as the fiber/needle advances through the myocardium and endocardium while laser energy is being emitted, a plasma of hot gasses from the vaporization of tissue forms ahead of the fiber/needle. These hot gasses cannot escape backwards, as the tissue hugs the needle in the passageway, and solid tissue remains ahead of the fiber/needle. These hot gasses accumulate and cause the diameter of the channel to increase as the fiber/needle advances through the endocardium, which may result in a larger ultimate channel at the inner surface of the heart wall, with a greater likelihood of the channel remaining patent. However, a larger zone of coagulation about the channel and lateral damage to the myocardium may result. Consequently, it may be necessary to advance the needle and/or fiber at a given rate at a given energy level at different places within the heart wall to achieve a desirable and uniform channel diameter and coagulation zone.

It will be readily apparent from the foregoing detailed description of the invention and from the illustrations thereof that numerous variations and modifications may be effected without departing from the true spirit and scope of the novel concepts or principles of this invention.

We claim:

1. A surgical device for forming a channel within vascular tissue comprising:
   an optical fiber having a proximal end for optically coupling to a source of laser energy and a distal end for transmission of laser energy;
   a housing;
   a hollow guide having a distal end attached to said housing;
   a needle operably associated with said hollow guide and defining an open bore received within said hollow guide through which said optical fiber is received;
   an actuator operably connected to said needle for selectively extending said needle from said hollow guide relative to said distal end of said guide while said distal end of said fiber remains retracted within said bore; and
   a laser control device operably connected to said optical fiber transmitting said laser energy from said distal end only after said needle has entered the tissue to be treated;
   said actuator including a needle control device that mechanically selectively extends said needle a predetermined distance from said hollow guide in a reciprocal manner; and
   said needle control device including a microprocessor for preselecting said distance said needle extends from said hollow guide relative to said distal end of said guide.

2. The device of claim 1 wherein said actuator is operably connected to said optical fiber for reciprocally extending said fiber from said needle.

3. The device of claim 2 wherein said laser control device transmits said laser energy from said distal end of said fiber after said needle has initially penetrated a portion of the tissue to be treated and said fiber is extended therefrom.

4. The device of claim 1 wherein said laser control device terminates transmission of said laser energy after said fiber has penetrated an inner layer of the tissue to be treated.

5. The device of claim 1 wherein said laser control device terminates said transmission of said laser energy after said fiber has penetrated the inner layer and is withdrawn a selected distance therefrom.

6. The device of claim 1 wherein the optical fiber is coupled to a laser source which generates pulsed laser energy able to create acoustic shocks in said tissue.

7. The device of claim 6 wherein said laser control device further includes a timing device in operable communication with said laser source, whereby said laser energy is transmitted as said needle is penetrating the middle layer of the tissue to be treated.

8. The device of claim 6 wherein said laser control device further includes a detecting device that detects a position of said needle, whereby said laser energy is transmitted as said needle is penetrating the tissue to be treated.

9. The device of claim 8 wherein said detecting device determines when said needle has penetrated to a desired depth within the tissue.

10. The device of claim 1 wherein said hollow guide is a needle collar which is attached for reciprocation in said housing.

11. The device of claim 10 wherein said needle collar is operably connected to at least said actuator for selectively reciprocally extending said needle.

12. The device of claim 10 wherein said needle collar is operably connected to at least said laser control device for transmission of said laser energy from said distal end after said needle has penetrated the tissue to be treated.

13. The device of claim 1 wherein said hollow guide is a needle collar which is removably attached to said housing.

14. The device of claim 1 wherein said needle is mounted to said housing.

15. The device of claim 1 wherein said needle is removably mounted to said housing.

16. The device of claim 1 wherein said actuator operates by using compressed air.

17. The device of claim 1 wherein said actuator includes a stepper motor.

18. The device of claim 1 further including a display device operably connected to at least said control device for preselecting a distance that said needle reciprocally extends from said hollow guide.

19. The device of claim 1 further comprising a delivery device in fluid communication with said needle, whereby an agent is injected into the tissue.

20. The device of claim 19 wherein said agent includes at least an angiogenic growth factor.

21. The device of claim 19 wherein said agent includes at least a gene that causes cells to express an angiogenic growth factor.

22. The device of claim 19 wherein said agent includes at least a therapeutic agent.

23. The device of claim 19 wherein said agent includes at least an adenyl cyclase.

24. The device of claim 19 wherein said agent includes at least a gene that causes cells to express adenyl cyclase able to cause muscle regeneration.

25. The device of claim 19 wherein said agent includes at least a gene that causes cells to express a therapeutic agent able to cause muscle regeneration.

26. The device of claim 19 wherein said drug delivery device is operably connected to said laser control device, whereby said drug is injected into the tissue after transmission of said laser energy is terminated.

27. The device of claim 1 wherein said needle control device governs the rate at which said needle penetrates the tissue.

28. The device of claim 1 wherein said needle control device determines when on the cardial cycle to penetrate the tissue.

29. A surgical device for forming a channel within heart tissue having an epicardium, myocardium and an endocardium, comprising:
an optical fiber having a proximal end coupled to a source of laser energy and a distal end for transmission of laser energy;
a housing;
a hollow guide having a distal end attached to said housing;
a needle operably associated with said hollow guide and defining an open bore received within said hollow guide through which the optical fiber is received, wherein said needle is fixedly attached to said optical fiber;
an actuator operably connected to said needle and said optical fiber for selectively, reciprocally extending said needle and said optical fiber from said hollow guide relative to said distal end of said guide; and
a laser control device operably connected to said optical fiber transmitting said laser energy from said distal end only after said needle has penetrated the myocardium.

30. The device of claim 29 wherein said actuator includes a control device that mechanically extends said needle a predetermined distance from said hollow guide in a reciprocal manner.

31. The device of claim 30 wherein said control device includes a microprocessor for preselecting said distance said needle extends from said hollow guide relative to said distal end of said guide.

32. The device of claim 29 where said needle is fixedly attached to said optical fiber by crimping.

33. The device of claim 29 wherein said laser control device terminates transmission of said laser energy after said fiber has penetrated a selected distance through the heart tissue.

34. The device of claim 33 wherein said laser control device terminates said transmission of said laser energy after said fiber has penetrated a selected distance through the heart tissue and been withdrawn therefrom.

35. The device of claim 29 wherein said laser source is a pulsed laser able to create acoustic shock in muscle tissue in operable communication with a proximal end of said optical fiber.

36. The device of claim 35 wherein said laser control device includes a timing device in operable communication with said laser source, and whereby of said laser energy is transmitted after said needle has penetrated a predetermined distance.

37. The device of claim 29 wherein said hollow guide is a needle collar mounted for reciprocation in said housing.

38. The device of claim 37 wherein said needle collar is operably connected to at least said actuator for selectively extending said needle and said fiber.

39. The device of claim 37 wherein said needle collar is operably connected to said laser control device for transmitting said laser energy after said needle has passed through the epicardium.

40. The device of claim 29 wherein said hollow guide is a needle collar which is removably attached to said housing.

41. The device of claim 29 wherein said needle is mounted to said housing.

42. The device of claim 29 wherein said needle is removably mounted to said housing.

43. The device of claim 29 wherein said actuator is pneumatically energized.

44. The device of claim 29 wherein said actuator includes a stepper motor.

45. The device of claim 29 further including a display operably connected to at least said laser control device for preselecting a distance that said needle is to extend from said hollow guide.

46. The device of claim 29 further comprising an agent delivery device in fluid communication with said needle.

47. The device of claim 46 wherein said drug is at least an angiogenic drug.

48. The device of claim 47 wherein said control device penetrates the heart tissue after an appropriate delay time from the "r" wave of the patient's ECG.

49. The device of claim 46 wherein said drug delivery device is operably connected to said laser control device, whereby said drug is injected into the heart tissue after transmission of said laser energy is terminated.

50. The device of claim 29 wherein said control device governs the rate at which said needle penetrates the heart tissue.

51. The device of claim 50 wherein said control device alters the rate at which said needle penetrates the heart tissue.

52. The device of claim 50 wherein the channel is formed within the diastole period of one heart beat.

53. The device of claim 29 wherein said control device determines when to penetrate the heart tissue.

54. A surgical device for forming a channel within heart tissue having an epicardium, myocardium and an endocardium, comprising:
a source of laser energy;
an optical fiber having a proximal end operably coupled to said source of laser energy and a distal end for transmission of laser energy;
a housing having a distal end;
a needle operably associated with said housing and defining an open bore received within said housing through which the optical fiber is received, wherein said needle is fixedly attached to said optical fiber;
an actuator operably connected to said needle for selectively extending said needle and said fiber from said housing relative to said distal end of said housing, wherein said actuator includes a control device that selectively automatically extends said needle a predetermined distance from said housing in a reciprocal manner; and
a laser control device operably connected to said optical fiber transmitting said laser energy from said distal end only after said needle has penetrated the myocardium;
said laser control device including a microprocessor for preselecting said distance said needle extends from said housing relative to said distal end.

55. The device of claim 54 wherein said laser control device includes a timing device in operable communication with said laser source, whereby said laser energy is transmitted after said needle penetrates the myocardium.

56. The device of claim 54 wherein said laser control device includes a detecting device that detects a position of said needle, whereby said laser energy is transmitted after said needle penetrates the myocardium.

57. The device of claim 54 further comprising a drug delivery device in fluid communication with said needle.

58. The device of claim 57 wherein said drug delivery device is operably connected to said laser control device, whereby said drug is injected into a selected area of the heart tissue after transmission of said laser energy is terminated.

59. The device of claim 54 wherein said actuator further includes an ECG device.

60. The device of claim 54 wherein said actuator is operably connected to an ECG device.

* * * * *